(12) United States Patent
Cheng et al.

(10) Patent No.: US 7,794,963 B2
(45) Date of Patent: Sep. 14, 2010

(54) USE OF TETRACYSTEINE TAGS IN FLUORESCENCE-ACTIVATED CELL SORTING ANALYSIS OF PROKARYOTIC CELLS PRODUCING PEPTIDES OR PROTEINS

(75) Inventors: Qiong Cheng, Wilmington, DE (US); Kevin Michael Croker, Hockessin, DE (US); Stephen R. Fahnestock, Wilmington, DE (US); Tanja Maria Gruber, Media, PA (US); Kristin Ruebling-Jass, Wilmington, DE (US); Jianzhong Zhang, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 24 days.

(21) Appl. No.: 12/263,608

(22) Filed: Nov. 3, 2008

(65) Prior Publication Data

US 2009/0117609 A1  May 7, 2009

Related U.S. Application Data

(60) Provisional application No. 60/984,876, filed on Nov. 2, 2007.

(51) Int. Cl.
G01N 33/569 (2006.01)
C07K 16/00 (2006.01)
(52) U.S. Cl. ............................. 435/7.32; 530/329
(58) Field of Classification Search ............... None
See application file for complete search history.

(56) References Cited

U.S. PATENT DOCUMENTS

| | | | |
|---|---|---|---|
| 5,223,409 A | 6/1993 | Ladner et al. | |
| 5,403,484 A | 4/1995 | Ladner et al. | |
| 5,449,754 A | 9/1995 | Nishioka | |
| 5,480,971 A | 1/1996 | Houghten et al. | |
| 5,571,698 A | 11/1996 | Ladner et al. | |
| 5,585,275 A | 12/1996 | Hudson et al. | |
| 5,639,603 A | 6/1997 | Dower et al. | |
| 5,643,768 A | 7/1997 | Kawasaki | |
| 5,658,754 A | 8/1997 | Kawasaki | |
| 5,837,500 A | 11/1998 | Ladner et al. | |
| 5,932,474 A | 8/1999 | Tsien et al. | |
| 6,008,378 A | 12/1999 | Tsien et al. | |
| 6,054,271 A | 4/2000 | Tsien et al. | |
| 6,207,446 B1 | 3/2001 | Szostak et al. | |
| 6,214,553 B1 | 4/2001 | Szostak et al. | |
| 6,258,558 B1 | 7/2001 | Szostak et al. | |
| 6,261,804 B1 | 7/2001 | Szostak et al. | |
| 6,281,344 B1 | 8/2001 | Szostak et al. | |
| 6,312,927 B1 | 11/2001 | Hammond | |
| 6,416,950 B1 | 7/2002 | Lohse et al. | |
| 6,429,300 B1 | 8/2002 | Kurz et al. | |
| 6,436,665 B1 | 8/2002 | Kuimelis | |
| 6,451,564 B1 | 9/2002 | Guillouet et al. | |
| 6,518,018 B1 | 2/2003 | Szostak et al. | |
| 6,602,685 B1 | 8/2003 | Lohse | |
| 6,620,419 B1 | 9/2003 | Lintner | |
| 6,686,458 B2 | 2/2004 | Tsien et al. | |
| 6,831,160 B1 | 12/2004 | Vale et al. | |
| 6,846,655 B1 | 1/2005 | Wagner et al. | |
| 7,074,557 B2 | 7/2006 | Osbourn et al. | |
| 7,078,197 B2 | 7/2006 | Kurz et al. | |
| 7,138,503 B2 | 11/2006 | Tsien et al. | |
| 7,220,405 B2 | 5/2007 | Huang et al. | |
| 2003/0152976 A1 | 8/2003 | Janssen et al. | |
| 2003/0185870 A1 | 10/2003 | Grinstaff et al. | |
| 2005/0054752 A1 | 3/2005 | O'Brien et al. | |
| 2005/0176065 A1 | 8/2005 | Hanson | |

FOREIGN PATENT DOCUMENTS

| | | |
|---|---|---|
| EP | 1032837 | 10/1998 |
| EP | 1684073 | 10/1998 |
| WO | 2007023184 | 3/2007 |

OTHER PUBLICATIONS

Kemp, D. J., Proc. Natl. Acad. Sci. USA 78(7):4520-4524 (1981).
Chien et al., Proc. Natl. Acad. Sci. USA 88(21):9578-82 (1991).
Giepmans et al., Science 312:217-224 (2006).
Griffin et al., Science 281:269-271 (1998).
Ho et al., Infect. Immunity, 73(2):905-911 (2005).
Adams et al., JACS, 124:6063-6076 (2002).
Stroffekova et al., Eur. J. Physiol., 442:859-866 (2001).
Rice et al., Nat. Biotechnol., 19:321-326 (2001).
Griffin et al., Meth. Enzymol., 327:565-578 (2000).
Ignatova et al., PNAS, 101(2):523-528 (2004).

*Primary Examiner*—Suzanne M. Noakes

(57) ABSTRACT

A process of in vivo labeling and identifying recombinantly produced peptides or proteins within an unpermeabilized prokaryotic host cell. Recombinant prokaryotic cells expressing a fusion peptide comprising at least one tetracysteine tag were labeled in vivo using a biarsenical labeling reagent. A fluorescent activated cell sorter was used to identify and select subpopulations of fluorescent cells wherein the amount of fusion peptide in the cell was proportional to the amount of fluorescence detected.

13 Claims, 6 Drawing Sheets

With Lumio™ Green

With SimplyBlue™

SEQUENCE LISTING

```
<160> NUMBER OF SEQ ID NOS: 219

<210> SEQ ID NO 1
<211> LENGTH: 6
<212> TYPE: PRT
<213> ORGANISM: artificial sequence
<220> FEATURE:
<223> OTHER INFORMATION: synthetic cysteine motif
<220> FEATURE:
<221> NAME/KEY: MISC_FEATURE
<222> LOCATION: (3)..(4)
<223> OTHER INFORMATION: Xaa = any naturally-occurring amino acid except
      cysteine

<400> SEQUENCE: 1

Cys Cys Xaa Xaa Cys Cys
1               5

<210> SEQ ID NO 2
<211> LENGTH: 6
<212> TYPE: PRT
<213> ORGANISM: artificial sequence
<220> FEATURE:
<223> OTHER INFORMATION: synthetic cysteine motif

<400> SEQUENCE: 2

Cys Cys Pro Gly Cys Cys
1               5

<210> SEQ ID NO 3
<211> LENGTH: 24
<212> TYPE: DNA
<213> ORGANISM: artificial sequence
<220> FEATURE:
<223> OTHER INFORMATION: primer

<400> SEQUENCE: 3
gatcttgctg tccgggctgt tgcg                                              24

<210> SEQ ID NO 4
<211> LENGTH: 24
<212> TYPE: DNA
<213> ORGANISM: artificial sequence
```

```
<220> FEATURE:
<223> OTHER INFORMATION: primer

<400> SEQUENCE: 4
gatccgcaac agcccggaca gcaa                                              24

<210> SEQ ID NO 5
<211> LENGTH: 12
<212> TYPE: PRT
<213> ORGANISM: artificial sequence
<220> FEATURE:
<223> OTHER INFORMATION: hair binding peptide

<400> SEQUENCE: 5

Ile Pro Trp Trp Asn Ile Arg Ala Pro Leu Asn Ala
1               5                   10

<210> SEQ ID NO 6
<211> LENGTH: 7
<212> TYPE: PRT
<213> ORGANISM: artificial sequence
<220> FEATURE:
<223> OTHER INFORMATION: hair binding peptide

<400> SEQUENCE: 6

Asn Thr Ser Gln Leu Ser Thr
1               5

<210> SEQ ID NO 7
<211> LENGTH: 189
<212> TYPE: DNA
<213> ORGANISM: artificial sequence
<220> FEATURE:
<223> OTHER INFORMATION: synthetic construct encoding multi-block
      hair-binding peptide HC77643

<400> SEQUENCE: 7
gaccctggta tcccgtggtg gaacattcgc gcacctctga atgctggtgc tggtattccg       60
tggtggaaca tccgtgctcc tctgaacgcg ggtggctccg gtccgggctc cggtggcaac      120
acgagccaac tgagcaccgg tggtggcaac acttcccagc tgtccaccgg cggtccgaaa      180
aagtaataa                                                              189

<210> SEQ ID NO 8
<211> LENGTH: 61
<212> TYPE: PRT
<213> ORGANISM: artificial sequence
<220> FEATURE:
<223> OTHER INFORMATION: hair binding peptide

<400> SEQUENCE: 8

Asp Pro Gly Ile Pro Trp Trp Asn Ile Arg Ala Pro Leu Asn Ala Gly
1               5                   10                  15

Ala Gly Ile Pro Trp Trp Asn Ile Arg Ala Pro Leu Asn Ala Gly Gly
            20                  25                  30

Ser Gly Pro Gly Ser Gly Gly Asn Thr Ser Gln Leu Ser Thr Gly Gly
        35                  40                  45

Gly Asn Thr Ser Gln Leu Ser Thr Gly Gly Pro Lys Lys
    50                  55                  60

<210> SEQ ID NO 9
<211> LENGTH: 387
<212> TYPE: DNA
<213> ORGANISM: artificial sequence
```

<220> FEATURE:
<223> OTHER INFORMATION: synthetic construct encoding multi-block
hair-binding peptide HC776124

<400> SEQUENCE: 9

```
gaccctggca ttccgtggtg gaacattcgt gctcctctga atgcaggtgc gggcatccct    60
tggtggaata ttcgtgctcc gctgaacgcc ggtggttccg gtccgggtag cggtggtaat   120
acttctcagc tgtccacggg tggcggtaac actagccagc tgagcacggg cggccctaaa   180
aagccgggcg acccgggtat tccgtggtgg aatatccgtg ccccgctgaa cgcaggtgcc   240
ggcatcccgt ggtggaacat tcgtgcacct ctgaatgctg gtggttccgg tccaggctct   300
ggcggcaaca cttcccagct gtccaccggc ggtggcaaca ccagccagct gtctactggt   360
ggtccgaaga aaccgggtga ctaataa                                       387
```

<210> SEQ ID NO 10
<211> LENGTH: 127
<212> TYPE: PRT
<213> ORGANISM: artificial sequence
<220> FEATURE:
<223> OTHER INFORMATION: hair binding peptide

<400> SEQUENCE: 10

```
Asp Pro Gly Ile Pro Trp Trp Asn Ile Arg Ala Pro Leu Asn Ala Gly
 1               5                  10                  15
Ala Gly Ile Pro Trp Trp Asn Ile Arg Ala Pro Leu Asn Ala Gly Gly
            20                  25                  30
Ser Gly Pro Gly Ser Gly Gly Asn Thr Ser Gln Leu Ser Thr Gly Gly
        35                  40                  45
Gly Asn Thr Ser Gln Leu Ser Thr Gly Gly Pro Lys Lys Pro Gly Asp
    50                  55                  60
Pro Gly Ile Pro Trp Trp Asn Ile Arg Ala Pro Leu Asn Ala Gly Ala
65                  70                  75                  80
Gly Ile Pro Trp Trp Asn Ile Arg Ala Pro Leu Asn Ala Gly Gly Ser
                85                  90                  95
Gly Pro Gly Ser Gly Gly Asn Thr Ser Gln Leu Ser Thr Gly Gly Gly
            100                 105                 110
Asn Thr Ser Gln Leu Ser Thr Gly Gly Pro Lys Lys Pro Gly Asp
        115                 120                 125
```

<210> SEQ ID NO 11
<211> LENGTH: 162
<212> TYPE: DNA
<213> ORGANISM: artificial sequence
<220> FEATURE:
<223> OTHER INFORMATION: Synthetic construct. Nucleic acid sequence
encoding inclusion body tag IBT139

<400> SEQUENCE: 11

```
atgcagcagc gtttccagtg gcagttcgaa cagcagccgc gtggtcagca gcgtttccag    60
tggcagttcg aacagcagcc gcgtggtcag cagcgtttcc agtggcagtt cgaacagcag   120
ccggaaggtc agcagcgttt ccagtggcag ttcgaacagc ag                      162
```

<210> SEQ ID NO 12
<211> LENGTH: 56
<212> TYPE: PRT
<213> ORGANISM: artificial sequence
<220> FEATURE:
<223> OTHER INFORMATION: inclusion body tag

<400> SEQUENCE: 12

Met Gln Gln Arg Phe Gln Trp Gln Phe Glu Gln Pro Arg Gly Gln
1               5                   10                  15
Gln Arg Phe Gln Trp Gln Phe Glu Gln Pro Arg Gly Gln Gln Arg
            20                  25                  30
Phe Gln Trp Gln Phe Glu Gln Pro Glu Gly Gln Gln Arg Phe Gln
        35                  40                  45
Trp Gln Phe Glu Gln Gln Gly Ser
    50                  55

<210> SEQ ID NO 13
<211> LENGTH: 186
<212> TYPE: DNA
<213> ORGANISM: artificial sequence
<220> FEATURE:
<223> OTHER INFORMATION: Synthetic construct.  Nucleic acid sequence
      encoding inclusion body tag IBT139.CCPGCC

<400> SEQUENCE: 13
atgcagcagc gtttccagtg gcagttcgaa cagcagccgc gtggtcagca gcgtttccag      60
tggcagttcg aacagcagcc gcgtggtcag cagcgtttcc agtggcagtt cgaacagcag     120
ccggaaggtc agcagcgttt ccagtggcag ttcgaacagc agggatcttg ctgtccgggc     180
tgttgc                                                                186

<210> SEQ ID NO 14
<211> LENGTH: 61
<212> TYPE: PRT
<213> ORGANISM: artificial sequence
<220> FEATURE:
<223> OTHER INFORMATION: Synthetic construct - inclusion body tag
      IBT139.CCPGCC

<400> SEQUENCE: 14

Gln Gln Arg Phe Gln Trp Gln Phe Glu Gln Gln Pro Arg Gly Gln Gln
1               5                   10                  15
Arg Phe Gln Trp Gln Phe Glu Gln Gln Pro Arg Gly Gln Gln Arg Phe
            20                  25                  30
Gln Trp Gln Phe Glu Gln Gln Pro Glu Gly Gln Gln Arg Phe Gln Trp
        35                  40                  45
Gln Phe Glu Gln Gln Gly Ser Cys Cys Pro Gly Cys Cys
    50                  55                  60

<210> SEQ ID NO 15
<211> LENGTH: 384
<212> TYPE: DNA
<213> ORGANISM: artificial sequence
<220> FEATURE:
<223> OTHER INFORMATION: inclusion body tag

<400> SEQUENCE: 15
catatgcata ccccagaaca catcaccgcc gtggtacagc gctttgtggc tgcgctcaat      60
gccggcgatc tggacggcat cgtcgcgctg tttgccgatg acgccaccgt ggaagagccc     120
gtgggttccg agcccaggtc cggtacggct gcgtgtcgtg agttttacgc caactcgctc     180
aaactgcctt tggcggtgga gctgacgcag gagtgccgcg cggtcgccaa cgaagcggcc     240
ttcgctttca ccgtcagctt cgagtatcag ggccgcaaga ccgtagttgc gccctgtgat     300
cactttcgct tcaatggcgc cggcaaggtg gtgagcatcc gcgccttgtt tggcgagaag     360
aatattcacg catgccaggg atcc                                            384

<210> SEQ ID NO 16
<211> LENGTH: 128
<212> TYPE: PRT
<213> ORGANISM: artificial sequence
<220> FEATURE:
<223> OTHER INFORMATION: inclusion body tag

<400> SEQUENCE: 16

Met His Thr Pro Glu His Ile Thr Ala Val Val Gln Arg Phe Val Ala
1               5                   10                  15

Ala Leu Asn Ala Gly Asp Leu Asp Gly Ile Val Ala Leu Phe Ala Asp
            20                  25                  30

Asp Ala Thr Val Glu Glu Pro Val Gly Ser Glu Pro Arg Ser Gly Thr
        35                  40                  45

Ala Ala Cys Arg Glu Phe Tyr Ala Asn Ser Leu Lys Leu Pro Leu Ala
    50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Asp His Phe Arg Phe Asn Gly Ala Gly Lys Val Val Ser Ile
            100                 105                 110

Arg Ala Leu Phe Gly Glu Lys Asn Ile His Ala Cys Gln Gly Ser Asp
        115                 120                 125

<210> SEQ ID NO 17
<211> LENGTH: 11
<212> TYPE: PRT
<213> ORGANISM: artificial sequence
<220> FEATURE:
<223> OTHER INFORMATION: Synthetic Construct.  Core sequence found in
      IBT139 family of inclusion body tags.
<220> FEATURE:
<221> NAME/KEY: MISC_FEATURE
<222> LOCATION: (3)..(3)
<223> OTHER INFORMATION: Xaa = Arg, His, or Lys
<220> FEATURE:
<221> NAME/KEY: MISC_FEATURE
<222> LOCATION: (5)..(5)
<223> OTHER INFORMATION: Xaa = Gln, His, or Lys
<220> FEATURE:
<221> NAME/KEY: MISC_FEATURE
<222> LOCATION: (7)..(7)
<223> OTHER INFORMATION: Xaa = Gln, His, or Lys
<220> FEATURE:
<221> NAME/KEY: MISC_FEATURE
<222> LOCATION: (9)..(9)
<223> OTHER INFORMATION: Xaa = Glu or Gln
<220> FEATURE:
<221> NAME/KEY: MISC_FEATURE
<222> LOCATION: (10)..(10)
<223> OTHER INFORMATION: Xaa = Gln or Lys

<400> SEQUENCE: 17

Gln Gln Xaa Phe Xaa Trp Xaa Phe Xaa Xaa Gln
1               5                   10

<210> SEQ ID NO 18
<211> LENGTH: 6010
<212> TYPE: DNA
<213> ORGANISM: artificial sequence
<220> FEATURE:
<223> OTHER INFORMATION: plasmid pLR186

<400> SEQUENCE: 18

```
acacggtgcc tgactgcgtt agcaatttaa ctgtgataaa ctaccgcatt aaagcttgca    60
gtggcggttt tcatggcttg ttatgactgt ttttttgggg tacagtctat gcctcgggca   120
tccaagcagc aagcgcgtta cgccgtgggt cgatgtttga tgttatggag cagcaacgat   180
gttacgcagc agggcagtcg ccctaaaaca aagttaaaca tcatgaggga agcggtgatc   240
gccgaagtat cgactcaact atcagaggta gttggcgtca tcgagcgcca tctcgaaccg   300
acgttgctgg ccgtacattt gtacggctcc gcagtggatg gcggcctgaa gccacacagt   360
gatattgatt tgctggttac ggtgaccgta aggcttgatg aaacaacgcg gcgagctttg   420
atcaacgacc ttttggaaac ttcggcttcc cctggagaga gcgagattct ccgcgctgta   480
gaagtcacca ttgttgtgca cgacgacatc attccgtggc gttatccagc taagcgcgaa   540
ctgcaatttg gagaatggca cgcaatgac attcttgcag gtatcttcga ccagccacg    600 atcgacattg atctggctat cttgctgaca aaagcaagag aacatagcgt tgccttggta   660
ggtccagcgg cggaggaact ctttgatccg gttcctgaac aggatctatt tgaggcgcta   720
aatgaaacct taacgctatg gaactcgccg cccgactggg ctggcgatga gcgaaatgta   780
gtgcttacgt tgtcccgcat ttggtacagc gcagtaaccg gcaaaatcgc gccgaaggat   840
gtcgctgccg actgggcaat ggagcgcctg ccggcccagt atcagcccgt catacttgaa   900
gctagacagg cttatcttgg acaagaagaa gatcgcttgg cctcgcgcgc agatcagttg   960
gaagaatttg tccactacgt gaaaggcgag atcaccaagg tagtcggcaa ataatgtcta  1020
acaattcgtt caagcttggc tgttttggcg gatgagagaa gattttcagc ctgatacaga  1080
ttaaatcaga acgcagaagc ggtctgataa aacagaattt gcctggcggc agtagcgcgg  1140
tggtcccacc tgaccccatg ccgaactcag aagtgaaacg ccgtagcgcc gatggtagtg  1200
tggggtctcc ccatgcgaga gtagggaact gccaggcatc aaataaaacg aaaggctcag  1260
tcgaaagact gggcctttcg ttttatctgt tgtttgtcgg tgaacgctct cctgagtagg  1320
acaaatccgc cgggagcgga tttgaacgtt gcgaagcaac ggcccggagg gtggcgggca  1380
ggacgcccgc cataaactgc caggcatcaa attaagcaga aggccatcct gacgatggc   1440 cttttgcgt ttctacaaac tcttttgttt attttctaa atacattcaa atatgtatcc    1500
gctcatgaga caataaccct gataaatgct tcaataatat tgaaaaagga agagtatgag  1560
tattcaacat ttccgtgtcg cccttattcc cttttttgcg cattttgcc ttcctgtttt   1620 tgctcaccca gaaacgctgg tgaaagtaaa agatgctgaa gatcagttgg gtgcacgagt  1680
gggttacatc gaactggatc tcaacagcgg taagatcctt gagagttttc gccccgaaga  1740
acgttttcca atgatgagca cttttaaagt tctgctatgt ggcgcggtat tatcccgtgt  1800
tgacgccggg caagagcaac tcggtcgccg catacactat tctcagaatg acttggttga  1860
gtactcacca gtcacagaaa agcatcttac ggatggcatg acagtaagag aattatgcag  1920
tgctgccata accatgagtg ataacactgc ggccaactta cttctgacaa cgatcggagg  1980
accgaaggag ctaaccgctt ttttgcacaa catgggggat catgtaactc gccttgatcg  2040
ttgggaaccg gagctgaatg aagccatacc aaacgacgag cgtgacacca cgatgcctgt  2100
agcaatggca acaacgttgc gcaaactatt aactggcgaa ctacttactc tagcttcccg  2160
gcaacaatta atagactgga tggaggcgga taaagttgca ggaccacttc tgcgctcggc  2220
ccttccggct ggctggttta ttgctgataa atctggagcc ggtgagcgtg gtctcgcgg   2280 tatcattgca gcactggggc cagatggtaa gccctcccgt atcgtagtta tctacacgac  2340
ggggagtcag gcaactatgg atgaacgaaa tagacagatc gctgagatag gtgcctcact  2400
```

```
gattaagcat tggtaactgt cagaccaagt ttactcatat atactttaga ttgatttaaa    2460
acttcatttt taatttaaaa ggatctaggt gaagatcctt tttgataatc tcatgaccaa    2520
aatcccttaa cgtgagtttt cgttccactg agcgtcagac cccgtagaaa agatcaaagg    2580
atcttcttga tccttttttt ttctgcgcgt aatctgctgc ttgcaaacaa aaaaaccacc    2640
gctaccagcg gtggtttgtt tgccggatca agagctacca actcttttc cgaaggtaac    2700 tggcttcagc agagcgcaga taccaaatac tgtccttcta gtgtagccgt agttaggcca    2760
ccacttcaag aactctgtag caccgcctac atacctcgct ctgctaatcc tgttaccagt    2820
ggctgctgcc agtggcgata agtcgtgtct taccgggttg gactcaagac gatagttacc    2880
ggataaggcg cagcggtcgg gctgaacggg gggttcgtgc acacagccca gcttggagcg    2940
aacgacctac accgaactga gatacctaca gcgtgagcta tgagaaagcg ccacgcttcc    3000
cgaagggaga aaggcggaca ggtatccggt aagcggcagg gtcggaacag gagagcgcac    3060
gagggagctt ccagggggaa acgcctggta tctttatagt cctgtcgggt ttcgccacct    3120
ctgacttgag cgtcgatttt tgtgatgctc gtcagggggg cggagcctat ggaaaaacgc    3180
cagcaacgcg gccttttac ggttcctggc cttttgctgg ccttttgctc acatgttctt    3240
tcctgcgtta tccctgatt ctgtggataa ccgtattacc gcctttgagt gagctgatac    3300
cgctcgccgc agccgaacga ccgagcgcag cgagtcagtg agcgaggaag cggaagagcg    3360
cctgatgcgg tattttctcc ttacgcatct gtgcggtatt tcacaccgca tatatggtgc    3420
actctcagta caatctgctc tgatgccgca tagttaagcc agtatacact ccgctatcgc    3480
tacgtgactg ggtcatggct gcgccccgac acccgccaac accgctgacg cgccctgac    3540 gggcttgtct gctcccggca tccgcttaca gacaagctgt gaccgtctcc gggagctgca    3600
tgtgtcagag gttttcaccg tcatcaccga aacgcgcgag gcagcagatc aattcgcgcg    3660
cgaaggcgaa gcggcatgca taatgtgcct gtcaaatgga cgaagcaggg attctgcaaa    3720
ccctatgcta ctccgtcaag ccgtcaattg tctgattcgt taccaattat gacaacttga    3780
cggctacatc attcactttt tcttcacaac cggcacggaa ctcgctcggg ctggccccgg    3840
tgcatttttt aaatacccgc gagaaataga gttgatcgtc aaaaccaaca ttgcgaccga    3900
cggtggcgat aggcatccgg gtggtgctca aaagcagctt cgcctggctg atacgttggt    3960
cctcgcgcca gcttaagacg ctaatcccta actgctggcg aaaagatgt gacagacgcg    4020 acggcgacaa gcaaacatgc tgtgcgacgc tggcgatatc aaaattgctg tctgccaggt    4080
gatcgctgat gtactgacaa gcctcgcgta cccgattatc catcggtgga tggagcgact    4140
cgttaatcgc ttccatgcgc cgcagtaaca attgctcaag cagatttatc gccagcagct    4200
ccgaatagcg ccccttcccct tgcccggcgt taatgatttg cccaaacagg tcgctgaaat    4260
gcggctggtg cgcttcatcc gggcgaaaga accccgtatt ggcaaatatt gacggccagt    4320
taagccattc atgccagtag gcgcgcggac gaaagtaaac ccactggtga taccattcgc    4380
gagcctccgg atgacgaccg tagtgatgaa tctctcctgg cgggaacagc aaaatatcac    4440
ccggtcggca aacaaattct cgtccctgat ttttcaccac cccctgaccg cgaatggtga    4500
gattgagaat ataaccttc attcccagcg gtcggtcgat aaaaaaatcg agataaccgt    4560
tggcctcaat cggcgttaaa cccgccacca gatgggcatt aaacgagtat cccggcagca    4620
ggggatcatt ttgcgcttca gccatacttt tcatactccc gccattcaga agaaaacca    4680 attgtccata ttgcatcaga cattgccgtc actgcgtctt ttactggctc ttctcgctaa    4740
```

| | |
|---|---|
| ccaaaccggt aacccccgctt attaaaagca ttctgtaaca aagcgggacc aaagccatga | 4800 |
| caaaaacgcg taacaaaagt gtctataatc acggcagaaa agtccacatt gattatttgc | 4860 |
| acggcgtcac actttgctat gccatagcat ttttatccat aagattagcg gatcttacct | 4920 |
| gacgcttttt atcgcaactc tctactgttt ctccatacccc gttttttggg ctaacaggag | 4980 |
| gaattacata tgcagcagcg tttccagtgg cagttcgaac agcagccgcg tggtcagcag | 5040 |
| cgtttccagt ggcagttcga acagcagccg cgtggtcagc agcgtttcca gtggcagttc | 5100 |
| gaacagcagc cggaaggtca gcagcgtttc cagtggcagt tcgaacagca gggatccgac | 5160 |
| cctggcattc cgtggtggaa cattcgtgct cctctgaatg caggtgcggg catcccttgg | 5220 |
| tggaatattc gtgctccgct gaacgccggt ggttccggtc cgggtagcgg tggtaatact | 5280 |
| tctcagctgt ccacgggtgg cggtaacact agccagctga gcacgggcgg ccctaaaaag | 5340 |
| ccgggcgacc cgggtattcc gtggtggaat atccgtgccc cgctgaacgc aggtgccggc | 5400 |
| atcccgtggt ggaacattcg tgcacctctg aatgctggtg gttccggtcc aggctctggc | 5460 |
| ggcaacactt cccagctgtc caccggcggt ggcaacacca gccagctgtc tactggtggt | 5520 |
| ccgaagaaac cgggtgacta ataaggcgcg ccgacccagc tttcttgtac aaagtggttg | 5580 |
| attcgaggct gctaacaaag cccgaaagga agctgagttg gctgctgcca ccgctgagca | 5640 |
| ataactagca taaccccttg gggcctctaa acgggtcttg aggggttttt tgctgaaagg | 5700 |
| aggaactata tccggatatc cacaggacgg gtgtggtcgc catgatcgcg tagtcgatag | 5760 |
| tggctccaag tagcgaagcg agcaggactg ggcggcggcc aaagcggtcg acagtgctc | 5820 |
| cgagaacggg tgcgcataga aattgcatca acgcatatag cgctagcagc acgccatagt | 5880 |
| gactggcgat gctgtcggaa tggacgatat cccgcaagag gcccggcagt accggcataa | 5940 |
| ccaagcctat gcctacagca tccagggtga cggtgccgag gatgacgatg agcgcattgt | 6000 |
| tagatttcat | 6010 |

<210> SEQ ID NO 19
<211> LENGTH: 5083
<212> TYPE: DNA
<213> ORGANISM: artificial sequence
<220> FEATURE:
<223> OTHER INFORMATION: plasmid pTG28

<400> SEQUENCE: 19

| | |
|---|---|
| aagaaaccaa ttgtccatat tgcatcagac attgccgtca ctgcgtcttt tactggctct | 60 |
| tctcgctaac caaaccggta accccgctta ttaaaagcat tctgtaacaa agcgggacca | 120 |
| aagccatgac aaaaacgcgt aacaaaagtg tctataatca cggcagaaaa gtccacattg | 180 |
| attatttgca cggcgtcaca ctttgctatg ccatagcatt tttatccata agattagcgg | 240 |
| atcttacctg acgcttttta tcgcaactct ctactgtttc tccataccccg ttttttgggc | 300 |
| taacaggagg aattacatat gcataccccca gaacacatca ccgccgtggt acagcgcttt | 360 |
| gtggctgcgc tcaatgccgg cgatctggac ggcatcgtcg cgctgtttgc cgatgacgcc | 420 |
| acggtggaag agcccgtggg ttccgagccc aggtccggta cggctgcgtg tcgtgagttt | 480 |
| tacgccaact cgctcaaact gcctttggcg gtggagctga cgcaggagtg ccgcgcggtc | 540 |
| gccaacgaag cggccttcgc tttcaccgtc agcttcgagt atcagggccg caagaccgta | 600 |
| gttgcgccct gtgatcactt tcgcttcaat ggcgccggca aggtggtgag catccgcgcc | 660 |
| ttgtttggcg agaagaatat tcacgcatgc cagggatccg accctggtat cccgtggtgg | 720 |
| aacattcgcg cacctctgaa tgctggtgct ggtattccgt ggtggaacat ccgtgctcct | 780 |

```
ctgaacgcgg gtggctccgg tccgggctcc ggtggcaaca cgagccaact gagcaccggt    840
ggtggcaaca cttcccagct gtccaccggc ggtccgaaaa agtaataagg cgcgccgacc    900
cagctttctt gtacaaagtg gttgattcga ggctgctaac aaagcccgaa aggaagctga    960
gttggctgct gccaccgctg agcaataact agcataaccc cttggggcct ctaaacgggt   1020
cttgaggggt tttttgctga aaggaggaac tatatccgga tatccacagg acgggtgtgg   1080
tcgccatgat cgcgtagtcg atagtggctc caagtagcga agcgagcagg actgggcggc   1140
ggccaaagcg gtcggacagt gctccgagaa cgggtgcgca tagaaattgc atcaacgcat   1200
atagcgctag cagcacgcca tagtgactgg cgatgctgtc ggaatggacg atatcccgca   1260
agaggcccgg cagtaccggc ataaccaagc ctatgcctac agcatccagg gtgacggtgc   1320
cgaggatgac gatgagcgca ttgttagatt tcatacacgg tgcctgactg cgttagcaat   1380
ttaactgtga taaactaccg cattaaagct tatcgatgat aagctgtcaa acatgagaat   1440
tcgaagcttg gctgttttgg cggatgagag aagattttca gcctgataca gattaaatca   1500
gaacgcagaa gcggtctgat aaaacagaat ttgcctggcg gcagtagcgc ggtggtccca   1560
cctgacccca tgccgaactc agaagtgaaa cgccgtagcg ccgatggtag tgtggggtct   1620
ccccatgcga gagtagggaa ctgccaggca tcaaataaaa cgaaaggctc agtcgaaaga   1680
ctgggccttt cgttttatct gttgtttgtc ggtgaacgct ctcctgagta ggacaaatcc   1740
gccgggagcg gatttgaacg ttgcgaagca acggcccgga gggtggcggg caggacgccc   1800
gccataaact gccaggcatc aaattaagca gaaggccatc ctgacggatg ccttttttgc   1860
gtttctacaa actcttttgt ttattttttct aaatacattc aaatatgtat ccgctcatga   1920
gacaataacc ctgataaatg cttcaataat attgaaaaag gaagagtatg agtattcaac   1980
atttccgtgt cgcccttatt cccttttttg cggcattttg ccttcctgtt tttgctcacc   2040
cagaaacgct ggtgaaagta aaagatgctg aagatcagtt gggtgcacga gtgggttaca   2100
tcgaactgga tctcaacagc ggtaagatcc ttgagagttt tcgccccgaa gaacgttttc   2160
caatgatgag cacttttaaa gttctgctat gtggcgcggt attatcccgt gttgacgccg   2220
ggcaagagca actcggtcgc cgcatacact attctcagaa tgacttggtt gagtactcac   2280
cagtcacaga aaagcatctt acggatggca tgacagtaag agaattatgc agtgctgcca   2340
taaccatgag tgataacact gcggccaact tacttctgac aacgatcgga ggaccgaagg   2400
agctaaccgc ttttttgcac aacatggggg atcatgtaac tcgccttgat cgttgggaac   2460
cggagctgaa tgaagccata ccaaacgacg agcgtgacac cacgatgcct gtagcaatgg   2520
caacaacgtt gcgcaaacta ttaactggcg aactacttac tctagcttcc cggcaacaat   2580
taatagactg gatggaggcg gataaagttg caggaccact tctgcgctcg gcccttccgg   2640
ctggctggtt tattgctgat aaatctggag ccggtgagcg tgggtctcgc ggtatcattg   2700
cagcactggg gccagatggt aagccctccc gtatcgtagt tatctacacg acggggagtc   2760
aggcaactat ggatgaacga atagacaga tcgctgagat aggtgcctca ctgattaagc   2820
attggtaact gtcagaccaa gtttactcat atatacttta gattgattta aaacttcatt   2880
tttaatttaa aaggatctag gtgaagatcc ttttttgataa tctcatgacc aaaatccctt   2940
aacgtgagtt ttcgttccac tgagcgtcag accccgtaga aagatcaaa ggatcttctt   3000 gagatccttt ttttctgcgc gtaatctgct gcttgcaaac aaaaaaacca ccgctaccag   3060
cggtggtttg tttgccggat caagagctac caactctttt tccgaaggta actggcttca   3120
```

```
gcagagcgca gataccaaat actgtccttc tagtgtagcc gtagttaggc caccacttca    3180
agaactctgt agcaccgcct acatacctcg ctctgctaat cctgttacca gtggctgctg    3240
ccagtggcga taagtcgtgt cttaccgggt tggactcaag acgatagtta ccggataagg    3300
cgcagcggtc gggctgaacg ggggggttcgt gcacacagcc cagcttggag cgaacgacct    3360
acaccgaact gagataccta cagcgtgagc tatgagaaag cgccacgctt cccgaaggga    3420
gaaaggcgga caggtatccg gtaagcggca gggtcggaac aggagagcgc acgagggagc    3480
ttccaggggg aaacgcctgg tatctttata gtcctgtcgg gtttcgccac ctctgacttg    3540
agcgtcgatt tttgtgatgc tcgtcagggg ggcggagcct atggaaaaac gccagcaacg    3600
cggccttttt acggttcctg gccttttgct ggccttttgc tcacatgttc tttcctgcgt    3660 tatccctga ttctgtggat aaccgtatta ccgcctttga gtgagctgat accgctcgcc    3720
gcagccgaac gaccgagcgc agcgagtcag tgagcgagga agcggaagag cgcctgatgc    3780 ggtatttct ccttacgcat ctgtgcggta tttcacaccg catatatggt gcactctcag    3840
tacaatctgc tctgatgccg catagttaag ccagtataca ctccgctatc gctacgtgac    3900
tgggtcatgg ctgcgccccg acacccgcca cacccgctg acgcgccctg acgggcttgt    3960
ctgctcccgg catccgctta cagacaagct gtgaccgtct ccgggagctg catgtgtcag    4020
aggttttcac cgtcatcacc gaaacgcgcg aggcagcaga tcaattcgcg cgcgaaggcg    4080
aagcggcatg cataatgtgc ctgtcaaatg gacgaagcag ggattctgca aaccctatgc    4140
tactccgtca agccgtcaat tgtctgattc gttaccaatt atgacaactt gacggctaca    4200
tcattcactt tttcttcaca accggcacgg aactcgctcg ggctggcccc ggtgcatttt    4260 ttaaatacccg cgagaaaata gagttgatcg tcaaaaccaa cattgcgacc gacggtggcg    4320
ataggcatcc gggtggtgct caaaagcagc ttcgcctggc tgatacgttg gtcctcgcgc    4380
cagcttaaga cgctaatccc taactgctgg cggaaaagat gtgacagacg cgacggcgac    4440
aagcaaacat gctgtgcgac gctggcgata tcaaaattgc tgtctgccag gtgatcgctg    4500
atgtactgac aagcctcgcg tacccgatta tccatcggtg gatggagcga ctcgttaatc    4560
gcttccatgc gccgcagtaa caattgctca agcagattta tcgccagcag ctccgaatag    4620
cgcccttccc cttgcccggc gttaatgatt tgcccaaaca ggtcgctgaa atgcggctgg    4680
tgcgcttcat ccgggcgaaa gaaccccgta ttggcaaata ttgacggcca gttaagccat    4740
tcatgccagt aggcgcgcgg acgaaagtaa acccactggt gataccattc gcgagcctcc    4800
ggatgacgac cgtagtgatg aatctctcct ggcgggaaca gcaaaatatc acccggtcgg    4860
caaacaaatt ctcgtccctg attttttcacc acccccctgac cgcgaatggt gagattgaga    4920
atataacctt tcattcccag cggtcggtcg ataaaaaaat cgagataacc gttggcctca    4980
atcggcgtta aacccgccac cagatgggca ttaaacgagt atcccggcag caggggatca    5040
ttttgcgctt cagccatact tttcatactc ccgccattca gag    5083

<210> SEQ ID NO 20
<211> LENGTH: 5001
<212> TYPE: DNA
<213> ORGANISM: artificial sequence
<220> FEATURE:
<223> OTHER INFORMATION: plasmid pTG34

<400> SEQUENCE: 20
agatctcgat cccgcgaaat taatacgact cactataggg agaccacaac ggtttccctc      60
tagaaataat tttgtttaac tttaagaagg agatatacat atgcagcagc gtttccagtg     120
```

-continued

| | | |
|---|---|---|
| gcagttcgaa cagcagccgc gtggtcagca gcgtttccag tggcagttcg aacagcagcc | 180 | |
| gcgtggtcag cagcgtttcc agtggcagtt cgaacagcag ccggaaggtc agcagcgttt | 240 | |
| ccagtggcag ttcgaacagc agggatccga ccctggtatc ccgtggtgga acattcgcgc | 300 | |
| acctctgaat gctggtgctg gtattccgtg gtggaacatc cgtgctcctc tgaacgcggg | 360 | |
| tggctccggt ccgggctccg gtggcaacac gagccaactg agcaccggtg gtggcaacac | 420 | |
| ttcccagctg tccaccggcg gtccgaaaaa gtaataaggc gcgccgaccc agctttcttg | 480 | |
| tacaaagtgg ttgattcgag gctgctaaca agcccgaaa ggaagctgag ttggctgctg | 540 | |
| ccaccgctga gcaataacta gcataacccc ttggggcctc taaacgggtc ttgaggggtt | 600 | |
| ttttgctgaa aggaggaact atatccggat atccacagga cgggtgtggt cgccatgatc | 660 | |
| gcgtagtcga tagtggctcc aagtagcgaa gcgagcagga ctgggcggcg ccaaagcgg | 720 | |
| tcggacagtg ctccgagaac gggtgcgcat agaaattgca tcaacgcata tagcgctagc | 780 | |
| agcacgccat agtgactggc gatgctgtcg gaatggacga tatcccgcaa gaggcccggc | 840 | |
| agtaccggca taaccaagcc tatgcctaca gcatccaggg tgacggtgcc gaggatgacg | 900 | |
| atgagcgcat tgttagattt catacacggt gcctgactgc gttagcaatt taactgtgat | 960 | |
| aaactaccgc attaaagctt atcgatgata agctgtcaaa catgagaatt cttgaagacg | 1020 | |
| aaagggcctc gtgatacgcc tatttttata ggttaatgtc atgataataa tggtttctta | 1080 | |
| gacgtcaggt ggcacttttc ggggaaatgt gcgcggaacc cctatttgtt tatttttcta | 1140 | |
| aatacattca aatatgtatc cgctcatgag acaataaccc tgataaatgc ttcaataata | 1200 | |
| ttgaaaaagg aagagtatga gtattcaaca tttccgtgtc gcccttattc ccttttttgc | 1260 | |
| ggcattttgc cttcctgttt ttgctcaccc agaaacgctg gtgaaagtaa aagatgctga | 1320 | |
| agatcagttg ggtgcacgag tgggttacat cgaactggat ctcaacagcg gtaagatcct | 1380 | |
| tgagagtttt cgccccgaag aacgttttcc aatgatgagc acttttaaag ttctgctatg | 1440 | |
| tggcgcggta ttatcccgtg ttgacgccgg gcaagagcaa ctcggtcgcc gcatacacta | 1500 | |
| ttctcagaat gacttggttg agtactcacc agtcacagaa aagcatctta cggatggcat | 1560 | |
| gacagtaaga gaattatgca gtgctgccat aaccatgagt gataacactg cggccaactt | 1620 | |
| acttctgaca acgatcggag gaccgaagga gctaaccgct tttttgcaca acatggggga | 1680 | |
| tcatgtaact cgccttgatc gttgggaacc ggagctgaat gaagccatac caaacgacga | 1740 | |
| gcgtgacacc acgatgcctg cagcaatggc aacaacgttg cgcaaactat taactggcga | 1800 | |
| actacttact ctagcttccc ggcaacaatt aatagactgg atggaggcgg ataaagttgc | 1860 | |
| aggaccactt ctgcgctcgg cccttccggc tggctggttt attgctgata atctggagc | 1920 | |
| cggtgagcgt gggtctcgcg gtatcattgc agcactgggg ccagatggta agccctcccg | 1980 | |
| tatcgtagtt atctacacga cggggagtca ggcaactatg gatgaacgaa atagacagat | 2040 | |
| cgctgagata ggtgcctcac tgattaagca ttggtaactg tcagaccaag tttactcata | 2100 | |
| tatactttag attgatttaa aacttcattt ttaatttaaa aggatctagg tgaagatcct | 2160 | |
| ttttgataat ctcatgacca aaatccctta acgtgagttt tcgttccact gagcgtcaga | 2220 | |
| ccccgtagaa aagatcaaag gatcttcttg agatcctttt tttctgcgcg taatctgctg | 2280 | |
| cttgcaaaca aaaaaaccac cgctaccagc ggtggtttgt ttgccggatc aagagctacc | 2340 | |
| aactctttt ccgaaggtaa ctggcttcag cagagcgcag ataccaaata ctgtccttct | 2400 | |
| agtgtagccg tagttaggcc accacttcaa gaactctgta gcaccgccta catacctcgc | 2460 | |

```
tctgctaatc ctgttaccag tggctgctgc cagtggcgat aagtcgtgtc ttaccgggtt      2520
ggactcaaga cgatagttac cggataaggc gcagcggtcg ggctgaacgg ggggttcgtg      2580
cacacagccc agcttggagc gaacgaccta caccgaactg agatacctac agcgtgagct      2640
atgagaaagc gccacgcttc ccgaagggag aaaggcggac aggtatccgg taagcggcag      2700
ggtcggaaca ggagagcgca cgagggagct tccaggggga aacgcctggt atctttatag      2760
tcctgtcggg tttcgccacc tctgacttga gcgtcgattt ttgtgatgct cgtcaggggg      2820
gcggagccta tggaaaaacg ccagcaacgc ggccttttta cggttcctgg ccttttgctg      2880
gccttttgct cacatgttct ttcctgcgtt atcccctgat tctgtggata accgtattac      2940
cgcctttgag tgagctgata ccgctcgccg cagccgaacg accgagcgca gcgagtcagt      3000
gagcgaggaa gcggaagagc gcctgatgcg gtattttctc cttacgcatc tgtgcggtat      3060
ttcacaccgc atatatggtg cactctcagt acaatctgct ctgatgccgc atagttaagc      3120
cagtatacac tccgctatcg ctacgtgact gggtcatggc tgcgcccga cacccgccaa       3180 cacccgctga cgcgccctga cgggcttgtc tgctcccggc atccgcttac agacaagctg      3240
tgaccgtctc cgggagctgc atgtgtcaga ggttttcacc gtcatcaccg aaacgcgcga      3300
ggcagctgcg gtaaagctca tcagcgtggt cgtgaagcga ttcacagatg tctgcctgtt      3360
catccgcgtc cagctcgttg agtttctcca gaagcgttaa tgtctggctt ctgataaagc      3420
gggccatgtt aagggcggtt ttttcctgtt tggtcactga tgcctccgtg taagggggat      3480
ttctgttcat gggggtaatg ataccgatga acgagagag gatgctcacg atacgggtta      3540
ctgatgatga acatgcccgg ttactggaac gttgtgaggg taaacaactg gcggtatgga      3600
tgcggcggga ccagagaaaa atcactcagg gtcaatgcca gcgcttcgtt aatacagatg      3660
taggtgttcc acagggtagc cagcagcatc ctgcgatgca gatccggaac ataatggtgc      3720
agggcgctga cttccgcgtt tccagacttt acgaaacacg gaaaccgaag accattcatg      3780
ttgttgctca ggtcgcagac gttttgcagc agcagtcgct tcacgttcgc tcgcgtatcg      3840
gtgattcatt ctgctaacca gtaaggcaac cccgccagcc tagccgggtc ctcaacgaca      3900
ggagcacgat catgcgcacc cgtggccagg acccaacgct gcccgagatg cgccgcgtgc      3960
ggctgctgga gatggcggac gcgatggata tgttctgcca agggttggtt tgcgcattca      4020
cagttctccg caagaattga ttggctccaa ttcttggagt ggtgaatccg ttagcgaggt      4080
gccgccggct tccattcagg tcgaggtggc ccggctccat gcaccgcgac gcaacgcggg      4140
gaggcagaca aggtataggg cggcgcctac aatccatgcc aacccgttcc atgtgctcgc      4200
cgaggcggca taaatcgccg tgacgatcag cggtccagtg atcgaagtta ggctggtaag      4260
agccgcgagc gatccttgaa gctgtccctg atggtcgtca tctacctgcc tggacagcat      4320
ggcctgcaac gcgggcatcc cgatgccgcc ggaagcgaga agaatcataa tggggaaggc      4380
catccagcct cgcgtcgcga acgccagcaa gacgtagccc agcgcgtcgg ccgccatgcc      4440
ggcgataatg gcctgcttct cgccgaaacg tttggtggcg ggaccagtga cgaaggcttg      4500
agcgagggcg tgcaagattc cgaataccgc aagcgacagg ccgatcatcg tcgcgctcca      4560
gcgaaagcgg tcctcgccga aaatgaccca gagcgctgcc ggcacctgtc ctacgagttg      4620
catgataaag aagacagtca taagtgcggc gacgatagtc atgccccgcg cccaccggaa      4680
ggagctgact gggttgaagg ctctcaaggg catcggtcga tcgacgctct cccttatgcg      4740
actcctgcat taggaagcag cccagtagta ggttgaggcc gttgagcacc gccgccgcaa      4800
ggaatggtgc atgcaaggag atggcgccca acagtccccc ggccacgggg cctgccacca      4860
```

```
tacccacgcc gaaacaagcg ctcatgagcc cgaagtggcg agcccgatct tccccatcgg    4920
tgatgtcggc gatataggcg ccagcaaccg cacctgtggc gccggtgatg ccggccacga    4980
tgcgtccggc gtagaggatc g                                              5001

<210> SEQ ID NO 21
<211> LENGTH: 5812
<212> TYPE: DNA
<213> ORGANISM: artificial sequence
<220> FEATURE:
<223> OTHER INFORMATION: plasmid pLR173

<400> SEQUENCE: 21
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcttacctg acgcttttta tcgcaactct ctactgtttc tccatacccg tttttttggc     300
taacaggagg aattacatat gcagcagcgt ttccagtggc agttcgaaca gcagccgcgt     360
ggtcagcagc gtttccagtg gcagttcgaa cagcagccgc gtggtcagca gcgtttccag     420
tggcagttcg aacagcagcc ggaaggtcag cagcgtttcc agtggcagtt cgaacagcag     480
ggatccgacc ctggtatccc gtggtggaac attcgcgcac ctctgaatgc tggtgctggt     540
attccgtggt ggaacatccg tgctcctctg aacgcgggtg gctccggtcc gggctccggt     600
ggcaacacga gccaactgag caccggtggt ggcaacactt cccagctgtc caccggcggt     660
ccgaaaaagt aataaggcgc gccgacccag ctttcttgta caaagtggtt gattcgaggc     720
tgctaacaaa gcccgaaagg aagctgagtt ggctgctgcc accgctgagc aataactagc     780
ataacccctt ggggcctcta aacgggtctt gaggggtttt tgctgaaaag gaggaactat     840
atccggatat ccacaggacg ggtgtggtcg ccatgatcgc gtagtcgata gtggctccaa     900
gtagcgaagc gagcaggact gggcggcggc caaagcggtc ggacagtgct ccgagaacgg     960
gtgcgcatag aaattgcatc aacgcatata gcgctagcag cacgccatag tgactggcga    1020
tgctgtcgga tgacgata tcccgcaaga ggcccggcag taccggcata accaagccta     1080
tgcctacagc atccagggtg acggtgccga ggatgacgat gagcgcattg ttagatttca    1140
tacacggtgc ctgactgcgt tagcaattta actgtgataa actaccgcat aaagcttgc     1200 agtggcggtt ttcatggctt gttatgactg tttttttggg gtacagtcta tgcctcgggc    1260
atccaagcag caagcgcgtt acgccgtggg tcgatgtttg atgttatgga gcagcaacga    1320
tgttacgcag cagggcagtc gccctaaaac aaagttaaac atcatgaggg aagcggtgat    1380
cgccgaagta tcgactcaac tatcagaggt agttggcgtc atcgagcgcc atctcgaacc    1440
gacgttgctg gccgtacatt tgtacggctc cgcagtggat ggcggcctga agccacacag    1500
tgatattgat ttgctggtta cggtgaccgt aaggcttgat gaaacaacgc ggcgagcttt    1560
gatcaacgac cttttggaaa cttcggcttc cctggagag agcgagattc tccgcgctgt     1620
agaagtcacc attgttgtgc acgacgacat cattccgtgg cgttatccag ctaagcgcga    1680
actgcaattt ggagaatggc agcgcaatga cattcttgca ggtatcttcg agccagccac    1740
gatcgacatt gatctggcta tcttgctgac aaaagcaaga gaacatagcg ttgccttggt    1800
aggtccagcg gcggaggaac tctttgatcc ggttcctgaa caggatctat ttgaggcgct    1860
```

```
aaatgaaacc ttaacgctat ggaactcgcc gcccgactgg gctggcgatg agcgaaatgt    1920
agtgcttacg ttgtcccgca tttggtacag cgcagtaacc ggcaaaatcg cgccgaagga    1980
tgtcgctgcc gactgggcaa tggagcgcct gccggcccag tatcagcccg tcatacttga    2040
agctagacag gcttatcttg acaagaaga  agatcgcttg gcctcgcgcg cagatcagtt    2100
ggaagaattt gtccactacg tgaaaggcga gatcaccaag gtagtcggca ataatgtct     2160 aacaattcgt tcaagcttgg ctgttttggc ggatgagaga agattttcag cctgatacag    2220
attaaatcag aacgcagaag cggtctgata aaacagaatt tgcctggcgg cagtagcgcg    2280
gtggtcccac ctgaccccat gccgaactca gaagtgaaac gccgtagcgc cgatggtagt    2340
gtggggtctc cccatgcgag agtagggaac tgccaggcat caaataaaac gaaaggctca    2400
gtcgaaagac tgggcctttc gttttatctg ttgtttgtcg gtgaacgctc tcctgagtag    2460
gacaaatccg ccgggagcgg atttgaacgt tgcgaagcaa cggcccggag ggtggcgggc    2520
aggacgcccg ccataaactg ccaggcatca aattaagcag aaggccatcc tgacggatgg    2580
cctttttgcg tttctacaaa ctcttttgtt tattttcta  aatacattca aatatgtatc    2640
cgctcatgag acaataaccc tgataaatgc ttcaataata ttgaaaaagg aagagtatga    2700
gtattcaaca tttccgtgtc gcccttattc cctttttgc  ggcattttgc cttcctgttt    2760
ttgctcaccc agaaacgctg gtgaaagtaa aagatgctga agatcagttg ggtgcacgag    2820
tgggttacat cgaactggat ctcaacagcg gtaagatcct tgagagtttt cgccccgaag    2880
aacgttttcc aatgatgagc acttttaaag ttctgctatg tggcgcggta ttatcccgtg    2940
ttgacgccgg gcaagagcaa ctcggtcgcc gcatacacta ttctcagaat gacttggttg    3000
agtactcacc agtcacagaa aagcatctta cggatggcat gacagtaaga gaattatgca    3060
gtgctgccat aaccatgagt gataacactg cggccaactt acttctgaca acgatcggag    3120
gaccgaagga gctaaccgct tttttgcaca acatggggga tcatgtaact cgccttgatc    3180
gttgggaacc ggagctgaat gaagccatac caaacgacga gcgtgacacc acgatgcctg    3240
tagcaatggc aacaacgttg cgcaaactat taactggcga actacttact ctagcttccc    3300
ggcaacaatt aatagactgg atggaggcgg ataaagttgc aggaccactt ctgcgctcgg    3360
cccttccggc tggctggttt attgctgata aatctggagc cggtgagcgt gggtctcgcg    3420
gtatcattgc agcactgggg ccagatggta agccctcccg tatcgtagtt atctacacga    3480
cggggagtca ggcaactatg gatgaacgaa atagacagat cgctgagata ggtgcctcac    3540
tgattaagca ttggtaactg tcagaccaag tttactcata tatactttag attgatttaa    3600
aacttcattt ttaatttaaa aggatctagg tgaagatcct ttttgataat ctcatgacca    3660
aaatccctta acgtgagttt tcgttccact gagcgtcaga ccccgtagaa aagatcaaag    3720
gatcttcttg agatcctttt tttctgcgcg taatctgctg cttgcaaaca aaaaaaccac    3780
cgctaccagc ggtggtttgt ttgccggatc aagagctacc aactcttttt ccgaaggtaa    3840
ctggcttcag cagagcgcag ataccaaata ctgtccttct agtgtagccg tagttaggcc    3900
accacttcaa gaactctgta gcaccgccta catacctcgc tctgctaatc ctgttaccag    3960
tggctgctgc cagtggcgat aagtcgtgtc ttaccgggtt ggactcaaga cgatagttac    4020
cggataaggc gcagcggtcg ggctgaacgg ggggttcgtg cacacagccc agcttggagc    4080
gaacgaccta caccgaactg agatacctac agcgtgagct atgagaaagc gccacgcttc    4140
ccgaagggag aaaggcggac aggtatccgg taagcggcag gtcggaaca  ggagagcgca    4200 cgagggagct tccaggggga aacgcctggt atctttatag tcctgtcggg tttcgccacc    4260
```

```
tctgacttga gcgtcgattt ttgtgatgct cgtcaggggg gcggagccta tggaaaaacg    4320
ccagcaacgc ggccttttta cggttcctgg ccttttgctg gccttttgct cacatgttct    4380
ttcctgcgtt atcccctgat tctgtggata accgtattac cgcctttgag tgagctgata    4440
ccgctcgccg cagccgaacg accgagcgca gcgagtcagt gagcgaggaa gcggaagagc    4500
gcctgatgcg gtattttctc cttacgcatc tgtgcggtat tcacaccgc atatatggtg     4560 cactctcagt acaatctgct ctgatgccgc atagttaagc cagtatacac tccgctatcg    4620
ctacgtgact gggtcatggc tgcgccccga cacccgccaa cacccgctga cgcgccctga    4680
cgggcttgtc tgctcccggc atccgcttac agacaagctg tgaccgtctc cgggagctgc    4740
atgtgtcaga ggttttcacc gtcatcaccg aaacgcgcga ggcagcagat caattcgcgc    4800
gcgaaggcga agcggcatgc ataatgtgcc tgtcaaatgg acgaagcagg gattctgcaa    4860
accctatgct actccgtcaa gccgtcaatt gtctgattcg ttaccaatta tgacaacttg    4920
acggctacat cattcacttt tcttcacaa ccggcacgga actcgctcgg gctggccccg     4980
gtgcattttt taaatacccg cgagaaatag agttgatcgt caaaaccaac attgcgaccg    5040
acggtggcga taggcatccg ggtggtgctc aaaagcagct tcgcctggct gatacgttgg    5100
tcctcgcgcc agcttaagac gctaatccct aactgctggc ggaaaagatg tgacagacgc    5160
gacggcgaca agcaaacatg ctgtgcgacg ctggcgatat caaaattgct gtctgccagg    5220
tgatcgctga tgtactgaca agcctcgcgt acccgattat ccatcggtgg atggagcgac    5280
tcgttaatcg cttccatgcg ccgcagtaac aattgctcaa gcagatttat cgccagcagc    5340
tccgaatagc gccctttccc ttgcccggcg ttaatgattt gcccaaacag gtcgctgaaa    5400
tgcggctggt gcgcttcatc cgggcgaaag aaccccgtat tggcaaatat tgacggccag    5460
ttaagccatt catgccagta ggcgcgcgga cgaaagtaaa cccactggtg ataccattcg    5520
cgagcctccg gatgacgacc gtagtgatga atctctcctg gcgggaacag caaaatatca    5580
cccggtcggc aaacaaattc tcgtccctga tttttcacca cccctgaccg cgaatggtg    5640 agattgagaa tataaccttt cattcccagc ggtcggtcga taaaaaatc gagataaccg     5700 ttggcctcaa tcggcgttaa acccgccacc agatgggcat taaacgagta tcccggcagc    5760 agggatcat tttgcgcttc agccatactt ttcatactcc cgccattcag ag            5812
```

<210> SEQ ID NO 22
<211> LENGTH: 6034
<212> TYPE: DNA
<213> ORGANISM: artificial sequence
<220> FEATURE:
<223> OTHER INFORMATION: plasmid pLR199

<400> SEQUENCE: 22

```
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcttacctg acgctttta tcgcaactct ctactgtttc tccatacccg tttttttggc      300
taacaggagg aattacatat gcagcagcgt ttccagtgg agttcgaaca gcagccgcgt      360
ggtcagcagc gtttccagtg gcagttcgaa cagcagccgc gtggtcagca gcgtttccag    420
tggcagttcg aacagcagcc ggaaggtcag cagcgtttcc agtggcagtt cgaacagcag    480
```

```
ggatcttgct gtccgggctg ttgcggatcc gaccctggca ttccgtggtg aacattcgt    540 gctcctctga atgcaggtgc gggcatccct tggtggaata ttcgtgctcc gctgaacgcc    600
ggtggttccg gtccgggtag cggtggtaat acttctcagc tgtccacggg tggcggtaac    660
actagccagc tgagcacggg cggccctaaa aagccgggcg acccgggtat tccgtggtgg    720
aatatccgtg ccccgctgaa cgcaggtgcc ggcatcccgt ggtggaacat tcgtgcacct    780
ctgaatgctg gtggttccgg tccaggctct ggcggcaaca cttcccagct gtccaccggc    840
ggtggcaaca ccagccagct gtctactggt ggtccgaaga aaccgggtga ctaataaggc    900
gcgccgaccc agctttcttg tacaaagtgg ttgattcgag gctgctaaca aagcccgaaa    960
ggaagctgag ttggctgctg ccaccgctga gcaataacta gcataacccc ttggggcctc   1020
taaacgggtc ttgaggggtt ttttgctgaa aggaggaact atatccggat atccacagga   1080
cgggtgtggt cgccatgatc gcgtagtcga tagtggctcc aagtagcgaa gcgagcagga   1140
ctgggcggcg gccaaagcgg tcggacagtg ctccgagaac gggtgcgcat agaaattgca   1200
tcaacgcata tagcgctagc agcacgccat agtgactggc gatgctgtcg aatggacga    1260 tatcccgcaa gaggcccggc agtaccggca taaccaagcc tatgcctaca gcatccaggg   1320
tgacggtgcc gaggatgacg atgagcgcat tgttagattt catacacggt gcctgactgc   1380
gttagcaatt taactgtgat aaactaccgc attaaagctt gcagtggcgg ttttcatggc   1440
ttgttatgac tgtttttttg gggtacagtc tatgcctcgg gcatccaagc agcaagcgcg   1500
ttacgccgtg gtcgatgtt tgatgttatg gagcagcaac gatgttacgc agcagggcag   1560
tcgccctaaa acaaagttaa acatcatgag ggaagcggtg atcgccgaag tatcgactca   1620
actatcagag gtagttggcg tcatcgagcg ccatctcgaa ccgacgttgc tggccgtaca   1680
tttgtacggc tccgcagtgg atggcggcct gaagccacac agtgatattg atttgctggt   1740
tacggtgacc gtaaggcttg atgaaacaac gcggcgagct ttgatcaacg acctttggga   1800
aacttcggct tccctggag agagcgagat tctccgcgct gtagaagtca ccattgttgt   1860
gcacgacgac atcattccgt ggcgttatcc agctaagcgc gaactgcaat ttggagaatg   1920
gcagcgcaat gacattcttg caggtatctt cgagccagcc acgatcgaca ttgatctggc   1980
tatcttgctg acaaaagcaa gagaacatag cgttgccttg gtaggtccag cggcggagga   2040
actctttgat ccggttcctg aacaggatct atttgaggcg ctaaatgaaa ccttaacgct   2100
atggaactcg ccgcccgact gggctggcga tgagcgaaat gtagtgctta cgttgtcccg   2160
catttggtac agcgcagtaa ccggcaaaat cgcgccgaag gatgtcgctg ccgactgggc   2220
aatggagcgc ctgccggccc agtatcagcc cgtcatactt gaagctagac aggcttatct   2280
tggacaagaa gaagatcgct tggcctcgcg cgcagatcag ttggaagaat tgtccacta   2340 cgtgaaaggc gagatcacca aggtagtcgg caaataatgt ctaacaattc gttcaagctt   2400
ggctgttttg gcggatgaga aagattttc agcctgatac agattaaatc agaacgcaga   2460
agcggtctga taaaacagaa tttgcctggc ggcagtagcg cggtggtccc acctgacccc   2520
atgccgaact cagaagtgaa acgccgtagc gccgatggta gtgtggggtc tccccatgcg   2580
agagtaggga actgccaggc atcaaataaa acgaaaggct cagtcgaaag actgggcctt   2640
tcgttttatc tgttgtttgt cggtgaacgc tctcctgagt aggacaaatc cgccgggagc   2700
ggatttgaac gttgcgaagc aacggcccgg agggtggcgg gcaggacgcc cgccataaac   2760
tgccaggcat caaattaagc agaaggccat cctgacggat ggcctttttg cgtttctaca   2820
aactcttttg tttatttttc taaatacatt caaatatgta tccgctcatg agacaataac   2880
```

```
cctgataaat gcttcaataa tattgaaaaa ggaagagtat gagtattcaa catttccgtg    2940
tcgcccttat tcccttttt gcggcatttt gccttcctgt ttttgctcac ccagaaacgc    3000
tggtgaaagt aaaagatgct gaagatcagt tgggtgcacg agtgggttac atcgaactgg    3060
atctcaacag cggtaagatc cttgagagtt ttcgccccga agaacgtttt ccaatgatga    3120
gcacttttaa agttctgcta tgtggcgcgg tattatcccg tgttgacgcc gggcaagagc    3180
aactcggtcg ccgcatacac tattctcaga atgacttggt tgagtactca ccagtcacag    3240
aaaagcatct tacggatggc atgacagtaa gagaattatg cagtgctgcc ataaccatga    3300
gtgataacac tgcggccaac ttacttctga caacgatcgg aggaccgaag gagctaaccg    3360
cttttttgca caacatgggg gatcatgtaa ctcgccttga tcgttgggaa ccggagctga    3420
atgaagccat accaaacgac gagcgtgaca ccacgatgcc tgtagcaatg gcaacaacgt    3480
tgcgcaaact attaactggc gaactactta ctctagcttc ccggcaacaa ttaatagact    3540
ggatggaggc ggataaagtt gcaggaccac ttctgcgctc ggcccttccg gctggctggt    3600
ttattgctga taaatctgga gccggtgagc gtgggtctcg cggtatcatt gcagcactgg    3660
ggccagatgg taagccctcc cgtatcgtag ttatctacac gacggggagt caggcaacta    3720
tggatgaacg aaatagacag atcgctgaga taggtgcctc actgattaag cattggtaac    3780
tgtcagacca agtttactca tatatacttt agattgattt aaaacttcat ttttaattta    3840
aaaggatcta ggtgaagatc ctttttgata atctcatgac caaaatccct taacgtgagt    3900
tttcgttcca ctgagcgtca gaccccgtag aaaagatcaa aggatcttct tgagatcctt    3960
tttttctgcg cgtaatctgc tgcttgcaaa caaaaaaacc accgctacca gcggtggttt    4020
gtttgccgga tcaagagcta ccaactcttt ttccgaaggt aactggcttc agcagagcgc    4080
agataccaaa tactgtcctt ctagtgtagc cgtagttagg ccaccacttc aagaactctg    4140
tagcaccgcc tacatacctc gctctgctaa tcctgttacc agtggctgct gccagtggcg    4200
ataagtcgtg tcttaccggg ttggactcaa gacgatagtt accggataag gcgcagcggt    4260
cgggctgaac ggggggttcg tgcacacagc ccagcttgga gcgaacgacc tacaccgaac    4320
tgagatacct acagcgtgag ctatgagaaa gcgccacgct tcccgaaggg agaaaggcgg    4380
acaggtatcc ggtaagcggc agggtcggaa caggagagcg cacgagggag cttccagggg    4440
gaaacgcctg gtatctttat agtcctgtcg ggtttcgcca cctctgactt gagcgtcgat    4500
ttttgtgatg ctcgtcaggg gggcggagcc tatggaaaaa cgccagcaac gcggcctttt    4560
tacggttcct ggccttttgc tggccttttg ctcacatgtt ctttcctgcg ttatcccctg    4620
attctgtgga taaccgtatt accgcctttg agtgagctga taccgctcgc cgcagccgaa    4680
cgaccgagcg cagcgagtca gtgagcgagg aagcggaaga gcgcctgatg cggtatttc    4740 tccttacgca tctgtgcggt atttcacacc gcatatatgg tgcactctca gtacaatctg    4800
ctctgatgcc gcatagttaa gccagtatac actccgctat cgctacgtga ctgggtcatg    4860
gctgcgcccc gacacccgcc aacacccgct gacgcgccct gacgggcttg tctgctcccg    4920
gcatccgctt acagacaagc tgtgaccgtc tccgggagct gcatgtgtca gaggttttca    4980
ccgtcatcac cgaaacgcgc gaggcagcag atcaattcgc gcgcgaaggc gaagcggcat    5040
gcataatgtg cctgtcaaat ggacgaagca gggattctgc aaaccctatg ctactccgtc    5100
aagccgtcaa ttgtctgatt cgttaccaat tatgacaact tgacggctac atcattcact    5160
ttttcttcac aaccggcacg gaactcgctc gggctggccc cggtgcattt tttaaatacc    5220
```

-continued

| | |
|---|---|
| cgcgagaaat agagttgatc gtcaaaacca acattgcgac cgacggtggc gataggcatc | 5280 |
| cgggtggtgc tcaaaagcag cttcgcctgg ctgatacgtt ggtcctcgcg ccagcttaag | 5340 |
| acgctaatcc ctaactgctg gcggaaaaga tgtgacagac gcgacggcga caagcaaaca | 5400 |
| tgctgtgcga cgctggcgat atcaaaattg ctgtctgcca ggtgatcgct gatgtactga | 5460 |
| caagcctcgc gtacccgatt atccatcggt ggatggagcg actcgttaat cgcttccatg | 5520 |
| cgccgcagta acaattgctc aagcagattt atcgccagca gctccgaata gcgcccttcc | 5580 |
| ccttgcccgg cgttaatgat ttgcccaaac aggtcgctga atgcggctg gtgcgcttca | 5640 |
| tccgggcgaa agaaccccgt attggcaaat attgacggcc agttaagcca ttcatgccag | 5700 |
| taggcgcgcg gacgaaagta aacccactgg tgataccatt cgcgagcctc cggatgacga | 5760 |
| ccgtagtgat gaatctctcc tggcgggaac agcaaaatat cacccggtcg gcaaacaaat | 5820 |
| tctcgtccct gattttcac cacccctga ccgcgaatgg tgagattgag aatataacct | 5880 |
| ttcattccca gcgtcggtc gataaaaaaa tcgagataac cgttggcctc aatcggcgtt | 5940 |
| aaacccgcca ccagatgggc attaaacgag tatcccggca gcagggatc attttgcgct | 6000 |
| tcagccatac ttttcatact cccgccattc agag | 6034 |

<210> SEQ ID NO 23
<211> LENGTH: 5107
<212> TYPE: DNA
<213> ORGANISM: artificial sequence
<220> FEATURE:
<223> OTHER INFORMATION: plasmid pDCQ500

<400> SEQUENCE: 23

| | |
|---|---|
| aagaaaccaa ttgtccatat tgcatcagac attgccgtca ctgcgtcttt tactggctct | 60 |
| tctcgctaac caaaccggta accccgctta ttaaaagcat tctgtaacaa agcgggacca | 120 |
| aagccatgac aaaaacgcgt aacaaaagtg tctataatca cggcagaaaa gtccacattg | 180 |
| attatttgca cggcgtcaca ctttgctatg ccatagcatt tttatccata agattagcgg | 240 |
| atcttacctg acgcttttta tcgcaactct ctactgtttc tccatacccg tttttttgggc | 300 |
| taacaggagg aattacatat gcataccca gaacacatca ccgccgtggt acagcgcttt | 360 |
| gtggctgcgc tcaatgccgg cgatctggac ggcatcgtcg cgctgtttgc cgatgacgcc | 420 |
| acggtggaag agcccgtggg ttccgagccc aggtccggta cggctgcgtg tcgtgagttt | 480 |
| tacgccaact cgctcaaact gccttttggcg gtggagctga cgcaggagtg ccgcgcggtc | 540 |
| gccaacgaag cggccttcgc tttcaccgtc agcttcgagt atcagggccg caagaccgta | 600 |
| gttgcgccct gtgatcactt tcgcttcaat ggcgccggca aggtggtgag catccgcgcc | 660 |
| ttgtttggcg agaagaatat tcacgcatgc cagggatctt gctgtccggg ctgttgcgga | 720 |
| tccgaccctg gtatcccgtg gtggaacatt cgcgcacctc tgaatgctgg tgctggtatt | 780 |
| ccgtggtgga acatccgtgc tcctctgaac gcggtggct ccggtccggg ctccggtggc | 840 |
| aacacgagcc aactgagcac cggtggtggc aacacttccc agctgtccac cggcggtccg | 900 |
| aaaaagtaat aaggcgcgcc gacccagctt tcttgtacaa agtggttgat tcgaggctgc | 960 |
| taacaaagcc cgaaaggaag ctgagttggc tgctgccacc gctgagcaat aactagcata | 1020 |
| accccttggg gcctctaaac gggtcttgag ggttttttg ctgaaaggag gaactatatc | 1080 |
| cggatatcca caggacgggt gtggtcgcca tgatcgcgta gtcgatagtg gctccaagta | 1140 |
| gcgaagcgag caggactggg cggcggccaa agcggtcgga cagtgctccg agaacgggtg | 1200 |
| cgcatagaaa ttgcatcaac gcatatagcg ctagcagcac gccatagtga ctggcgatgc | 1260 |

-continued

```
tgtcggaatg gacgatatcc cgcaagaggc ccggcagtac cggcataacc aagcctatgc    1320
ctacagcatc cagggtgacg gtgccgagga tgacgatgag cgcattgtta gatttcatac    1380
acggtgcctg actgcgttag caatttaact gtgataaact accgcattaa agcttatcga    1440
tgataagctg tcaaacatga gaattcgaag cttggctgtt ttggcggatg agagaagatt    1500
ttcagcctga tacagattaa atcagaacgc agaagcggtc tgataaaaca gaatttgcct    1560
ggcggcagta gcgcggtggt cccacctgac cccatgccga actcagaagt gaaacgccgt    1620
agcgccgatg gtagtgtggg gtctccccat gcgagagtag ggaactgcca ggcatcaaat    1680
aaaacgaaag gctcagtcga aagactgggc ctttcgtttt atctgttgtt tgtcggtgaa    1740
cgctctcctg agtaggacaa atccgccggg agcggatttg aacgttgcga agcaacggcc    1800
cggagggtgg cgggcaggac gcccgccata aactgccagg catcaaatta agcagaaggc    1860
catcctgacg gatggccttt ttgcgtttct acaaactctt ttgtttattt ttctaaatac    1920
attcaaatat gtatccgctc atgagacaat aaccctgata aatgcttcaa taatattgaa    1980
aaaggaagag tatgagtatt caacatttcc gtgtcgccct tattccctttt tttgcggcat   2040 tttgccttcc tgttttttgct cacccagaaa cgctggtgaa agtaaaagat gctgaagatc    2100
agttgggtgc acgagtgggt tacatcgaac tggatctcaa cagcggtaag atccttgaga    2160
gttttcgccc cgaagaacgt tttccaatga tgagcacttt taaagttctg ctatgtggcg    2220
cggtattatc ccgtgttgac gccgggcaag agcaactcgg tcgccgcata cactattctc    2280
agaatgactt ggttgagtac tcaccagtca cagaaaagca tcttacggat ggcatgacag    2340
taagagaatt atgcagtgct gccataacca tgagtgataa cactgcggcc aacttacttc    2400
tgacaacgat cggaggaccg aaggagctaa ccgcttttttt gcacaacatg ggggatcatg    2460
taactcgcct tgatcgttgg gaaccggagc tgaatgaagc cataccaaac gacgagcgtg    2520
acaccacgat gcctgtagca atggcaacaa cgttgcgcaa actattaact ggcgaactac    2580
ttactctagc ttcccggcaa caattaatag actggatgga ggcggataaa gttgcaggac    2640
cacttctgcg ctcggccctt ccggctggct ggtttattgc tgataaatct ggagccggtg    2700
agcgtgggtc tcgcggtatc attgcagcac tggggccaga tggtaagccc tcccgtatcg    2760
tagttatcta cacgacgggg agtcaggcaa ctatggatga acgaaataga cagatcgctg    2820
agataggtgc ctcactgatt aagcattggt aactgtcaga ccaagtttac tcatatatac    2880
tttagattga tttaaaactt catttttaat ttaaaaggat ctaggtgaag atcctttttg    2940
ataatctcat gaccaaaatc ccttaacgtg agttttcgtt ccactgagcg tcagaccccg    3000
tagaaaagat caaaggatct tcttgagatc ctttttttct gcgcgtaatc tgctgcttgc    3060
aaacaaaaaa accaccgcta ccagcggtgg tttgtttgcc ggatcaagag ctaccaactc    3120
tttttccgaa ggtaactggc ttcagcagag cgcagatacc aaatactgtc cttctagtgt    3180
agccgtagtt aggccaccac ttcaagaact ctgtagcacc gcctacatac ctcgctctgc    3240
taatcctgtt accagtggct gctgccagtg gcgataagtc gtgtcttacc gggttggact    3300
caagacgata gttaccggat aaggcgcagc ggtcgggctg aacggggggt tcgtgcacac    3360
agcccagctt ggagcgaacg acctacaccg aactgagata cctacagcgt gagctatgag    3420
aaagcgccac gcttcccgaa gggagaaagg cggacaggta tccggtaagc ggcagggtcg    3480
gaacaggaga gcgcacgagg gagcttccag ggggaaacgc ctggtatctt tatagtcctg    3540
tcgggtttcg ccacctctga cttgagcgtc gatttttgtg atgctcgtca ggggggcgga    3600
```

```
gcctatggaa aaacgccagc aacgcggcct ttttacggtt cctggccttt tgctggcctt    3660
ttgctcacat gttctttcct gcgttatccc ctgattctgt ggataaccgt attaccgcct    3720
ttgagtgagc tgataccgct cgccgcagcc gaacgaccga gcgcagcgag tcagtgagcg    3780
aggaagcgga gagcgcctg atgcggtatt ttctccttac gcatctgtgc ggtatttcac     3840
accgcatata tggtgcactc tcagtacaat ctgctctgat gccgcatagt taagccagta    3900
tacactccgc tatcgctacg tgactgggtc atggctgcgc cccgacaccc gccaacaccc    3960
gctgacgcgc cctgacgggc ttgtctgctc ccggcatccg cttacagaca agctgtgacc    4020
gtctccggga gctgcatgtg tcagaggttt tcaccgtcat caccgaaacg cgcgaggcag    4080
cagatcaatt cgcgcgcgaa ggcgaagcgg catgcataat gtgcctgtca atggacgaa     4140 gcagggattc tgcaaaccct atgctactcc gtcaagccgt caattgtctg attcgttacc    4200
aattatgaca acttgacggc tacatcattc acttttcct cacaaccggc acggaactcg     4260
ctcgggctgg ccccggtgca ttttttaaat acccgcgaga aatagagttg atcgtcaaaa    4320
ccaacattgc gaccgacggt ggcgataggc atccgggtgg tgctcaaaag cagcttcgcc    4380
tggctgatac gttggtcctc gcgccagctt aagacgctaa tccctaactg ctggcggaaa    4440
agatgtgaca gacgcgacgg cgacaagcaa acatgctgtg cgacgctggc gatatcaaaa    4500
ttgctgtctg ccaggtgatc gctgatgtac tgacaagcct cgcgtacccg attatccatc    4560
ggtggatgga gcgactcgtt aatcgcttcc atgcgccgca gtaacaattg ctcaagcaga    4620
tttatcgcca gcagctccga atagcgccct tccccttgcc cggcgttaat gatttgccca    4680
aacaggtcgc tgaaatgcgg ctggtgcgct tcatccgggc gaaagaaccc cgtattggca    4740
aatattgacg gccagttaag ccattcatgc cagtaggcgc gcggacgaaa gtaaacccac    4800
tggtgatacc attcgcgagc ctccggatga cgaccgtagt gatgaatctc tcctggcggg    4860
aacagcaaaa tatcacccgg tcggcaaaca aattctcgtc cctgatttt caccacccc     4920 tgaccgcgaa tggtgagatt gagaatataa cctttcattc ccagcggtcg gtcgataaaa    4980
aaatcgagat aaccgttggc ctcaatcggc gttaaacccg ccaccagatg ggcattaaac    5040
gagtatcccg gcagcagggg atcattttgc gcttcagcca tacttttcat actcccgcca    5100
ttcagag                                                              5107
```

<210> SEQ ID NO 24
<211> LENGTH: 5025
<212> TYPE: DNA
<213> ORGANISM: artificial sequence
<220> FEATURE:
<223> OTHER INFORMATION: plasmid pDCQ502

<400> SEQUENCE: 24

```
agatctcgat cccgcgaaat taatacgact cactataggg agaccacaac ggtttccctc      60
tagaaataat tttgtttaac tttaagaagg agatatacat atgcagcagc gtttccagtg    120
gcagttcgaa cagcagccgc gtggtcagca gcgtttccag tggcagttcg aacagcagcc    180
gcgtggtcag cagcgtttcc agtggcagtt cgaacagcag ccggaaggtc agcagcgttt    240
ccagtggcag ttcgaacagc agggatcttg ctgtccgggc tgttgcggat ccgaccctgg    300
tatcccgtgg tggaacattc gcgcacctct gaatgctggt gctggtattc gtgtggaa      360 catccgtgct cctctgaacg cgggtggctc cggtccgggc tccggtggca acacgagcca    420
actgagcacc ggtggtggca acacttccca gctgtccacc ggcggtccga aaagtaata     480 aggcgcgccg acccagcttt cttgtacaaa gtggttgatt cgaggctgct aacaaagccc    540
```

-continued

```
gaaaggaagc tgagttggct gctgccaccg ctgagcaata actagcataa ccccttgggg    600
cctctaaacg ggtcttgagg ggttttttgc tgaaaggagg aactatatcc ggatatccac    660
aggacgggtg tggtcgccat gatcgcgtag tcgatagtgg ctccaagtag cgaagcgagc    720
aggactgggc ggcggccaaa gcggtcggac agtgctccga aacgggtgc gcatagaaat     780 tgcatcaacg catatagcgc tagcagcacg ccatagtgac tggcgatgct gtcggaatgg    840
acgatatccc gcaagaggcc cggcagtacc ggcataacca agcctatgcc tacagcatcc    900
agggtgacgg tgccgaggat gacgatgagc gcattgttag atttcataca cggtgcctga    960
ctgcgttagc aatttaactg tgataaacta ccgcattaaa gcttatcgat gataagctgt    1020
caaacatgag aattcttgaa gacgaaaggg cctcgtgata cgcctatttt tataggttaa    1080
tgtcatgata ataatggttt cttagacgtc aggtggcact tttcgggaa atgtgcgcgg     1140 aaccctatt tgtttatttt tctaaataca ttcaaatatg tatccgctca tgagacaata    1200
accctgataa atgcttcaat atattgaaa aggaagagt atgagtattc aacatttccg      1260
tgtcgccctt attccttttt tgcggcatt ttgccttcct gttttgctc acccagaaac      1320 gctggtgaaa gtaaagatgc tgaagatca gttgggtgca cgagtgggtt acatcgaact    1380
ggatctcaac agcggtaaga tccttgagag ttttcgcccc gaagaacgtt ttccaatgat   1440
gagcactttt aaagttctgc tatgtggcgc ggtattatcc cgtgttgacg ccgggcaaga   1500
gcaactcggt cgccgcatac actattctca gaatgacttg gttgagtact caccagtcac   1560
agaaaagcat cttacggatg gcatgacagt aagagaatta tgcagtgctg ccataaccat    1620
gagtgataac actgcggcca acttacttct gacaacgatc ggaggaccga aggagctaac    1680
cgcttttttg cacaacatgg gggatcatgt aactcgcctt gatcgttggg aaccggagct   1740
gaatgaagcc ataccaaacg acgagcgtga caccacgatg cctgcagcaa tggcaacaac   1800
gttgcgcaaa ctattaactg gcgaactact tactctagct tcccggcaac aattaataga   1860
ctggatggag gcggataaag ttgcaggacc acttctgcgc tcggcccttc cggctggctg   1920
gtttattgct gataaatctg gagccggtga gcgtgggtct cgcggtatca ttgcagcact   1980
ggggccagat ggtaagccct cccgtatcgt agttatctac acgacgggga gtcaggcaac   2040 tatgatgaa cgaaatagac agatcgctga gataggtgcc tcactgatta agcattggta    2100
actgtcagac caagtttact catatatact ttagattgat ttaaaacttc attttaatt    2160 taaaaggatc taggtgaaga tccttttgga taatctcatg accaaaatcc cttaacgtga   2220
gttttcgttc cactgagcgt cagaccccgt agaaaagatc aaaggatctt cttgagatcc   2280 ttttttctg cgcgtaatct gctgcttgca acaaaaaaa ccaccgctac cagcggtggt     2340
ttgtttgccg gatcaagagc taccaactct ttttccgaag gtaactggct tcagcagagc   2400
gcagatacca aatactgtcc ttctagtgta gccgtagtta ggccaccact tcaagaactc   2460
tgtagcaccg cctacatacc tcgctctgct aatcctgtta ccagtggctg ctgccagtgg   2520
cgataagtcg tgtcttaccg ggttggactc aagacgatag ttaccggata aggcgcagcg   2580
gtcgggctga acggggggtt cgtgcacaca gcccagcttg gagcgaacga cctacaccga   2640
actgagatac ctacagcgtg agctatgaga aagcgccacg cttcccgaag ggagaaaggc   2700
ggacaggtat ccggtaagcg gcagggtcgg aacaggagag cgcacgaggg agcttccagg   2760
gggaaacgcc tggtatcttt atagtcctgt cgggtttcgc cacctctgac ttgagcgtcg   2820
atttttgtga tgctcgtcag gggggcggag cctatggaaa aacgccagca acgcggcctt   2880
```

```
tttacggttc ctggccttt  gctggccttt  tgctcacatg  ttctttcctg  cgttatcccc   2940
tgattctgtg dataaccgta ttaccgcctt  tgagtgagct  gataccgctc  gccgcagccg   3000
aacgaccgag cgcagcgagt cagtgagcga  ggaagcggaa  gagcgcctga  tgcggtattt   3060
tctccttacg catctgtgcg gtatttcaca  ccgcatatat  ggtgcactct  cagtacaatc   3120
tgctctgatg ccgcatagtt aagccagtat  acactccgct  atcgctacgt  gactgggtca   3180
tggctgcgcc ccgacacccg ccaacacccg  ctgacgcgcc  ctgacgggct  tgtctgctcc   3240
cggcatccgc ttacagacaa gctgtgaccg  tctccgggag  ctgcatgtgt  cagaggtttt   3300
caccgtcatc accgaaacgc gcgaggcagc  tgcggtaaag  ctcatcagcg  tggtcgtgaa   3360
gcgattcaca gatgtctgcc tgttcatccg  cgtccagctc  gttgagtttc  tccagaagcg   3420
ttaatgtctg gcttctgata aagcgggcca  tgttaagggc  ggttttttcc  tgtttggtca   3480
ctgatgcctc cgtgtaaggg ggatttctgt  tcatggggt   aatgataccg  atgaaacgag   3540
agaggatgct cacgatacgg gttactgatg  atgaacatgc  ccggttactg  gaacgttgtg   3600
agggtaaaca actggcggta tggatgcggc  gggaccagag  aaaaatcact  cagggtcaat   3660
gccagcgctt cgttaataca gatgtaggtg  ttccacaggg  tagccagcag  catcctgcga   3720
tgcagatccg gaacataatg gtgcagggcg  ctgacttccg  cgtttccaga  ctttacgaaa   3780
cacggaaacc gaagaccatt catgttgttg  ctcaggtcgc  agacgttttg  cagcagcagt   3840
cgcttcacgt tcgctcgcgt atcggtgatt  cattctgcta  accagtaagg  caaccccgcc   3900
agcctagccg gtcctcaac  gacaggagca  cgatcatgcg  cacccgtggc  caggacccaa   3960
cgctgcccga tgcgccgc   gtgcggctgc  tggagatggc  ggacgcgatg  gatatgttct   4020
gccaagggtt ggtttgcgca ttcacagttc  tccgcaagaa  ttgattgct   ccaattcttg   4080
gagtggtgaa tccgttagcg aggtgccgcc  ggcttccatt  caggtcgagg  tggcccggct   4140
ccatgcaccg cgacgcaacg cggggaggca  gacaaggtat  agggcggcgc  ctacaatcca   4200
tgccaacccg ttccatgtgc tcgccgaggc  ggcataaatc  gccgtgacga  tcagcggtcc   4260
agtgatcgaa gttaggctgg taagagccgc  gagcgatcct  tgaagctgtc  cctgatggtc   4320
gtcatctacc tgcctggaca gcatggcctg  caacgcgggc  atcccgatgc  cgccggaagc   4380
gagaagaatc ataatgggga aggccatcca  gcctcgcgtc  gcgaacgcca  gcaagacgta   4440
gcccagcgcg tcggccgcca tgccggcgat  aatggcctgc  ttctcgccga  aacgtttggt   4500
ggcgggacca gtgacgaagg cttgagcgag  ggcgtgcaag  attccgaata  ccgcaagcga   4560
caggccgatc atcgtcgcgc tccagcgaaa  gcggtcctcg  ccgaaaatga  cccagagcgc   4620
tgccggcacc tgtcctacga gttgcatgat  aaagaagaca  gtcataagtg  cggcgacgat   4680
agtcatgccc cgcgcccacc ggaaggagct  gactgggttg  aaggctctca  agggcatcgg   4740
tcgatcgacg ctctcccctta tgcgactcct  gcattaggaa  gcagcccagt  agtaggttga   4800
ggccgttgag caccgccgcc gcaaggaatg  gtgcatgcaa  ggagatggcg  cccaacagtc   4860
ccccggccac ggggcctgcc accatacccc  gccgaaaca   agcgctcatg  agcccgaagt   4920
ggcgagcccg atcttcccca tcggtgatgt  cggcgatata  ggcgccagca  accgcacctg   4980
tggcgccggt gatgccggcc acgatgcgtc  cggcgtagag  gatcg                    5025
```

<210> SEQ ID NO 25
<211> LENGTH: 5836
<212> TYPE: DNA
<213> ORGANISM: artificial sequence
<220> FEATURE:
<223> OTHER INFORMATION: plasmid pDCQ506

<400> SEQUENCE: 25

```
aagaaaccaa ttgtccatat tgcatcagac attgccgtca ctgcgtcttt tactggctct      60
tctcgctaac caaaccggta accccgctta ttaaaagcat tctgtaacaa agcgggacca     120
aagccatgac aaaaacgcgt aacaaaagtg tctataatca cggcagaaaa gtccacattg     180
attatttgca cggcgtcaca ctttgctatg ccatagcatt tttatccata agattagcgg     240
atcttacctg acgcttttta tcgcaactct ctactgtttc tccatacccg ttttttgggc     300
taacaggagg aattacatat gcagcagcgt ttccagtggc agttcgaaca gcagccgcgt     360
ggtcagcagc gtttccagtg cagttcgaaa cagcagccgc gtggtcagca gcgtttccag     420
tggcagttcg aacagcagcc ggaaggtcag cagcgtttcc agtggcagtt cgaacagcag     480
ggatcttgct gtccgggctg ttgcggatcc gaccctggta tcccgtggtg aacattcgc      540
gcacctctga atgctggtgc tggtattccg tggtggaaca tccgtgctcc tctgaacgcg     600
ggtggctccg gtccgggctc cggtggcaac acgagccaac tgagcaccgg tggtggcaac     660
acttcccagc tgtccaccgg cggtccgaaa agtaataag gcgcgccgac ccagctttct     720
tgtacaaagt ggttgattcg aggctgctaa caaagcccga aggaagctg agttggctgc      780
tgccaccgct gagcaataac tagcataacc ccttggggcc tctaaacggg tcttgagggg     840
ttttttgctg aaaggaggaa ctatatccgg atatccacag gacgggtgtg gtcgccatga     900
tcgcgtagtc gatagtggct ccaagtagcg aagcgagcag gactgggcgg cggccaaagc     960
ggtcggacag tgctccgaga acgggtgcgc atagaaattg catcaacgca tatagcgcta    1020
gcagcacgcc atagtgactg gcgatgctgt cggaatggac gatatcccgc aagaggcccg    1080
gcagtaccgg cataaccaag cctatgccta cagcatccag ggtgacggtg ccgaggatga    1140
cgatgagcgc attgttagat ttcatacacg gtgcctgact gcgttagcaa tttaactgtg    1200
ataaactacc gcattaaagc ttgcagtggc ggttttcatg gcttgttatg actgttttt     1260
tggggtacag tctatgcctc gggcatccaa gcagcaagcg cgttacgccg tgggtcgatg    1320
tttgatgtta tggagcagca acgatgttac gcagcagggc agtcgcccta aaacaaagtt    1380
aaacatcatg agggaagcgg tgatcgccga agtatcgact caactatcag aggtagttgg    1440
cgtcatcgag cgccatctcg aaccgacgtt gctggccgta catttgtacg gctccgcagt    1500
ggatggcggc ctgaagccac acagtgatat tgatttgctg gttacggtga ccgtaaggct    1560
tgatgaaaca acgcggcgag cttttgatcaa cgaccttttg gaaacttcgg cttcccctgg    1620
agagagcgag attctccgcg ctgtagaagt caccattgtt gtgcacgacg acatcattcc    1680
gtggcgttat ccagctaagc gcgaactgca atttggagaa tggcagcgca atgacattct    1740
tgcaggtatc ttcgagccag ccacgatcga cattgatctg gctatcttgc tgacaaaagc    1800
aagagaacat agcgttgcct tggtaggtcc agcggcggag gaactctttg atccggttcc    1860
tgaacaggat ctatttgagg cgctaaatga aaccttaacg ctatggaact cgccgcccga    1920
ctgggctggc gatgagcgaa atgtagtgct tacgttgtcc cgcatttggt acagcgcagt    1980
aaccggcaaa atcgcgccga aggatgtcgc tgccgactgg gcaatggagc gcctgccggc    2040
ccagtatcag cccgtcatac ttgaagctag acaggcttat cttggacaag aagaagatcg    2100
cttggcctcg cgcgcagatc agttggaaga atttgtccac tacgtgaaag gcgagatcac    2160
caaggtagtc ggcaaataat gtctaacaat tcgttcaagc ttggctgttt tggcggatga    2220
gagaagattt tcagcctgat acagattaaa tcagaacgca gaagcggtct gataaaacag    2280
```

```
aatttgcctg gcggcagtag cgcggtggtc ccacctgacc ccatgccgaa ctcagaagtg    2340
aaacgccgta gcgccgatgg tagtgtgggg tctccccatg cgagagtagg gaactgccag    2400
gcatcaaata aaacgaaagg ctcagtcgaa agactgggcc tttcgtttta tctgttgttt    2460
gtcggtgaac gctctcctga gtaggacaaa tccgccggga gcggatttga acgttgcgaa    2520
gcaacggccc ggagggtggc gggcaggacg cccgccataa actgccaggc atcaaattaa    2580
gcagaaggcc atcctgacgg atggcctttt tgcgtttcta caaactctt tgtttatttt     2640
tctaaataca ttcaaatatg tatccgctca tgagacaata accctgataa atgcttcaat    2700
aatattgaaa aggaagagt atgagtattc aacatttccg tgtcgccctt attccctttt     2760
ttgcggcatt ttgccttcct gtttttgctc acccagaaac gctggtgaaa gtaaaagatg    2820
ctgaagatca gttgggtgca cgagtgggtt acatcgaact ggatctcaac agcggtaaga    2880
tccttgagag ttttcgcccc gaagaacgtt ttccaatgat gagcactttt aaagttctgc    2940
tatgtggcgc ggtattatcc cgtgttgacg ccgggcaaga gcaactcggt cgccgcatac    3000
actattctca gaatgacttg gttgagtact caccagtcac agaaaagcat cttacggatg    3060
gcatgacagt aagagaatta tgcagtgctg ccataaccat gagtgataac actgcggcca    3120
acttacttct gacaacgatc ggaggaccga aggagctaac cgcttttttg cacaacatgg    3180
gggatcatgt aactcgcctt gatcgttggg aaccggagct gaatgaagcc ataccaaacg    3240
acgagcgtga caccacgatg cctgtagcaa tggcaacaac gttgcgcaaa ctattaactg    3300
gcgaactact tactctagct tcccggcaac aattaataga ctggatggag gcggataaag    3360
ttgcaggacc acttctgcgc tcggcccttc cggctggctg gtttattgct gataaatctg    3420
gagccggtga gcgtgggtct cgcggtatca ttgcagcact ggggccagat ggtaagccct    3480
cccgtatcgt agttatctac acgacgggga gtcaggcaac tatggatgaa cgaaatagac    3540
agatcgctga gataggtgcc tcactgatta agcattggta actgtcagac caagtttact    3600
catatatact ttagattgat ttaaaacttc atttttaatt taaaaggatc taggtgaaga    3660
tcctttttga taatctcatg accaaaatcc cttaacgtga gttttcgttc cactgagcgt    3720
cagaccccgt agaaaagatc aaaggatctt cttgagatcc ttttttctg cgcgtaatct     3780
gctgcttgca acaaaaaaa ccaccgctac cagcggtggt ttgtttgccg gatcaagagc     3840
taccaactct tttccgaag gtaactggct tcagcagagc gcagatacca atactgtcc      3900
ttctagtgta gccgtagtta ggccaccact tcaagaactc tgtagcaccg cctacatacc    3960
tcgctctgct aatcctgtta ccagtggctg ctgccagtgg cgataagtcg tgtcttaccg    4020
ggttggactc aagacgatag ttaccggata aggcgcagcg gtcgggctga acggggggtt    4080
cgtgcacaca gcccagcttg gagcgaacga cctacaccga actgagatac ctacagcgtg    4140
agctatgaga aagcgccacg cttcccgaag ggagaaaggc ggacaggtat ccggtaagcg    4200
gcagggtcgg aacaggagag cgcacgaggg agcttccagg gggaaacgcc tggtatcttt    4260
atagtcctgt cgggtttcgc cacctctgac ttgagcgtcg atttttgtga tgctcgtcag    4320
gggggcggag cctatggaaa aacgccagca acgcggcctt tttacggttc ctggccttt     4380
gctggccttt tgctcacatg ttctttcctg cgttatcccc tgattctgtg ataaccgta     4440
ttaccgcctt tgagtgagct gataccgctc gccgcagccg aacgaccgag cgcagcgagt    4500
cagtgagcga ggaagcggaa gagcgcctga tgcggtattt tctccttacg catctgtgcg    4560
gtatttcaca ccgcatatat ggtgcactct cagtacaatc tgctctgatg ccgcatagtt    4620
aagccagtat acactccgct atcgctacgt gactgggtca tggctgcgcc ccgacacccg    4680
```

```
ccaacacccg ctgacgcgcc ctgacgggct tgtctgctcc cggcatccgc ttacagacaa    4740
gctgtgaccg tctccgggag ctgcatgtgt cagaggtttt caccgtcatc accgaaacgc    4800
gcgaggcagc agatcaattc gcgcgcgaag gcgaagcggc atgcataatg tgcctgtcaa    4860
atggacgaag cagggattct gcaaacccta tgctactccg tcaagccgtc aattgtctga    4920
ttcgttacca attatgacaa cttgacggct acatcattca cttttcttc acaaccggca     4980
cggaactcgc tcgggctggc cccggtgcat tttttaaata cccgcgagaa atagagttga    5040
tcgtcaaaac caacattgcg accgacggtg gcgataggca tccgggtggt gctcaaaagc    5100
agcttcgcct ggctgatacg ttggtcctcg cgccagctta agacgctaat ccctaactgc    5160
tggcggaaaa gatgtgacag acgcgacggc gacaagcaaa catgctgtgc gacgctggcg    5220
atatcaaaat tgctgtctgc caggtgatcg ctgatgtact gacaagcctc gcgtacccga    5280
ttatccatcg gtggatggag cgactcgtta atcgcttcca tgcgccgcag taacaattgc    5340
tcaagcagat ttatcgccag cagctccgaa tagcgccctt ccccttgccc ggcgttaatg    5400
atttgcccaa acaggtcgct gaaatgcggc tggtgcgctt catccgggcg aaagaaccccc   5460
gtattggcaa atattgacgg ccagttaagc cattcatgcc agtaggcgcg cggacgaaag    5520
taaacccact ggtgatacca ttcgcgagcc tccggatgac gaccgtagtg atgaatctct    5580
cctggcggga acagcaaaat atcacccggt cggcaaacaa attctcgtcc ctgattttc     5640
accacccct gaccgcgaat ggtgagattg agaatataac ctttcattcc cagcggtcgg     5700
tcgataaaaa aatcgagata accgttggcc tcaatcggcg ttaaacccgc caccagatgg    5760
gcattaaacg agtatcccgg cagcagggga tcattttgcg cttcagccat acttttcata    5820
ctcccgccat tcagag                                                    5836
```

<210> SEQ ID NO 26
<211> LENGTH: 12
<212> TYPE: PRT
<213> ORGANISM: artificial sequence
<220> FEATURE:
<223> OTHER INFORMATION: hair binding peptide

<400> SEQUENCE: 26

Thr Pro Pro Glu Leu Leu His Gly Asp Pro Arg Ser
1               5                   10

<210> SEQ ID NO 27
<211> LENGTH: 12
<212> TYPE: PRT
<213> ORGANISM: artificial sequence
<220> FEATURE:
<223> OTHER INFORMATION: hair binding peptide

<400> SEQUENCE: 27

Arg Thr Asn Ala Ala Asp His Pro Ala Ala Val Thr
1               5                   10

<210> SEQ ID NO 28
<211> LENGTH: 7
<212> TYPE: PRT
<213> ORGANISM: artificial sequence
<220> FEATURE:
<223> OTHER INFORMATION: hair binding peptide

<400> SEQUENCE: 28

Asp Leu Thr Leu Pro Phe His
1               5

```
<210> SEQ ID NO 29
<211> LENGTH: 12
<212> TYPE: PRT
<213> ORGANISM: artificial sequence
<220> FEATURE:
<223> OTHER INFORMATION: hair and skin binding peptide

<400> SEQUENCE: 29

Lys Arg Gly Arg His Lys Arg Pro Lys Arg His Lys
1               5                   10

<210> SEQ ID NO 30
<211> LENGTH: 7
<212> TYPE: PRT
<213> ORGANISM: artificial sequence
<220> FEATURE:
<223> OTHER INFORMATION: hair and skin binding peptide

<400> SEQUENCE: 30

Arg Leu Leu Arg Leu Leu Arg
1               5

<210> SEQ ID NO 31
<211> LENGTH: 12
<212> TYPE: PRT
<213> ORGANISM: artificial sequence
<220> FEATURE:
<223> OTHER INFORMATION: hair and skin binding peptide

<400> SEQUENCE: 31

His Lys Pro Arg Gly Gly Arg Lys Lys Ala Leu His
1               5                   10

<210> SEQ ID NO 32
<211> LENGTH: 18
<212> TYPE: PRT
<213> ORGANISM: artificial sequence
<220> FEATURE:
<223> OTHER INFORMATION: hair and skin binding peptide

<400> SEQUENCE: 32

Lys Pro Arg Pro Pro His Gly Lys Lys His Arg Pro Lys His Arg Pro
1               5                   10                  15

Lys Lys

<210> SEQ ID NO 33
<211> LENGTH: 18
<212> TYPE: PRT
<213> ORGANISM: artificial sequence
<220> FEATURE:
<223> OTHER INFORMATION: hair and skin binding peptide

<400> SEQUENCE: 33

Arg Gly Arg Pro Lys Lys Gly His Gly Lys Arg Pro Gly His Arg Ala
1               5                   10                  15

Arg Lys

<210> SEQ ID NO 34
<211> LENGTH: 55
<212> TYPE: PRT
<213> ORGANISM: artificial sequence
<220> FEATURE:
<223> OTHER INFORMATION: hair binding peptide

<400> SEQUENCE: 34
```

```
Pro Arg Thr Asn Ala Ala Asp His Pro Ala Ala Val Thr Gly Gly
1               5                   10                  15

Cys Gly Gly Gly Arg Thr Asn Ala Ala Asp His Pro Ala Ala Val Thr
                20                  25                  30

Gly Gly Gly Cys Gly Gly Arg Thr Asn Ala Ala Asp His Pro Ala
            35                  40                  45

Ala Val Thr Gly Gly Gly Cys
        50                  55

<210> SEQ ID NO 35
<211> LENGTH: 50
<212> TYPE: PRT
<213> ORGANISM: artificial sequence
<220> FEATURE:
<223> OTHER INFORMATION: hair binding peptide

<400> SEQUENCE: 35

Pro Arg Thr Asn Ala Ala Asp His Pro Ala Ala Val Thr Gly Gly Gly
1               5                   10                  15

Cys Gly Gly Gly Ile Pro Trp Trp Asn Ile Arg Ala Pro Leu Asn Ala
                20                  25                  30

Gly Gly Gly Cys Gly Gly Gly Asp Leu Thr Leu Pro Phe His Gly Gly
            35                  40                  45

Gly Cys
    50

<210> SEQ ID NO 36
<211> LENGTH: 82
<212> TYPE: PRT
<213> ORGANISM: artificial sequence
<220> FEATURE:
<223> OTHER INFORMATION: hair binding peptide

<400> SEQUENCE: 36

Pro Arg Thr Asn Ala Ala Asp His Pro Gly Gly Gly Thr Pro Pro Glu
1               5                   10                  15

Leu Leu His Gly Asp Pro Arg Ser Lys Cys Gly Gly Gly Arg Thr Asn
                20                  25                  30

Ala Ala Asp His Pro Gly Gly Gly Thr Pro Pro Glu Leu Leu His Gly
            35                  40                  45

Asp Pro Arg Ser Lys Cys Gly Gly Gly Arg Thr Asn Ala Ala Asp His
    50                  55                  60

Pro Gly Gly Gly Thr Pro Pro Glu Leu Leu His Gly Asp Pro Arg Ser
65                  70                  75                  80

Lys Cys

<210> SEQ ID NO 37
<211> LENGTH: 82
<212> TYPE: PRT
<213> ORGANISM: artificial sequence
<220> FEATURE:
<223> OTHER INFORMATION: hair binding peptide

<400> SEQUENCE: 37

Pro Thr Pro Pro Thr Asn Val Leu Met Leu Ala Thr Lys Gly Gly Gly
1               5                   10                  15

Arg Thr Asn Ala Ala Asp His Pro Lys Cys Gly Gly Gly Thr Pro Pro
                20                  25                  30

Thr Asn Val Leu Met Leu Ala Thr Lys Gly Gly Gly Arg Thr Asn Ala
```

```
                35                  40                  45
Ala Asp His Pro Lys Cys Gly Gly Gly Thr Pro Thr Asn Val Leu
 50                  55                  60

Met Leu Ala Thr Lys Gly Gly Gly Arg Thr Asn Ala Ala Asp His Pro
 65                  70                  75                  80

Lys Cys

<210> SEQ ID NO 38
<211> LENGTH: 82
<212> TYPE: PRT
<213> ORGANISM: artificial sequence
<220> FEATURE:
<223> OTHER INFORMATION: hair binding peptide

<400> SEQUENCE: 38

Pro Arg Thr Asn Ala Ala Asp His Pro Gly Gly Gly Thr Pro Pro Thr
 1               5                  10                  15

Asn Val Leu Met Leu Ala Thr Lys Lys Cys Gly Gly Gly Arg Thr Asn
                20                  25                  30

Ala Ala Asp His Pro Gly Gly Gly Thr Pro Pro Thr Asn Val Leu Met
            35                  40                  45

Leu Ala Thr Lys Lys Cys Gly Gly Gly Arg Thr Asn Ala Ala Asp His
 50                  55                  60

Pro Gly Gly Gly Thr Pro Pro Thr Asn Val Leu Met Leu Ala Thr Lys
 65                  70                  75                  80

Lys Cys

<210> SEQ ID NO 39
<211> LENGTH: 13
<212> TYPE: PRT
<213> ORGANISM: artificial sequence
<220> FEATURE:
<223> OTHER INFORMATION: hair binding peptide

<400> SEQUENCE: 39

Thr Pro Pro Glu Leu Leu His Gly Asp Pro Arg Ser Cys
 1               5                  10

<210> SEQ ID NO 40
<211> LENGTH: 12
<212> TYPE: PRT
<213> ORGANISM: artificial sequence
<220> FEATURE:
<223> OTHER INFORMATION: hair binding peptide

<400> SEQUENCE: 40

Glu Gln Ile Ser Gly Ser Leu Val Ala Ala Pro Trp
 1               5                  10

<210> SEQ ID NO 41
<211> LENGTH: 12
<212> TYPE: PRT
<213> ORGANISM: artificial sequence
<220> FEATURE:
<223> OTHER INFORMATION: hair binding peptide

<400> SEQUENCE: 41

Thr Asp Met Gln Ala Pro Thr Lys Ser Tyr Ser Asn
 1               5                  10

<210> SEQ ID NO 42
<211> LENGTH: 12
```

```
<212> TYPE: PRT
<213> ORGANISM: artificial sequence
<220> FEATURE:
<223> OTHER INFORMATION: hair binding peptide

<400> SEQUENCE: 42

Ala Leu Pro Arg Ile Ala Asn Thr Trp Ser Pro Ser
1               5                   10

<210> SEQ ID NO 43
<211> LENGTH: 12
<212> TYPE: PRT
<213> ORGANISM: artificial sequence
<220> FEATURE:
<223> OTHER INFORMATION: hair binding peptide

<400> SEQUENCE: 43

Leu Asp Thr Ser Phe Pro Pro Val Pro Phe His Ala
1               5                   10

<210> SEQ ID NO 44
<211> LENGTH: 12
<212> TYPE: PRT
<213> ORGANISM: artificial sequence
<220> FEATURE:
<223> OTHER INFORMATION: hair binding peptide

<400> SEQUENCE: 44

Thr Pro Pro Thr Asn Val Leu Met Leu Ala Thr Lys
1               5                   10

<210> SEQ ID NO 45
<211> LENGTH: 15
<212> TYPE: PRT
<213> ORGANISM: artificial sequence
<220> FEATURE:
<223> OTHER INFORMATION: hair binding peptide

<400> SEQUENCE: 45

Ser Thr Leu His Lys Tyr Lys Ser Gln Asp Pro Thr Pro His His
1               5                   10                  15

<210> SEQ ID NO 46
<211> LENGTH: 12
<212> TYPE: PRT
<213> ORGANISM: artificial sequence
<220> FEATURE:
<223> OTHER INFORMATION: hair binding peptide

<400> SEQUENCE: 46

Gly Met Pro Ala Met His Trp Ile His Pro Phe Ala
1               5                   10

<210> SEQ ID NO 47
<211> LENGTH: 15
<212> TYPE: PRT
<213> ORGANISM: artificial sequence
<220> FEATURE:
<223> OTHER INFORMATION: hair binding peptide

<400> SEQUENCE: 47

His Asp His Lys Asn Gln Lys Glu Thr His Gln Arg His Ala Ala
1               5                   10                  15

<210> SEQ ID NO 48
<211> LENGTH: 20
<212> TYPE: PRT
```

```
<213> ORGANISM: artificial sequence
<220> FEATURE:
<223> OTHER INFORMATION: hair binding peptide

<400> SEQUENCE: 48

His Asn His Met Gln Glu Arg Tyr Thr Asp Pro Gln His Ser Pro Ser
1               5                   10                  15

Val Asn Gly Leu
            20

<210> SEQ ID NO 49
<211> LENGTH: 20
<212> TYPE: PRT
<213> ORGANISM: artificial sequence
<220> FEATURE:
<223> OTHER INFORMATION: hair binding peptide

<400> SEQUENCE: 49

Thr Ala Glu Ile Gln Ser Ser Lys Asn Pro Asn Pro His Pro Gln Arg
1               5                   10                  15

Ser Trp Thr Asn
            20

<210> SEQ ID NO 50
<211> LENGTH: 12
<212> TYPE: PRT
<213> ORGANISM: artificial sequence
<220> FEATURE:
<223> OTHER INFORMATION: skin binding peptide

<400> SEQUENCE: 50

Thr Pro Phe His Ser Pro Glu Asn Ala Pro Gly Ser
1               5                   10

<210> SEQ ID NO 51
<211> LENGTH: 12
<212> TYPE: PRT
<213> ORGANISM: artificial sequence
<220> FEATURE:
<223> OTHER INFORMATION: skin binding peptide

<400> SEQUENCE: 51

Thr Met Gly Phe Thr Ala Pro Arg Phe Pro His Tyr
1               5                   10

<210> SEQ ID NO 52
<211> LENGTH: 12
<212> TYPE: PRT
<213> ORGANISM: artificial sequence
<220> FEATURE:
<223> OTHER INFORMATION: skin binding peptide

<400> SEQUENCE: 52

Ser Val Ser Val Gly Met Lys Pro Ser Pro Arg Pro
1               5                   10

<210> SEQ ID NO 53
<211> LENGTH: 12
<212> TYPE: PRT
<213> ORGANISM: artificial sequence
<220> FEATURE:
<223> OTHER INFORMATION: skin binding peptide

<400> SEQUENCE: 53

Asn Leu Gln His Ser Val Gly Thr Ser Pro Val Trp
1               5                   10
```

-continued

```
<210> SEQ ID NO 54
<211> LENGTH: 15
<212> TYPE: PRT
<213> ORGANISM: artificial sequence
<220> FEATURE:
<223> OTHER INFORMATION: skin binding peptide

<400> SEQUENCE: 54

Gln Leu Ser Tyr His Ala Tyr Pro Gln Ala Asn His His Ala Pro
 1               5                  10                  15

<210> SEQ ID NO 55
<211> LENGTH: 14
<212> TYPE: PRT
<213> ORGANISM: artificial sequence
<220> FEATURE:
<223> OTHER INFORMATION: skin binding peptide

<400> SEQUENCE: 55

Ser Gly Cys His Leu Val Tyr Asp Asn Gly Phe Cys Asp His
 1               5                  10

<210> SEQ ID NO 56
<211> LENGTH: 14
<212> TYPE: PRT
<213> ORGANISM: artificial sequence
<220> FEATURE:
<223> OTHER INFORMATION: skin binding peptide

<400> SEQUENCE: 56

Ala Ser Cys Pro Ser Ala Ser His Ala Asp Pro Cys Ala His
 1               5                  10

<210> SEQ ID NO 57
<211> LENGTH: 14
<212> TYPE: PRT
<213> ORGANISM: artificial sequence
<220> FEATURE:
<223> OTHER INFORMATION: skin binding peptide

<400> SEQUENCE: 57

Asn Leu Cys Asp Ser Ala Arg Asp Ser Pro Arg Cys Lys Val
 1               5                  10

<210> SEQ ID NO 58
<211> LENGTH: 12
<212> TYPE: PRT
<213> ORGANISM: artificial sequence
<220> FEATURE:
<223> OTHER INFORMATION: skin binding peptide

<400> SEQUENCE: 58

Asn His Ser Asn Trp Lys Thr Ala Ala Asp Phe Leu
 1               5                  10

<210> SEQ ID NO 59
<211> LENGTH: 12
<212> TYPE: PRT
<213> ORGANISM: artificial sequence
<220> FEATURE:
<223> OTHER INFORMATION: skin binding peptide

<400> SEQUENCE: 59

Ser Asp Thr Ile Ser Arg Leu His Val Ser Met Thr
 1               5                  10
```

```
<210> SEQ ID NO 60
<211> LENGTH: 12
<212> TYPE: PRT
<213> ORGANISM: artificial sequence
<220> FEATURE:
<223> OTHER INFORMATION: skin binding peptide

<400> SEQUENCE: 60

Ser Pro Tyr Pro Ser Trp Ser Thr Pro Ala Gly Arg
1               5                   10

<210> SEQ ID NO 61
<211> LENGTH: 14
<212> TYPE: PRT
<213> ORGANISM: artificial sequence
<220> FEATURE:
<223> OTHER INFORMATION: skin binding peptide

<400> SEQUENCE: 61

Asp Ala Cys Ser Gly Asn Gly His Pro Asn Asn Cys Asp Arg
1               5                   10

<210> SEQ ID NO 62
<211> LENGTH: 14
<212> TYPE: PRT
<213> ORGANISM: artificial sequence
<220> FEATURE:
<223> OTHER INFORMATION: skin binding peptide

<400> SEQUENCE: 62

Asp Trp Cys Asp Thr Ile Ile Pro Gly Arg Thr Cys His Gly
1               5                   10

<210> SEQ ID NO 63
<211> LENGTH: 12
<212> TYPE: PRT
<213> ORGANISM: artificial sequence
<220> FEATURE:
<223> OTHER INFORMATION: Nail binding peptide

<400> SEQUENCE: 63

Ala Leu Pro Arg Ile Ala Asn Thr Trp Ser Pro Ser
1               5                   10

<210> SEQ ID NO 64
<211> LENGTH: 12
<212> TYPE: PRT
<213> ORGANISM: artificial sequence
<220> FEATURE:
<223> OTHER INFORMATION: Nail binding peptide

<400> SEQUENCE: 64

Tyr Pro Ser Phe Ser Pro Thr Tyr Arg Pro Ala Phe
1               5                   10

<210> SEQ ID NO 65
<211> LENGTH: 17
<212> TYPE: PRT
<213> ORGANISM: artificial sequence
<220> FEATURE:
<223> OTHER INFORMATION: Antimicrobial peptide

<400> SEQUENCE: 65

Pro Lys Gly Leu Lys Lys Leu Leu Lys Gly Leu Lys Lys Leu Leu Lys
1               5                   10                  15

Leu
```

<210> SEQ ID NO 66
<211> LENGTH: 16
<212> TYPE: PRT
<213> ORGANISM: artificial sequence
<220> FEATURE:
<223> OTHER INFORMATION: Antimicrobial peptide

<400> SEQUENCE: 66

Lys Gly Leu Lys Lys Leu Leu Lys Gly Leu Lys Lys Leu Leu Lys Leu
1               5                   10                  15

<210> SEQ ID NO 67
<211> LENGTH: 16
<212> TYPE: PRT
<213> ORGANISM: artificial sequence
<220> FEATURE:
<223> OTHER INFORMATION: Antimicrobial peptide

<400> SEQUENCE: 67

Lys Gly Leu Lys Lys Leu Leu Lys Leu Leu Lys Lys Leu Leu Lys Leu
1               5                   10                  15

<210> SEQ ID NO 68
<211> LENGTH: 14
<212> TYPE: PRT
<213> ORGANISM: artificial sequence
<220> FEATURE:
<223> OTHER INFORMATION: Antimicrobial peptide

<400> SEQUENCE: 68

Leu Lys Lys Leu Leu Lys Leu Leu Lys Lys Leu Leu Lys Leu
1               5                   10

<210> SEQ ID NO 69
<211> LENGTH: 12
<212> TYPE: PRT
<213> ORGANISM: artificial sequence
<220> FEATURE:
<223> OTHER INFORMATION: Antimicrobial peptide

<400> SEQUENCE: 69

Leu Lys Lys Leu Leu Lys Leu Leu Lys Lys Leu Leu
1               5                   10

<210> SEQ ID NO 70
<211> LENGTH: 17
<212> TYPE: PRT
<213> ORGANISM: artificial sequence
<220> FEATURE:
<223> OTHER INFORMATION: Antimicrobial peptide

<400> SEQUENCE: 70

Val Ala Lys Lys Leu Ala Lys Leu Ala Lys Lys Leu Ala Lys Leu Ala
1               5                   10                  15

Leu

<210> SEQ ID NO 71
<211> LENGTH: 13
<212> TYPE: PRT
<213> ORGANISM: artificial sequence
<220> FEATURE:
<223> OTHER INFORMATION: Antimicrobial peptide

<400> SEQUENCE: 71

Phe Ala Lys Leu Leu Ala Lys Ala Leu Lys Lys Leu Leu

-continued

```
<210> SEQ ID NO 72
<211> LENGTH: 16
<212> TYPE: PRT
<213> ORGANISM: artificial sequence
<220> FEATURE:
<223> OTHER INFORMATION: Antimicrobial peptide

<400> SEQUENCE: 72

Lys Gly Leu Lys Lys Gly Leu Lys Leu Leu Lys Lys Leu Leu Lys Leu
1               5                   10                  15

<210> SEQ ID NO 73
<211> LENGTH: 16
<212> TYPE: PRT
<213> ORGANISM: artificial sequence
<220> FEATURE:
<223> OTHER INFORMATION: Antimicrobial peptide

<400> SEQUENCE: 73

Lys Gly Leu Lys Lys Leu Leu Lys Leu Gly Lys Lys Leu Leu Lys Leu
1               5                   10                  15

<210> SEQ ID NO 74
<211> LENGTH: 16
<212> TYPE: PRT
<213> ORGANISM: artificial sequence
<220> FEATURE:
<223> OTHER INFORMATION: Antimicrobial peptide

<400> SEQUENCE: 74

Lys Gly Leu Lys Lys Leu Gly Lys Leu Leu Lys Lys Leu Leu Lys Leu
1               5                   10                  15

<210> SEQ ID NO 75
<211> LENGTH: 16
<212> TYPE: PRT
<213> ORGANISM: artificial sequence
<220> FEATURE:
<223> OTHER INFORMATION: Antimicrobial peptide

<400> SEQUENCE: 75

Lys Gly Leu Lys Lys Leu Leu Lys Leu Leu Lys Lys Gly Leu Lys Leu
1               5                   10                  15

<210> SEQ ID NO 76
<211> LENGTH: 16
<212> TYPE: PRT
<213> ORGANISM: artificial sequence
<220> FEATURE:
<223> OTHER INFORMATION: Antimicrobial peptide

<400> SEQUENCE: 76

Lys Gly Leu Lys Lys Leu Leu Lys Leu Leu Lys Leu Gly Lys Lys Leu
1               5                   10                  15

<210> SEQ ID NO 77
<211> LENGTH: 19
<212> TYPE: PRT
<213> ORGANISM: artificial sequence
<220> FEATURE:
<223> OTHER INFORMATION: Antimicrobial peptide

<400> SEQUENCE: 77

Phe Ala Leu Ala Leu Lys Ala Leu Lys Lys Leu Lys Lys Ala Leu Lys
1               5                   10                  15
```

Lys Ala Leu

<210> SEQ ID NO 78
<211> LENGTH: 17
<212> TYPE: PRT
<213> ORGANISM: artificial sequence
<220> FEATURE:
<223> OTHER INFORMATION: Antimicrobial peptide

<400> SEQUENCE: 78

Phe Ala Lys Lys Leu Ala Lys Leu Ala Lys Lys Leu Ala Lys Leu Ala
1               5                   10                  15

Leu

<210> SEQ ID NO 79
<211> LENGTH: 13
<212> TYPE: PRT
<213> ORGANISM: artificial sequence
<220> FEATURE:
<223> OTHER INFORMATION: Antimicrobial peptide

<400> SEQUENCE: 79

Phe Ala Lys Leu Leu Ala Lys Leu Ala Lys Lys Leu Leu
1               5                   10

<210> SEQ ID NO 80
<211> LENGTH: 15
<212> TYPE: PRT
<213> ORGANISM: artificial sequence
<220> FEATURE:
<223> OTHER INFORMATION: Antimicrobial peptide

<400> SEQUENCE: 80

Phe Ala Lys Lys Leu Ala Lys Leu Ala Leu Lys Leu Ala Lys Leu
1               5                   10                  15

<210> SEQ ID NO 81
<211> LENGTH: 10
<212> TYPE: PRT
<213> ORGANISM: artificial sequence
<220> FEATURE:
<223> OTHER INFORMATION: Antimicrobial peptide

<400> SEQUENCE: 81

Phe Ala Lys Lys Leu Ala Lys Lys Leu Leu
1               5                   10

<210> SEQ ID NO 82
<211> LENGTH: 13
<212> TYPE: PRT
<213> ORGANISM: artificial sequence
<220> FEATURE:
<223> OTHER INFORMATION: Antimicrobial peptide

<400> SEQUENCE: 82

Phe Ala Lys Leu Leu Ala Lys Leu Ala Lys Lys Val Leu
1               5                   10

<210> SEQ ID NO 83
<211> LENGTH: 13
<212> TYPE: PRT
<213> ORGANISM: artificial sequence
<220> FEATURE:
<223> OTHER INFORMATION: Antimicrobial peptide

<400> SEQUENCE: 83

```
Lys Tyr Lys Lys Ala Leu Lys Lys Leu Ala Lys Leu Leu
1               5                   10
```

<210> SEQ ID NO 84
<211> LENGTH: 12
<212> TYPE: PRT
<213> ORGANISM: artificial sequence
<220> FEATURE:
<223> OTHER INFORMATION: Antimicrobial peptide

<400> SEQUENCE: 84

```
Phe Ala Leu Leu Lys Ala Leu Leu Lys Lys Ala Leu
1               5                   10
```

<210> SEQ ID NO 85
<211> LENGTH: 14
<212> TYPE: PRT
<213> ORGANISM: artificial sequence
<220> FEATURE:
<223> OTHER INFORMATION: Antimicrobial peptide

<400> SEQUENCE: 85

```
Lys Arg Leu Phe Lys Lys Leu Lys Phe Ser Leu Arg Lys Tyr
1               5                   10
```

<210> SEQ ID NO 86
<211> LENGTH: 14
<212> TYPE: PRT
<213> ORGANISM: artificial sequence
<220> FEATURE:
<223> OTHER INFORMATION: Antimicrobial peptide

<400> SEQUENCE: 86

```
Lys Arg Leu Phe Lys Lys Leu Leu Phe Ser Leu Arg Lys Tyr
1               5                   10
```

<210> SEQ ID NO 87
<211> LENGTH: 14
<212> TYPE: PRT
<213> ORGANISM: artificial sequence
<220> FEATURE:
<223> OTHER INFORMATION: Antimicrobial peptide

<400> SEQUENCE: 87

```
Leu Leu Leu Phe Leu Leu Lys Lys Arg Lys Lys Arg Lys Tyr
1               5                   10
```

<210> SEQ ID NO 88
<211> LENGTH: 36
<212> TYPE: PRT
<213> ORGANISM: Hyalophora cecropia

<400> SEQUENCE: 88

```
Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Trp Gly Gln Ala Thr
            20                  25                  30

Gln Ile Ala Lys
        35
```

<210> SEQ ID NO 89
<211> LENGTH: 23
<212> TYPE: PRT
<213> ORGANISM: Xenopus sp.

```
<400> SEQUENCE: 89

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 90
<211> LENGTH: 22
<212> TYPE: PRT
<213> ORGANISM: Xenopus sp.

<400> SEQUENCE: 90

Gly Ile Gly Lys Phe Leu Lys Lys Ala Lys Lys Phe Gly Lys Ala Phe
1               5                   10                  15

Val Lys Ile Leu Lys Lys
            20

<210> SEQ ID NO 91
<211> LENGTH: 12
<212> TYPE: PRT
<213> ORGANISM: Bos Taurus

<400> SEQUENCE: 91

Arg Leu Cys Arg Ile Val Val Ile Arg Val Cys Arg
1               5                   10

<210> SEQ ID NO 92
<211> LENGTH: 13
<212> TYPE: PRT
<213> ORGANISM: Bos sp.

<400> SEQUENCE: 92

Ile Leu Pro Trp Lys Trp Pro Trp Trp Pro Trp Arg Arg
1               5                   10

<210> SEQ ID NO 93
<211> LENGTH: 24
<212> TYPE: PRT
<213> ORGANISM: Homo sapiens

<400> SEQUENCE: 93

Asp Ser His Ala Lys Arg His His Gly Tyr Lys Arg Lys Phe His Glu
1               5                   10                  15

Lys His His Ser His Arg Gly Tyr
            20

<210> SEQ ID NO 94
<211> LENGTH: 7
<212> TYPE: PRT
<213> ORGANISM: artificial sequence
<220> FEATURE:
<223> OTHER INFORMATION: Carbon black binding peptide

<400> SEQUENCE: 94

Met Pro Pro Pro Leu Met Gln
1               5

<210> SEQ ID NO 95
<211> LENGTH: 7
<212> TYPE: PRT
<213> ORGANISM: artificial sequence
<220> FEATURE:
<223> OTHER INFORMATION: Carbon black binding peptide
```

-continued

```
<400> SEQUENCE: 95

Phe His Glu Asn Trp Pro Ser
1               5

<210> SEQ ID NO 96
<211> LENGTH: 12
<212> TYPE: PRT
<213> ORGANISM: artificial sequence
<220> FEATURE:
<223> OTHER INFORMATION: Carbon black binding peptide

<400> SEQUENCE: 96

Arg Thr Ala Pro Thr Thr Pro Leu Leu Leu Ser Leu
1               5                   10

<210> SEQ ID NO 97
<211> LENGTH: 12
<212> TYPE: PRT
<213> ORGANISM: artificial sequence
<220> FEATURE:
<223> OTHER INFORMATION: Carbon black binding peptide

<400> SEQUENCE: 97

Trp His Leu Ser Trp Ser Pro Val Pro Leu Pro Thr
1               5                   10

<210> SEQ ID NO 98
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 98

Pro His Ala Arg Leu Val Gly
1               5

<210> SEQ ID NO 99
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 99

Asn Ile Pro Tyr His His Pro
1               5

<210> SEQ ID NO 100
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 100

Thr Thr Met Pro Ala Ile Pro
1               5

<210> SEQ ID NO 101
<211> LENGTH: 7
<212> TYPE: PRT
<213> ORGANISM: artificial sequence
<220> FEATURE:
<223> OTHER INFORMATION: Cromophtal Yellow binding peptide

<400> SEQUENCE: 101
```

His Asn Leu Pro Pro Arg Ser
1               5

<210> SEQ ID NO 102
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 102

Ala His Lys Thr Gln Met Gly Val Arg Gln Pro Ala
1               5                   10

<210> SEQ ID NO 103
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 103

Ala Asp Asn Val Gln Met Gly Val Ser His Thr Pro
1               5                   10

<210> SEQ ID NO 104
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 104

Ala His Asn Ala Gln Met Gly Val Ser His Pro Pro
1               5                   10

<210> SEQ ID NO 105
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 105

Ala Asp Tyr Val Gly Met Gly Val Ser His Arg Pro
1               5                   10

<210> SEQ ID NO 106
<211> LENGTH: 12
<212> TYPE: PRT
<213> ORGANISM: artificial sequence
<220> FEATURE:
<223> OTHER INFORMATION: Cromophtal Yellow binding peptide

<400> SEQUENCE: 106

Ser Val Ser Val Gly Met Lys Pro Ser Pro Arg Pro
1               5                   10

<210> SEQ ID NO 107
<211> LENGTH: 7
<212> TYPE: PRT
<213> ORGANISM: artificial sequence
<220> FEATURE:
<223> OTHER INFORMATION: Sunfast Magenta binding peptide

<400> SEQUENCE: 107

-continued

Tyr Pro Asn Thr Ala Leu Val
1               5

<210> SEQ ID NO 108
<211> LENGTH: 7
<212> TYPE: PRT
<213> ORGANISM: artificial sequence
<220> FEATURE:
<223> OTHER INFORMATION: Sunfast Magenta binding peptide

<400> SEQUENCE: 108

Val Ala Thr Arg Ile Val Ser
1               5

<210> SEQ ID NO 109
<211> LENGTH: 12
<212> TYPE: PRT
<213> ORGANISM: artificial sequence
<220> FEATURE:
<223> OTHER INFORMATION: Sunfast Magenta binding peptide

<400> SEQUENCE: 109

His Ser Leu Lys Asn Ser Met Leu Thr Val Met Ala
1               5                   10

<210> SEQ ID NO 110
<211> LENGTH: 7
<212> TYPE: PRT
<213> ORGANISM: artificial sequence
<220> FEATURE:
<223> OTHER INFORMATION: Sunfast Blue binding peptide

<400> SEQUENCE: 110

Asn Tyr Pro Thr Gln Ala Pro
1               5

<210> SEQ ID NO 111
<211> LENGTH: 7
<212> TYPE: PRT
<213> ORGANISM: artificial sequence
<220> FEATURE:
<223> OTHER INFORMATION: Sunfast Blue binding peptide

<400> SEQUENCE: 111

Lys Cys Cys Tyr Ser Val Gly
1               5

<210> SEQ ID NO 112
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 112

Arg His Asp Leu Asn Thr Trp Leu Pro Pro Val Lys
1               5                   10

<210> SEQ ID NO 113
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 113

Glu Ile Ser Leu Pro Ala Lys Leu Pro Ser Ala Ser

-continued

```
1               5                   10

<210> SEQ ID NO 114
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 114

Ser Val Ser Val Gly Met Lys Pro Ser Pro Arg Pro
1               5                   10

<210> SEQ ID NO 115
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 115

Ser Asp Tyr Val Gly Met Arg Pro Ser Pro Arg His
1               5                   10

<210> SEQ ID NO 116
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 116

Ser Asp Tyr Val Gly Met Arg Leu Ser Pro Ser Gln
1               5                   10

<210> SEQ ID NO 117
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 117

Ser Val Ser Val Gly Ile Gln Pro Ser Pro Arg Pro
1               5                   10

<210> SEQ ID NO 118
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 118

Tyr Val Ser Val Gly Ile Lys Pro Ser Pro Arg Pro
1               5                   10

<210> SEQ ID NO 119
<211> LENGTH: 12
<212> TYPE: PRT
<213> ORGANISM: artificial sequence
<220> FEATURE:
<223> OTHER INFORMATION: Sunfast Blue binding peptide

<400> SEQUENCE: 119

Tyr Val Cys Glu Gly Ile His Pro Cys Pro Arg Pro
1               5                   10
```

<210> SEQ ID NO 120
<211> LENGTH: 7
<212> TYPE: PRT
<213> ORGANISM: artificial sequence
<220> FEATURE:
<223> OTHER INFORMATION: Cellulose binding peptide

<400> SEQUENCE: 120

Val Pro Arg Val Thr Ser Ile
1               5

<210> SEQ ID NO 121
<211> LENGTH: 7
<212> TYPE: PRT
<213> ORGANISM: artificial sequence
<220> FEATURE:
<223> OTHER INFORMATION: Cellulose binding peptide

<400> SEQUENCE: 121

Met Ala Asn His Asn Leu Ser
1               5

<210> SEQ ID NO 122
<211> LENGTH: 7
<212> TYPE: PRT
<213> ORGANISM: artificial sequence
<220> FEATURE:
<223> OTHER INFORMATION: Cellulose binding peptide

<400> SEQUENCE: 122

Phe His Glu Asn Trp Pro Ser
1               5

<210> SEQ ID NO 123
<211> LENGTH: 12
<212> TYPE: PRT
<213> ORGANISM: artificial sequence
<220> FEATURE:
<223> OTHER INFORMATION: Cellulose binding peptide

<400> SEQUENCE: 123

Thr His Lys Thr Ser Thr Gln Arg Leu Leu Ala Ala
1               5                   10

<210> SEQ ID NO 124
<211> LENGTH: 12
<212> TYPE: PRT
<213> ORGANISM: artificial sequence
<220> FEATURE:
<223> OTHER INFORMATION: Cellulose binding peptide

<400> SEQUENCE: 124

Lys Cys Cys Tyr Val Asn Val Gly Ser Val Phe Ser
1               5                   10

<210> SEQ ID NO 125
<211> LENGTH: 12
<212> TYPE: PRT
<213> ORGANISM: artificial sequence
<220> FEATURE:
<223> OTHER INFORMATION: Cellulose binding peptide

<400> SEQUENCE: 125

Ala His Met Gln Phe Arg Thr Ser Leu Thr Pro His
1               5                   10

```
<210> SEQ ID NO 126
<211> LENGTH: 12
<212> TYPE: PRT
<213> ORGANISM: artificial sequence
<220> FEATURE:
<223> OTHER INFORMATION: Poly(ethylene terephthalate) binding peptide

<400> SEQUENCE: 126

Gly Thr Ser Asp His Met Ile Met Pro Phe Phe Asn
1               5                   10

<210> SEQ ID NO 127
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 127

Ile Pro Trp Trp Asn Ile Arg Ala Pro Leu Asn Ala
1               5                   10

<210> SEQ ID NO 128
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 128

Thr Ala Val Met Asn Val Val Asn Asn Gln Leu Ser
1               5                   10

<210> SEQ ID NO 129
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 129

Val Pro Trp Trp Ala Pro Ser Lys Leu Ser Met Gln
1               5                   10

<210> SEQ ID NO 130
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 130

Met Val Met Ala Pro His Thr Pro Arg Ala Arg Ser
1               5                   10

<210> SEQ ID NO 131
<211> LENGTH: 12
<212> TYPE: PRT
<213> ORGANISM: artificial sequence
<220> FEATURE:
<223> OTHER INFORMATION: Poly(methyl methacrylate) binding peptide

<400> SEQUENCE: 131

Thr Tyr Pro Asn Trp Ala His Leu Leu Ser His Tyr
1               5                   10
```

```
<210> SEQ ID NO 132
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 132

Thr Pro Trp Trp Arg Ile Thr
1               5

<210> SEQ ID NO 133
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 133

Asp Leu Thr Leu Pro Phe His
1               5

<210> SEQ ID NO 134
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 134

Gly Thr Ser Ile Pro Ala Met
1               5

<210> SEQ ID NO 135
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 135

His His Lys His Val Val Ala
1               5

<210> SEQ ID NO 136
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 136

His His His Lys His Phe Met
1               5

<210> SEQ ID NO 137
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 137

His His His Arg His Gln Gly
1               5

<210> SEQ ID NO 138
```

```
<211> LENGTH: 7
<212> TYPE: PRT
<213> ORGANISM: artificial sequence
<220> FEATURE:
<223> OTHER INFORMATION: Poly(methyl methacrylate) binding peptide

<400> SEQUENCE: 138

His His Trp His Ala Pro Arg
1               5

<210> SEQ ID NO 139
<211> LENGTH: 7
<212> TYPE: PRT
<213> ORGANISM: artificial sequence
<220> FEATURE:
<223> OTHER INFORMATION: Nylon binding peptide

<400> SEQUENCE: 139

Lys Thr Pro Pro Thr Arg Pro
1               5

<210> SEQ ID NO 140
<211> LENGTH: 7
<212> TYPE: PRT
<213> ORGANISM: artificial sequence
<220> FEATURE:
<223> OTHER INFORMATION: Nylon binding peptide

<400> SEQUENCE: 140

Val Ile Asn Pro Asn Leu Asp
1               5

<210> SEQ ID NO 141
<211> LENGTH: 7
<212> TYPE: PRT
<213> ORGANISM: artificial sequence
<220> FEATURE:
<223> OTHER INFORMATION: Nylon binding peptide

<400> SEQUENCE: 141

Lys Val Trp Ile Val Ser Thr
1               5

<210> SEQ ID NO 142
<211> LENGTH: 7
<212> TYPE: PRT
<213> ORGANISM: artificial sequence
<220> FEATURE:
<223> OTHER INFORMATION: Nylon binding peptide

<400> SEQUENCE: 142

Ala Glu Pro Val Ala Met Leu
1               5

<210> SEQ ID NO 143
<211> LENGTH: 7
<212> TYPE: PRT
<213> ORGANISM: artificial sequence
<220> FEATURE:
<223> OTHER INFORMATION: Nylon binding peptide

<400> SEQUENCE: 143

Ala Glu Leu Val Ala Met Leu
1               5

<210> SEQ ID NO 144
<211> LENGTH: 7
```

<212> TYPE: PRT
<213> ORGANISM: artificial sequence
<220> FEATURE:
<223> OTHER INFORMATION: Nylon binding peptide

<400> SEQUENCE: 144

His Ser Leu Arg Leu Asp Trp
1               5

<210> SEQ ID NO 145
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 145

Glu Ser Ser Tyr Ser Trp Ser Pro Ala Arg Leu Ser
1               5                   10

<210> SEQ ID NO 146
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 146

Gly Pro Leu Lys Leu Leu His Ala Trp Trp Gln Pro
1               5                   10

<210> SEQ ID NO 147
<211> LENGTH: 7
<212> TYPE: PRT
<213> ORGANISM: artificial sequence
<220> FEATURE:
<223> OTHER INFORMATION: Poly(tetrafluoroethylene) binding peptide

<400> SEQUENCE: 147

Asn Ala Leu Thr Arg Pro Val
1               5

<210> SEQ ID NO 148
<211> LENGTH: 7
<212> TYPE: PRT
<213> ORGANISM: artificial sequence
<220> FEATURE:
<223> OTHER INFORMATION: Poly(tetrafluoroethylene) binding peptide

<400> SEQUENCE: 148

Ser Ala Pro Ser Ser Lys Asn
1               5

<210> SEQ ID NO 149
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 149

Ser Val Ser Val Gly Met Lys Pro Ser Pro Arg Pro
1               5                   10

<210> SEQ ID NO 150
<211> LENGTH: 12
<212> TYPE: PRT

```
<213> ORGANISM: artificial sequence
<220> FEATURE:
<223> OTHER INFORMATION: Poly(tetrafluoroethylene) binding peptide

<400> SEQUENCE: 150

Ser Tyr Tyr Ser Leu Pro Pro Ile Phe His Ile Pro
1               5                   10

<210> SEQ ID NO 151
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 151

Thr Phe Thr Pro Tyr Ser Ile Thr His Ala Leu Leu
1               5                   10

<210> SEQ ID NO 152
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 152

Thr Met Gly Phe Thr Ala Pro Arg Phe Pro His Tyr
1               5                   10

<210> SEQ ID NO 153
<211> LENGTH: 12
<212> TYPE: PRT
<213> ORGANISM: artificial sequence
<220> FEATURE:
<223> OTHER INFORMATION: Poly(tetrafluoroethylene) binding peptide

<400> SEQUENCE: 153

Thr Asn Pro Phe Pro Pro Pro Ser Ser Pro Ala
1               5                   10

<210> SEQ ID NO 154
<211> LENGTH: 27
<212> TYPE: PRT
<213> ORGANISM: artificial sequence
<220> FEATURE:
<223> OTHER INFORMATION: clay binding peptide

<400> SEQUENCE: 154

Gly His Gly Ser Pro Ser Asn Ser His His Gly Ser Lys Lys Cys Asp
1               5                   10                  15

Met Gly Asn Ser Arg Ala Lys Cys Lys Arg Leu
            20                  25

<210> SEQ ID NO 155
<211> LENGTH: 27
<212> TYPE: PRT
<213> ORGANISM: artificial sequence
<220> FEATURE:
<223> OTHER INFORMATION: clay binding peptide

<400> SEQUENCE: 155

Ser Asp Arg His Asn Leu Arg Asn Ser Trp Ser Ile Ser Arg His Cys
1               5                   10                  15

Arg Arg Lys Gln Gly Arg Cys Leu Pro Ala His
            20                  25
```

```
<210> SEQ ID NO 156
<211> LENGTH: 27
<212> TYPE: PRT
<213> ORGANISM: artificial sequence
<220> FEATURE:
<223> OTHER INFORMATION: clay binding peptide

<400> SEQUENCE: 156

Lys Lys Ser Asn Lys Gly His His Pro Ser Ser Lys Gly Lys Gly Pro
1               5                   10                  15

Pro Trp Ser Glu Trp Asp Lys Lys Asn Gly Pro
            20                  25

<210> SEQ ID NO 157
<211> LENGTH: 27
<212> TYPE: PRT
<213> ORGANISM: artificial sequence
<220> FEATURE:
<223> OTHER INFORMATION: clay binding peptide

<400> SEQUENCE: 157

Lys Lys Ser Asn Lys Gly Pro His Pro Ser Ser Lys Gly Lys Gly Pro
1               5                   10                  15

Pro Trp Ser Glu Trp Asp Lys Lys Asn Gly Pro
            20                  25

<210> SEQ ID NO 158
<211> LENGTH: 22
<212> TYPE: PRT
<213> ORGANISM: artificial sequence
<220> FEATURE:
<223> OTHER INFORMATION: clay binding peptide

<400> SEQUENCE: 158

Val Gly Arg His His Ser Lys Ala Lys Gln Lys Arg Pro His Gly Gly
1               5                   10                  15

Lys Gly Gln Asn Lys Asn
            20

<210> SEQ ID NO 159
<211> LENGTH: 22
<212> TYPE: PRT
<213> ORGANISM: artificial sequence
<220> FEATURE:
<223> OTHER INFORMATION: clay binding peptide

<400> SEQUENCE: 159

Val Gly Arg His His Pro Lys Ala Lys Gln Lys Arg Pro His Gly Gly
1               5                   10                  15

Lys Gly Gln Asn Lys Asn
            20

<210> SEQ ID NO 160
<211> LENGTH: 17
<212> TYPE: PRT
<213> ORGANISM: artificial sequence
<220> FEATURE:
<223> OTHER INFORMATION: clay binding peptide

<400> SEQUENCE: 160

Gly Arg Arg Pro Arg Ala Arg Gly Arg Ser Arg Arg Gly Ser Thr Lys
1               5                   10                  15

Thr
```

```
<210> SEQ ID NO 161
<211> LENGTH: 19
<212> TYPE: PRT
<213> ORGANISM: artificial sequence
<220> FEATURE:
<223> OTHER INFORMATION: clay binding peptide

<400> SEQUENCE: 161

Leu Gly Val Ile Arg Asn His Val Val Arg Gly Arg Arg His His Gln
1               5                   10                  15

His Val Arg

<210> SEQ ID NO 162
<211> LENGTH: 27
<212> TYPE: PRT
<213> ORGANISM: artificial sequence
<220> FEATURE:
<223> OTHER INFORMATION: clay binding peptide

<400> SEQUENCE: 162

Gln Pro Gly Arg Pro Thr Glu Val His Pro Glu Leu Val Arg Lys Ser
1               5                   10                  15

Ala Tyr Leu Val Asn Pro Ser Glu Asp Ile Arg
            20                  25

<210> SEQ ID NO 163
<211> LENGTH: 27
<212> TYPE: PRT
<213> ORGANISM: artificial sequence
<220> FEATURE:
<223> OTHER INFORMATION: clay binding peptide

<400> SEQUENCE: 163

His Arg Ser Glu Lys Pro Lys Asn Val Lys Tyr Lys Arg Gly Tyr Trp
1               5                   10                  15

Glu Arg Gly Asn Gln Lys Lys His Gly Pro Gly
            20                  25

<210> SEQ ID NO 164
<211> LENGTH: 27
<212> TYPE: PRT
<213> ORGANISM: artificial sequence
<220> FEATURE:
<223> OTHER INFORMATION: clay binding peptide

<400> SEQUENCE: 164

Gly Ser His Lys Arg Arg Gly Ser Tyr Ala Leu Leu Arg Thr Arg Gly
1               5                   10                  15

Val Gly Arg Gln Ala Glu Leu Glu His Leu Leu
            20                  25

<210> SEQ ID NO 165
<211> LENGTH: 27
<212> TYPE: PRT
<213> ORGANISM: artificial sequence
<220> FEATURE:
<223> OTHER INFORMATION: clay binding peptide

<400> SEQUENCE: 165

Val Gly Glu Lys Pro Arg Arg Lys Ser Lys Gly Ala Lys Ala Lys Lys
1               5                   10                  15

Ala Arg Thr Lys Glu Glu Lys Leu Pro Lys Asn
            20                  25
```

<210> SEQ ID NO 166
<211> LENGTH: 27
<212> TYPE: PRT
<213> ORGANISM: artificial sequence
<220> FEATURE:
<223> OTHER INFORMATION: clay binding peptide

<400> SEQUENCE: 166

Asn Lys Gly His Lys Gln Ser Gly Ser Pro Arg His Ser Asn Lys Lys
1               5                   10                  15

Glu Lys Lys Thr Gln Gln Lys Arg Gly Gln Pro
            20                  25

<210> SEQ ID NO 167
<211> LENGTH: 27
<212> TYPE: PRT
<213> ORGANISM: artificial sequence
<220> FEATURE:
<223> OTHER INFORMATION: clay binding peptide

<400> SEQUENCE: 167

His Trp Gly Ser Gln His Lys Thr Gly Leu Arg Asn His Lys Arg Ser
1               5                   10                  15

Arg Arg Asp Ser Leu Gly Lys Arg Gly Thr Asp
            20                  25

<210> SEQ ID NO 168
<211> LENGTH: 27
<212> TYPE: PRT
<213> ORGANISM: artificial sequence
<220> FEATURE:
<223> OTHER INFORMATION: clay binding peptide

<400> SEQUENCE: 168

Lys Gly Trp Gly Ser Ser Ser Gly Pro Pro Gly Leu Thr Gly Lys Ala
1               5                   10                  15

Leu Gly Lys Gly Arg Leu Lys Pro Lys Lys Lys
            20                  25

<210> SEQ ID NO 169
<211> LENGTH: 24
<212> TYPE: PRT
<213> ORGANISM: artificial sequence
<220> FEATURE:
<223> OTHER INFORMATION: clay binding peptide

<400> SEQUENCE: 169

Ser Ser Lys Ser Gly Ala Pro Phe Arg Val Pro Ile Cys Phe Thr Ala
1               5                   10                  15

Pro Arg Pro Gln Lys Thr Leu Gly
            20

<210> SEQ ID NO 170
<211> LENGTH: 5
<212> TYPE: PRT
<213> ORGANISM: artificial sequence
<220> FEATURE:
<223> OTHER INFORMATION: Caspase-3 cleavage sequence
<220> FEATURE:
<221> NAME/KEY: MISC_FEATURE
<222> LOCATION: (5)..(5)
<223> OTHER INFORMATION: Xaa = any amino acid but Pro, Glu, Asp, Gln,
      Lys, and Arg

<400> SEQUENCE: 170

```
Asp Met Gln Asp Xaa
1               5

<210> SEQ ID NO 171
<211> LENGTH: 22
<212> TYPE: PRT
<213> ORGANISM: artificial sequence
<220> FEATURE:
<223> OTHER INFORMATION: Inclusion body tag IBT-3

<400> SEQUENCE: 171

Ser Arg Arg Pro Arg Gln Leu Gln Gln Arg Gln Ser Arg Arg Pro Arg
1               5                   10                  15

Gln Leu Gln Gln Arg Gln
            20

<210> SEQ ID NO 172
<211> LENGTH: 18
<212> TYPE: PRT
<213> ORGANISM: artificial sequence
<220> FEATURE:
<223> OTHER INFORMATION: Inclusion body tag IBT-4

<400> SEQUENCE: 172

Ser Arg Arg Pro Arg Gln Leu Gln Gln Arg Gln His His Gln Gln Gln
1               5                   10                  15

Gln Glu

<210> SEQ ID NO 173
<211> LENGTH: 33
<212> TYPE: PRT
<213> ORGANISM: artificial sequence
<220> FEATURE:
<223> OTHER INFORMATION: Inclusion body tag IBT-23

<400> SEQUENCE: 173

Ser Arg Arg Pro Arg Gln Leu Gln Gln Arg Gln Ser Arg Arg Pro Arg
1               5                   10                  15

Gln Leu Gln Gln Arg Gln Ser Arg Arg Pro Arg Gln Leu Gln Gln Arg
            20                  25                  30

Gln

<210> SEQ ID NO 174
<211> LENGTH: 11
<212> TYPE: PRT
<213> ORGANISM: artificial sequence
<220> FEATURE:
<223> OTHER INFORMATION: Inclusion body tag IBT-24

<400> SEQUENCE: 174

Ser Arg Arg Pro Arg Gln Leu Gln Gln Arg Gln
1               5                   10

<210> SEQ ID NO 175
<211> LENGTH: 37
<212> TYPE: PRT
<213> ORGANISM: artificial sequence
<220> FEATURE:
<223> OTHER INFORMATION: Inclusion body tag IBT-25

<400> SEQUENCE: 175

Ser Arg Arg Pro Arg Gln Leu Gln Gln Arg Gln Asp Pro Ser Arg Arg
1               5                   10                  15
```

```
Pro Arg Gln Leu Gln Gln Arg Gln Asp Pro Ser Arg Arg Pro Arg Gln
        20                  25                  30

Leu Gln Gln Arg Gln
        35

<210> SEQ ID NO 176
<211> LENGTH: 22
<212> TYPE: PRT
<213> ORGANISM: artificial sequence
<220> FEATURE:
<223> OTHER INFORMATION: Inclusion body tag IBT-26

<400> SEQUENCE: 176

Ser Arg Arg Pro Glu Gln Leu Gln Gln Arg Gln Ser Arg Arg Pro Glu
1               5                   10                  15

Gln Leu Gln Gln Arg Gln
        20

<210> SEQ ID NO 177
<211> LENGTH: 22
<212> TYPE: PRT
<213> ORGANISM: artificial sequence
<220> FEATURE:
<223> OTHER INFORMATION: Inclusion body tag IBT-27

<400> SEQUENCE: 177

Ser Arg Glu Pro Glu Gln Leu Gln Arg Gln Ser Arg Arg Pro Glu
1               5                   10                  15

Gln Leu Gln Gln Arg Gln
        20

<210> SEQ ID NO 178
<211> LENGTH: 22
<212> TYPE: PRT
<213> ORGANISM: artificial sequence
<220> FEATURE:
<223> OTHER INFORMATION: Inclusion body tag IBT-28

<400> SEQUENCE: 178

Ser Arg Glu Pro Glu Gln Leu Gln Gln Arg Gln Ser Arg Glu Pro Glu
1               5                   10                  15

Gln Leu Gln Gln Arg Gln
        20

<210> SEQ ID NO 179
<211> LENGTH: 22
<212> TYPE: PRT
<213> ORGANISM: artificial sequence
<220> FEATURE:
<223> OTHER INFORMATION: Inclusion body tag IBT-29

<400> SEQUENCE: 179

Ser Glu Glu Pro Glu Gln Leu Gln Gln Glu Gln Ser Arg Arg Pro Arg
1               5                   10                  15

Gln Leu Gln Gln Arg Gln
        20

<210> SEQ ID NO 180
<211> LENGTH: 22
<212> TYPE: PRT
<213> ORGANISM: artificial sequence
<220> FEATURE:
<223> OTHER INFORMATION: Inclusion body tag IBT-30

<400> SEQUENCE: 180
```

```
Ser Arg Glu Pro Glu Gln Leu Gln Gln Glu Gln Ser Arg Glu Pro Glu
1               5                   10                  15

Gln Leu Gln Gln Arg Gln
            20

<210> SEQ ID NO 181
<211> LENGTH: 22
<212> TYPE: PRT
<213> ORGANISM: artificial sequence
<220> FEATURE:
<223> OTHER INFORMATION: Inclusion body tag IBT-31

<400> SEQUENCE: 181

Ser Arg Glu Pro Glu Gln Leu Gln Gln Glu Gln Ser Arg Glu Pro Glu
1               5                   10                  15

Gln Leu Gln Gln Glu Gln
            20

<210> SEQ ID NO 182
<211> LENGTH: 24
<212> TYPE: PRT
<213> ORGANISM: artificial sequence
<220> FEATURE:
<223> OTHER INFORMATION: Inclusion body tag IBT-35

<400> SEQUENCE: 182

Ser Arg Arg Pro Arg Gln Leu Gln Gln Arg Gln Ser Arg Arg Pro Arg
1               5                   10                  15

Gln Leu Gln Gln Arg Gln Glu Glu
            20

<210> SEQ ID NO 183
<211> LENGTH: 25
<212> TYPE: PRT
<213> ORGANISM: artificial sequence
<220> FEATURE:
<223> OTHER INFORMATION: Inclusion body tag IBT-36

<400> SEQUENCE: 183

Ser Arg Arg Pro Arg Gln Leu Gln Gln Arg Gln Ser Arg Arg Pro Arg
1               5                   10                  15

Gln Leu Gln Gln Arg Gln Glu Glu Glu
            20                  25

<210> SEQ ID NO 184
<211> LENGTH: 26
<212> TYPE: PRT
<213> ORGANISM: artificial sequence
<220> FEATURE:
<223> OTHER INFORMATION: Inclusion body tag IBT-37

<400> SEQUENCE: 184

Ser Arg Arg Pro Arg Gln Leu Gln Gln Arg Gln Ser Arg Arg Pro Arg
1               5                   10                  15

Gln Leu Gln Gln Arg Gln Glu Glu Glu Glu
            20                  25

<210> SEQ ID NO 185
<211> LENGTH: 28
<212> TYPE: PRT
<213> ORGANISM: artificial sequence
<220> FEATURE:
<223> OTHER INFORMATION: Inclusion body tag IBT-38
```

-continued

```
<400> SEQUENCE: 185

Ser Arg Arg Pro Arg Gln Leu Gln Gln Arg Gln Ser Arg Arg Pro Arg
1               5                   10                  15

Gln Leu Gln Gln Arg Gln Glu Glu Glu Glu Glu
            20                  25

<210> SEQ ID NO 186
<211> LENGTH: 12
<212> TYPE: PRT
<213> ORGANISM: artificial sequence
<220> FEATURE:
<223> OTHER INFORMATION: Inclusion body tag IBT-54

<400> SEQUENCE: 186

Ser Arg Arg Asp Pro Arg Gln Leu Gln Gln Arg Gln
1               5                   10

<210> SEQ ID NO 187
<211> LENGTH: 26
<212> TYPE: PRT
<213> ORGANISM: artificial sequence
<220> FEATURE:
<223> OTHER INFORMATION: Inclusion body tag IBT-89

<400> SEQUENCE: 187

Ser Arg Arg Pro Arg Gln Asp Pro Leu Gln Gln Arg Gln Asp Pro Ser
1               5                   10                  15

Arg Arg Pro Arg Gln Leu Gln Gln Arg Gln
            20                  25

<210> SEQ ID NO 188
<211> LENGTH: 28
<212> TYPE: PRT
<213> ORGANISM: artificial sequence
<220> FEATURE:
<223> OTHER INFORMATION: Inclusion body tag IBT-90

<400> SEQUENCE: 188

Ser Arg Arg Pro Arg Gln Asp Pro Leu Gln Gln Arg Gln Asp Pro Ser
1               5                   10                  15

Arg Arg Pro Arg Gln Asp Pro Leu Gln Gln Arg Gln
            20                  25

<210> SEQ ID NO 189
<211> LENGTH: 21
<212> TYPE: PRT
<213> ORGANISM: artificial sequence
<220> FEATURE:
<223> OTHER INFORMATION: Inclusion body tag IBT-95

<400> SEQUENCE: 189

Ser Arg Arg Pro Arg Gln Leu Gln Gln Arg Gln Ser Leu Gly Tyr Gly
1               5                   10                  15

Gly Leu Tyr Gly Tyr
            20

<210> SEQ ID NO 190
<211> LENGTH: 15
<212> TYPE: PRT
<213> ORGANISM: Zea mays

<400> SEQUENCE: 190

Val His Leu Pro Pro Pro Cys His Tyr Pro Thr Gln Pro Pro
1               5                   10                  15
```

<210> SEQ ID NO 191
<211> LENGTH: 15
<212> TYPE: PRT
<213> ORGANISM: Zea mays

<400> SEQUENCE: 191

Arg Pro Gln Pro His Pro Gln Pro His Pro Cys Pro Cys Gln Gln
1               5                   10                  15

<210> SEQ ID NO 192
<211> LENGTH: 15
<212> TYPE: PRT
<213> ORGANISM: Zea mays

<400> SEQUENCE: 192

Pro Pro Cys His Tyr Pro Thr Gln Pro Pro Arg Pro Gln Pro His
1               5                   10                  15

<210> SEQ ID NO 193
<211> LENGTH: 15
<212> TYPE: PRT
<213> ORGANISM: Zea mays

<400> SEQUENCE: 193

Pro Gln Pro His Pro Cys Pro Cys Gln Gln Pro His Pro Ser Pro
1               5                   10                  15

<210> SEQ ID NO 194
<211> LENGTH: 15
<212> TYPE: PRT
<213> ORGANISM: Zea mays

<400> SEQUENCE: 194

Pro Thr Gln Pro Pro Arg Pro Gln Pro His Pro Gln Pro His Pro
1               5                   10                  15

<210> SEQ ID NO 195
<211> LENGTH: 15
<212> TYPE: PRT
<213> ORGANISM: Zea mays

<400> SEQUENCE: 195

Phe Leu Arg His Gln Cys Ser Pro Thr Ala Thr Pro Tyr Cys Ser
1               5                   10                  15

<210> SEQ ID NO 196
<211> LENGTH: 15
<212> TYPE: PRT
<213> ORGANISM: Zea mays

<400> SEQUENCE: 196

Pro Gln Cys Gln Ser Leu Arg Gln Gln Cys Cys Gln Gln Leu Arg
1               5                   10                  15

<210> SEQ ID NO 197
<211> LENGTH: 25
<212> TYPE: PRT
<213> ORGANISM: Zea mays

<400> SEQUENCE: 197

Pro Thr Gln Pro Pro Arg Pro Gln Pro His Pro Gln Pro His Pro Cys
1               5                   10                  15

Pro Cys Gln Gln Pro His Pro Ser Pro

-continued

```
                    20                  25

<210> SEQ ID NO 198
<211> LENGTH: 20
<212> TYPE: PRT
<213> ORGANISM: Zea mays

<400> SEQUENCE: 198

Arg Pro Gln Pro His Pro Gln Pro His Pro Cys Pro Cys Gln Gln Pro
1               5                   10                  15

His Pro Ser Pro
            20

<210> SEQ ID NO 199
<211> LENGTH: 41
<212> TYPE: PRT
<213> ORGANISM: artificial sequence
<220> FEATURE:
<223> OTHER INFORMATION: IBT-180 tag

<400> SEQUENCE: 199

Met Ala Ser Met Thr Gly Gly Gln Gln Met Gly Val His Leu Pro Pro
1               5                   10                  15

Pro Pro Cys His Tyr Pro Thr Gln Pro Pro Arg Pro Gln Pro His Pro
            20                  25                  30

Gln Pro His Pro Cys Pro Cys Gln Gln
        35                  40

<210> SEQ ID NO 200
<211> LENGTH: 111
<212> TYPE: PRT
<213> ORGANISM: artificial sequence
<220> FEATURE:
<223> OTHER INFORMATION: IBT-181 tag

<400> SEQUENCE: 200

Met Ala Ser Met Thr Gly Gly Gln Gln Met Gly Val His Leu Pro Pro
1               5                   10                  15

Pro Pro Cys His Tyr Pro Thr Gln Pro Pro Arg Pro Gln Pro His Pro
            20                  25                  30

Gln Pro His Pro Cys Pro Cys Gln Gln Pro His Pro Ser Pro Cys Gln
        35                  40                  45

Leu Gln Gly Thr Cys Gly Val Gly Ser Thr Pro Ile Leu Gly Gln Cys
    50                  55                  60

Val Glu Phe Leu Arg His Gln Cys Ser Pro Thr Ala Thr Pro Tyr Cys
65                  70                  75                  80

Ser Pro Gln Cys Gln Ser Leu Arg Gln Gln Cys Cys Gln Gln Leu Arg
                85                  90                  95

Gln Val Glu Pro Gln His Arg Tyr Gln Ala Ile Phe Gly Leu Val
            100                 105                 110

<210> SEQ ID NO 201
<211> LENGTH: 12
<212> TYPE: PRT
<213> ORGANISM: Daucus carota

<400> SEQUENCE: 201

Met Ala Ala Lys Thr Gln Ala Ile Leu Ile Leu Leu
1               5                   10

<210> SEQ ID NO 202
```

```
<211> LENGTH: 12
<212> TYPE: PRT
<213> ORGANISM: Daucus carota

<400> SEQUENCE: 202

Leu Ile Ser Ala Val Leu Ile Ala Ser Pro Ala Ala
1               5                   10

<210> SEQ ID NO 203
<211> LENGTH: 12
<212> TYPE: PRT
<213> ORGANISM: Daucus carota

<400> SEQUENCE: 203

Gln Leu Gly Glu Tyr Ser Val Glu Gln Tyr Asn Gln
1               5                   10

<210> SEQ ID NO 204
<211> LENGTH: 12
<212> TYPE: PRT
<213> ORGANISM: Daucus carota

<400> SEQUENCE: 204

Gln His His Asn Gly Asp Gly Gly Asp Ser Thr Asp
1               5                   10

<210> SEQ ID NO 205
<211> LENGTH: 12
<212> TYPE: PRT
<213> ORGANISM: Daucus carota

<400> SEQUENCE: 205

Ser Ala Gly Asp Leu Lys Phe Val Lys Val Val Ala
1               5                   10

<210> SEQ ID NO 206
<211> LENGTH: 12
<212> TYPE: PRT
<213> ORGANISM: Daucus carota

<400> SEQUENCE: 206

Ala Glu Lys Gln Val Val Ala Gly Ile Lys Tyr Tyr
1               5                   10

<210> SEQ ID NO 207
<211> LENGTH: 12
<212> TYPE: PRT
<213> ORGANISM: Daucus carota

<400> SEQUENCE: 207

Leu Lys Ile Val Ala Ala Lys Gly Gly His Lys Lys
1               5                   10

<210> SEQ ID NO 208
<211> LENGTH: 12
<212> TYPE: PRT
<213> ORGANISM: Daucus carota

<400> SEQUENCE: 208

Lys Phe Asp Ala Glu Ile Val Val Gln Ala Trp Lys
1               5                   10

<210> SEQ ID NO 209
<211> LENGTH: 13
<212> TYPE: PRT
```

<213> ORGANISM: Daucus carota

<400> SEQUENCE: 209

Lys Thr Lys Gln Leu Met Ser Phe Ala Pro Ser His Asn
1               5                   10

<210> SEQ ID NO 210
<211> LENGTH: 12
<212> TYPE: PRT
<213> ORGANISM: Daucus carota

<400> SEQUENCE: 210

Val Leu Ile Ala Ser Pro Ala Ala Gly Leu Gly Gly
1               5                   10

<210> SEQ ID NO 211
<211> LENGTH: 12
<212> TYPE: PRT
<213> ORGANISM: Daucus carota

<400> SEQUENCE: 211

Tyr Ser Val Glu Gln Tyr Asn Gln Gln His His Asn
1               5                   10

<210> SEQ ID NO 212
<211> LENGTH: 12
<212> TYPE: PRT
<213> ORGANISM: Daucus carota

<400> SEQUENCE: 212

Leu Lys Phe Val Lys Val Val Ala Ala Glu Lys Gln
1               5                   10

<210> SEQ ID NO 213
<211> LENGTH: 12
<212> TYPE: PRT
<213> ORGANISM: Daucus carota

<400> SEQUENCE: 213

Ala Ala Lys Gly Gly His Lys Lys Lys Phe Asp Ala
1               5                   10

<210> SEQ ID NO 214
<211> LENGTH: 12
<212> TYPE: PRT
<213> ORGANISM: Daucus carota

<400> SEQUENCE: 214

Glu Glu Ile Gln Gln Leu Gly Glu Tyr Ser Val Glu
1               5                   10

<210> SEQ ID NO 215
<211> LENGTH: 12
<212> TYPE: PRT
<213> ORGANISM: Daucus carota

<400> SEQUENCE: 215

Gln Tyr Asn Gln Gln His His Asn Gly Asp Gly Gly
1               5                   10

<210> SEQ ID NO 216
<211> LENGTH: 12
<212> TYPE: PRT
<213> ORGANISM: Daucus carota -continued

```
<400> SEQUENCE: 216

Asp Ser Thr Asp Ser Ala Gly Asp Leu Lys Phe Val
1               5                   10

<210> SEQ ID NO 217
<211> LENGTH: 12
<212> TYPE: PRT
<213> ORGANISM: Daucus carota

<400> SEQUENCE: 217

Gly His Lys Lys Lys Phe Asp Ala Glu Ile Val Val
1               5                   10

<210> SEQ ID NO 218
<211> LENGTH: 12
<212> TYPE: PRT
<213> ORGANISM: Daucus carota

<400> SEQUENCE: 218

Gln Ala Trp Lys Lys Thr Lys Gln Leu Met Ser Phe
1               5                   10

<210> SEQ ID NO 219
<211> LENGTH: 128
<212> TYPE: PRT
<213> ORGANISM: artificial sequence
<220> FEATURE:
<223> OTHER INFORMATION: inclusion body tag KSI(C4)E

<400> SEQUENCE: 219

Met His Thr Pro Glu His Ile Thr Ala Val Val Gln Arg Phe Val Ala
1               5                   10                  15

Ala Leu Asn Ala Gly Glu Leu Glu Gly Ile Val Ala Leu Phe Ala Glu
                20                  25                  30

Glu Ala Thr Val Glu Glu Pro Val Gly Ser Glu Pro Arg Ser Gly Thr
            35                  40                  45

Ala Ala Cys Arg Glu Phe Tyr Ala Asn Ser Leu Lys Leu Pro Leu Ala
        50                  55                  60

Val Glu Leu Thr Gln Glu Cys Arg Ala Val Ala Asn Glu Ala Ala Phe
65                  70                  75                  80

Ala Phe Thr Val Ser Phe Glu Tyr Gln Gly Arg Lys Thr Val Val Ala
                85                  90                  95

Pro Cys Glu His Phe Arg Phe Asn Gly Ala Gly Lys Val Val Ser Ile
            100                 105                 110

Arg Ala Leu Phe Gly Glu Lys Asn Ile His Ala Cys Gln Gly Ser Asp
        115                 120                 125
```

USE OF TETRACYSTEINE TAGS IN FLUORESCENCE-ACTIVATED CELL SORTING ANALYSIS OF PROKARYOTIC CELLS PRODUCING PEPTIDES OR PROTEINS

CROSS REFERENCE TO RELATED APPLICATIONS

This application claims the benefit of U.S. Provisional Patent Application No. 60/984,876, filed Nov. 2, 2007.

FIELD OF THE INVENTION

The invention relates to the field of in vivo detection of recombinantly produced peptides or proteins in prokaryotic microbial host cells. More specifically prokaryotic cells that express fusion peptides that comprise at least one tetracysteine tag are labeled in vivo with a biarsenical labeling reagent that binds to the tetracysteine tag and forms a detectable fluorescent complex. These cells are detected or sorted and detected using a fluorescence activated cell sorter [FACS]. The process does not include permeabilizing or pretreating the cells for effective labeling.

BACKGROUND OF THE INVENTION

Efficient production of bioactive proteins and peptides is a primary function of the biomedical and industrial biochemical industry. Bioactive peptides and proteins are used as curative agents in a variety of diseases such as diabetes (insulin), viral infections and leukemia (interferon), diseases of the immune system (interleukins), and red blood cell deficiencies (erythropoietin) to name a few. Additionally, large quantities of proteins and peptides are needed for various industrial applications including, for example, the pulp and paper industries, textiles, food industries, personal care and cosmetics industries, sugar refining, wastewater treatment, production of alcoholic beverages and as catalysts for the generation of new pharmaceuticals.

With the discovery and implementation of combinatorial peptide screening technologies new applications for small peptides having specific binding affinities have been developed. These technologies include bacterial display (Kemp, D. J.; *Proc. Natl. Acad. Sci. USA* 78(7): 4520-4524 (1981); yeast display (Chien et al., *Proc Natl Acad Sci USA* 88(21): 9578-82 (1991)), combinatorial solid phase peptide synthesis (U.S. Pat. No. 5,449,754; U.S. Pat. No. 5,480,971; U.S. Pat. No. 5,585,275 and U.S. Pat. No. 5,639,603), phage display technology (U.S. Pat. No. 5,223,409; U.S. Pat. No. 5,403,484; U.S. Pat. No. 5,571,698; and U.S. Pat. No. 5,837,500), ribosome display (U.S. Pat. No. 5,643,768; U.S. Pat. No. 5,658,754; and U.S. Pat. No. 7,074,557), and mRNA display technology (PROFUSION™; U.S. Pat. No. 6,258,558; U.S. Pat. No. 6,518,018; U.S. Pat. No. 6,281,344; U.S. Pat. No. 6,214,553; U.S. Pat. No. 6,261,804; U.S. Pat. No. 6,207,446; U.S. Pat. No. 6,846,655; U.S. Pat. No. 6,312,927; U.S. Pat. No. 6,602,685; U.S. Pat. No. 6,416,950; U.S. Pat. No. 6,429,300; U.S. Pat. No. 7,078,197; and U.S. Pat. No. 6,436,665)]

In particular, in biomedical fields small peptides are regarded as linkers for the attachment of diagnostic and pharmaceutical agents to surfaces (see U.S. Pat. App. Pub. No. 2003/0185870 to Grinstaff et al., and U.S. Pat. No. 6,620,419 to Linter), as well as in the personal care industry for the attachment of benefit agents to body surfaces such as hair and skin (see commonly-owned U.S. Pat. No. 7,220,405 to Huang et al., and U.S. Pat. App. Pub. No. 2003/0152976 to Janssen et al.), and in the printing industry for the attachment of pigments to print media (see commonly-owned U.S. Pat. App. Pub. No. 2005/0054752).

Some commercially useful peptides may be synthetically generated or isolated from natural sources. However, these methods are often expensive, time consuming and characterized by limited production capacity. The preferred method of peptide production is through the fermentation of recombinant microorganisms engineered to express the protein or peptide of interest. Although preferable to synthesis or isolation, recombinant peptide production has a number of obstacles to be overcome in order to be cost-effective. For example, peptides and in particular short peptides produced in a cellular environment are susceptible to degradation by native proteases in the cell. Additionally, the purification of some peptides may be difficult depending on the nature of the protein or peptide of interest and may result in poor yields.

One means to mitigate the difficulties associated with recombinant peptide production is the use of chimeric genetic constructs encoding chimeric proteins. The chimeric proteins may comprise at least one portion of the desired protein product fused to at least one portion comprising a peptide tag, referred to herein as "fusion proteins". The peptide tag may be used to assist protein folding, post expression purification and/or protein passage through the cell membrane and to protect the protein from the action of degradative enzymes, In many cases it is useful to express a peptide in insoluble form, particularly when the peptide of interest (POI) is a small peptide that is typically soluble under normal physiological conditions and/or subject to endogenous proteolytic degradation within the host cell. Production of the peptide in an insoluble form both facilitates simple recovery and protects the peptide from undesirable proteolytic degradation. One means to produce the peptide of interest in an insoluble form is to recombinantly produce the peptide as part of an insoluble fusion peptide by including at least one peptide tag (referred to herein as a "solubility tag" or "inclusion body tag") that induces inclusion body formation. The fusion protein may include at least one cleavable peptide linker so that the peptide of interest can be subsequently recovered from the fusion protein. The fusion protein may include a plurality of inclusion body tags, cleavable peptide linkers, and regions comprising the peptide of interest.

Recombinant microbial peptide production often requires the ability to efficiently label, detect/monitor, and/or screen/select cells producing the desired fusion peptide. This ability is useful during both the strain development phase (i.e., identity strains/mutants/growth conditions that improve peptide production) and commercial production phase (i.e. process monitoring). During strain development, it is particularly desirable to identify and select strains exhibiting improved performance using a technique that is sensitive, fast, easy, and non-toxic to the recombinant cell, i.e., permits selection and subsequent growth of the selected cells, and amenable to high-throughput processing or screening.

Various fluorescent labeling and detection techniques have been reported in the art to monitor and/or measure peptide production, although many of these techniques are not cost-effective or suitable for in vivo labeling and detection, especially when producing small peptides. Giepmans et al. (*Science* 312:217-224 (2006)) reviews the fluorescent "toolbox" for assessing protein production/location and function. Many of the labeling techniques require the use of a targeting molecule to achieve specific labeling, e.g. fusion of small organic dyes and/or quantum dots to antibodies. However, such immunological techniques often require fixation and/or permeabilization and are not amenable to in vivo labeling, especially when one wants to select and grow the cells exhibiting an improvement in peptide production.

Another peptide labeling approach is the incorporation of a detectable fluorescent marker as part of the fusion construct. For example, fluorescent proteins such as green fluorescent protein (GFP) and yellow fluorescent protein (YFP) are often used to detect and/or measure recombinant peptide production. However, fusion constructs comprising a large fluorescent protein are time consuming because they require a significant fluorescence development period) and may place an additional metabolic burden on the microbial host cell. Fusion of a large fluorescent protein to the peptide of interest adversely affects the production efficiency of the peptide of interest, especially when the peptide of interest is small relative to the fluorescent protein. It is desirable to use a detectable marker that is small, easily detectable (sensitive with low background noise), and suitable for in vivo labeling and detection applications. In particular, a simple and effective in vivo labeling system that can be used in combination with a fluorescence activated cell sorter (FACS) for detection and/or selection is desirable.

The LUMIO™ protein detection system (Invitrogen Life Technologies, Carlsbad, Calif.) is based on the incorporation of a small tetracysteine tag (TC) that covalently binds to a biarsenical labeling reagent (e.g. FlAsH-EDT$_2$ [LUMIO™ green]; ReAsh-EDT$_2$ [LUMIO™ red]); and CHoXAsh-EDT$_2$ (U.S. Pat. No. 5,932,474; U.S. Pat. No. 6,054,271; U.S. Pat. No. 6,831,160; U.S. Pat. No. 6,008,378; U.S. Pat. No. 6,451,564; U.S. Pat. No. 6,686,458; U.S. Pat. No. 7,138,503; EP1032837, EP1684073, U.S. Pat. App. Pub. No. 20050176065 A1; and Griffin et al., Science 281:269-271 (1998)). Covalent binding of the labeling reagent to the tetracysteine tag generates a highly fluorescent complex. The LUMIO™ detection system has been extensively used to fluorescently label eukaryotic proteins in vivo, especially mammalian cells and mammalian cell lines (Ho and Starnbach, Infect. Immunity, 73(2):905-911 (2005); Adams et al., JACS, 124:6063-6076 (2002); Stroffekova and Proenza, Eur. J. Physiol., 442:859-866 (2001); Rice et al., Nat. Biotechnol., 19:321-326 (2001); and Int'l App. Pub. No. WO2007/023184A1.

Griffin et al. (Meth. Enzymol., 327:565-578 (2000)) reports that labeling of intact bacterial cells requires much higher concentrations of the biarsenical labeling reagent in the presence of β-mercaptoethanol (2-ME) for several hours (unpublished data), suggesting that the labeling reagent cannot easily penetrate into prokaryotic cells.

Ignatova and Gierash (PNAS, 101 (2):523-528 (2004)) reports in vivo labeling of E. coli cells using a tetracysteine tag/biarsenical labeling reagent system wherein the fluorescence spectra was measured using a fluorometer. However, the labeling process required lysozyme pretreatment to make the outer membrane permeable to the labeling reagent.

A simple and cost effective process for in vivo labeling and detecting TC-tagged proteins produced within prokaryotic cells that does not require the use of undesirable compounds, e.g. β-mercaptoethanol, and/or a permeabilizing pretreatment, e.g. lysozyme treatment, has not been reported. In general, the use of permeabilizing agents and/or reducing agents is undesirable as the treated cells may be non-viable and/or undergo an unpredictable stress response that may influence peptide production and/or the cell's growth characteristics. This is particularly important when the goal of the labeling process is to identify and select viable cells suitable for use in further experiments.

Furthermore, many commercial applications for small bioactive peptides often require purified product. Many of these small peptides are produced in a recombinant prokaryotic host cell in the form of insoluble fusion peptides. A labeling system that is both effective for monitoring fusion peptide production and enables separation from the peptide of interest during subsequent bulk processing is needed.

The problem to be solved is to provide a process of in vivo labeling fusion peptides recombinantly produced within a prokaryotic cell, which is fast, efficient, sensitive, and does not require the use of permeabilized cells. That is, the process does not include the need to contact the cells with an undesirable agent to increase permeability in order to achieve effective in vivo labeling. Furthermore, the process should include a fast and effective means for detecting and/or selecting viable, labeled cells characterized by improved peptide production, e.g. the use of a fluorescence activated cell sorter to collect live cells. In one aspect, the process should be capable of selecting and isolating live cells suitable for use in further experiments and/or selections. In another aspect, the process may include repeatable steps (growth-labeling-detection-selection) that may include at least one round of mutagenesis to facilitate host cell optimization (e.g. increased peptide production).

SUMMARY OF THE INVENTION

The stated problem has been solved through the discovery that peptides or proteins comprising a tetracysteine tag (TC) can be labeled in vivo with biarsenical labeling reagents using prokaryotic host cells that have not been pre-treated with permeabilizing agents and/or reducing agents. The in vivo labeling may be combined with a fluorescence activated cell sorter (FACS), enabling fast and efficient detection and selection of prokaryotic cells producing the desired peptide or protein.

The tetracysteine-tagged peptide or protein may be an insoluble fusion peptide comprising at least one inclusion body tag. The tetracysteine tag may be operably-linked to the portion of the fusion protein comprising the inclusion body tag.

Described herein is process of in vivo labeling and detecting a polypeptide or protein in a prokaryotic cell comprising:

a) providing an unpermeabilized prokaryotic host cell comprising a chimeric genetic construct encoding a polypeptide or protein comprising at least one tetracysteine tag;

b) growing the unpermeabilized prokaryotic host cell of (a) under suitable conditions express the chimeric genetic construct and to produce the polypeptide or protein comprising said at least one tetracysteine tag;

c) contacting in vivo the unpermeabilized prokaryotic host cell of (b) with an effective amount of at least one biarsenical labeling reagent which binds to the at least one tetracysteine tag forming at least one fluorescent complex; and d) detecting unpermeabilized prokaryotic cells comprising the at least one fluorescent complex.

The chimeric genetic construct may encode a fusion peptide comprising:

i) at least one first portion comprising an inclusion body tag (IBT);

ii) at least one second portion comprising a peptide of interest (POI); and iii) at least one tetracysteine tag (TC).

The fusion peptide may have the general structure:

IBT-TC-CL-POI or POI-CL-TC-IBT wherein a) CL is a cleavable peptide linker;

b) the tetracysteine tag comprises amino acid sequence SEQ ID NO: 2;

c) the biarsenical labeling reagent is selected from the group consisting of fluorescein arsenical hairpin binding reagent and resorufin arsenical hairpin binding reagent; and d) the prokaryotic cell is *Escherichia coli*.

The affinity peptide is preferably a combinatorially generated peptide identified using phage display, bacterial display, yeast display, ribosome display, or mRNA-display.

The peptide of interest is selected from the group consisting of hair-binding peptides, nail-binding peptides, skin-binding peptides, tooth-binding peptides, antimicrobial peptides, pigment binding peptides, cellulose-binding peptides, polymer-binding peptides, and clay-binding peptides.

The peptide of interest may be a multi-block peptide having a two or more binding moieties wherein the binding moieties may be the same or different.

BRIEF DESCRIPTION OF THE FIGURES

FIG. 3A is a fluorescence intensity plot of cells grown in DEK medium induced at $OD_{600}$ 1.5. FIG. 3B is a fluorescence intensity plot of cells grown in LB medium induced at $OD_{600}$ 0.5. The DEK grown cells or the LB grown cells were induced for three hours with 0.2% L-arabinose and labeled for 1.5 hours as described in Example 7.

BRIEF DESCRIPTION OF THE BIOLOGICAL DEPOSIT

Figure 1B:
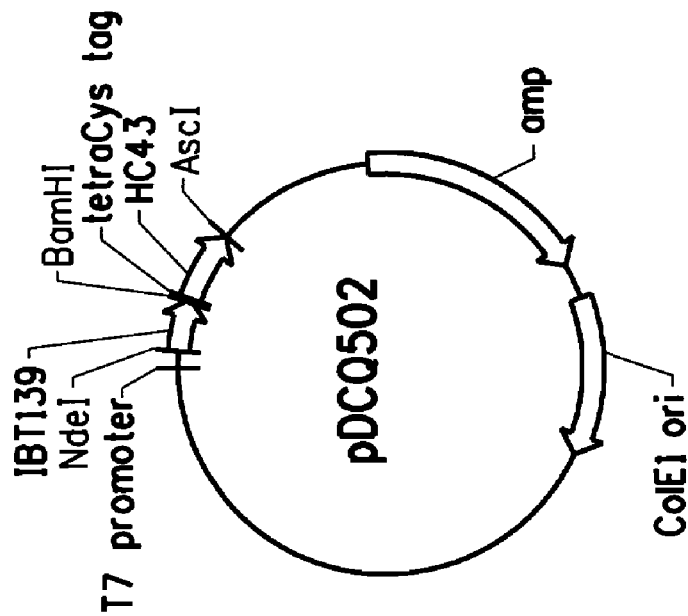
FIGS. 1A-D are plasmid maps of various expression plasmids containing the tetracysteine tag.

The following biological deposit has been made under the terms of the Budapest Treaty on the International Recognition of the Deposit of Microorganisms for the purposes of Patent Procedure:

| Depositor Identification Reference | Int'l. Depository Designation | Date of Deposit |
|---|---|---|
| Plasmid pCP20 | ATCC PTA-4455 | Jun. 13, 2002 |

As used herein, "ATCC" refers to the American Type Culture Collection International Depository Authority located at ATCC, 10801 University Blvd., Manassas, Va. 20110-2209, USA. The "International Depository Designation" is the accession number to the culture on deposit with ATCC.

The listed deposits will be maintained in the indicated international depository for at least thirty (30) years and will be made available to the public upon the grant of a patent disclosing it. The availability of a deposit does not constitute a license to practice the subject invention in derogation of patent rights granted by government action

BRIEF DESCRIPTION OF THE BIOLOGICAL SEQUENCES

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPC and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the amino acid sequence of the tetracysteine tag CCXXCC.

SEQ ID NO: 2 is the amino acid sequence of the tetracysteine tag CCPGCC.

SEQ ID NOs: 3 and 4 are primers.

SEQ ID NO: 5 is the amino acid sequence of peptide AO9.

SEQ ID NO: 6 is the amino acid sequence of peptide KF11.

SEQ ID NO: 7 is the nucleic acid sequence encoding the peptide HC77643.

SEQ ID NO: 8 is the amino acid sequence of HC77643 (a multi-block hair-binding peptide)

SEQ ID NO: 9 is the nucleic acid sequence encoding the peptide HC776124.

SEQ ID NO: 10 is the amino acid sequence of HC776124 (a multi-block hair-binding peptide).

SEQ ID NO: 11 is the nucleic acid sequence of inclusion body tag IBT139.

SEQ ID NO: 12 is the amino acid sequence of inclusion body tag IBT139.

SEQ ID NO: 13 is the nucleic acid sequence of inclusion body tag IBT139.CCPGCC.

SEQ ID NO: 14 is the amino acid sequence of inclusion body tag IBT139.CCPGCC.

SEQ ID NO: 15 is the nucleic acid sequence encoding inclusion body tag KSI(C4).

SEQ ID NO: 16 is the amino acid sequence of inclusion body tag KSI(C4).

SEQ ID NO: 17 is the amino acid sequence of the core sequence found in a family of inclusion body tags (see co-pending and commonly owned U.S. patent application Ser. No. 11/782,836).

SEQ ID NO: 18 is the nucleic acid sequence of expression plasmid pLR186.

SEQ ID NO: 19 is the nucleic acid sequence of expression plasmid pTG28.

SEQ ID NO: 20 is the nucleic acid sequence of expression plasmid pTG34.

SEQ ID NO: 21 is the nucleic acid sequence of expression plasmid pLR173.

SEQ ID NO: 22 is the nucleic acid sequence of expression plasmid pLR199.

SEQ ID NO: 23 is the nucleic acid sequence of expression plasmid pDCQ500.

SEQ ID NO: 24 is the nucleic acid sequence of expression plasmid pDCQ502.

SEQ ID NO: 25 is the nucleic acid sequence of expression plasmid pDCQ506.

SEQ ID NOs: 8, 10, and 26-49 are the amino acid sequences of hair-binding peptides.

SEQ ID NOs: 50-62 are the amino acid sequences of skin-binding peptides.

SEQ ID NOs: 63-64 are the amino acid sequences of nail-binding peptides.

SEQ ID NOs: 65-93 are the amino acid sequences of anti-microbial peptides.

SEQ ID NOs: 94-119 are the amino acid sequences of pigment-binding peptides. Specifically, SEQ ID NOs: 94-98 bind to carbon black, SEQ ID NOs: 99-106 bind to CROMOPHTAL® yellow (Ciba Specialty Chemicals, Basel, Switzerland), SEQ ID NOs: 107-109 bind to SUNFAST® magenta (Sun Chemical Corp., Parsippany, N.J.), and SEQ ID NOs: 110-119 bind to SUNFAST® blue.

SEQ ID NOs: 120-125 are the amino acid sequences of cellulose-binding peptides.

SEQ ID NOs: 126-153 are the amino acid sequences of polymer-binding peptides. Specifically, SEQ ID NO: 126 binds to poly(ethylene terephthalate), SEQ ID NOs: 127-138 bind to poly(methyl methacrylate), SEQ ID NOs: 139-144 bind to Nylon, and SEQ ID NOs: 145-153 bind to poly(tetrafluoroethylene).

SEQ ID NOs: 154-169 are the amino acid sequences of clay binding peptides.

SEQ ID NO: 170 is the amino acid sequence of the Caspase-3 cleavage sequence.

SEQ ID NOs: 171-219 are the amino acid sequences of various additional inclusion body tags (see co-pending and commonly owned U.S. patent application Ser. Nos. 11/641,936; 11/641,273; 11/516,362; and 12/172,385).

DETAILED DESCRIPTION

Described herein is a process of in vivo labeling and detecting a polypeptide or protein comprising a tetracysteine tag (TC) in a recombinant prokaryotic host cell using a biarsenical labeling reagent. The process does not pretreat the recombinant prokaryotic cells with lysozyme or harsh chemical agents, such as β-mercaptoethanol or toluene prior to in vivo labeling.

The tetracysteine-tagged polypeptide may be recombinantly produced in the prokaryotic host cell in an insoluble form, such as inclusion bodies, by incorporating a solubility tag to form an insoluble fusion protein. Covalent binding of the labeling reagent to the TC tag forms a fluorescent complex that can measure the level fusion peptide production. A fluorescence activated cell sorter (FACS) may be used to identify, measure and/or isolate subpopulations of the prokaryotic cells based on fluorescence intensity.

The prokaryotic host cell may be an enteric bacterial host cell. The enteric bacterial host cell may be *Escherichia coli* cell. The *Escherichia coli* cell preferably comprises a disruption in the endogenous arabinose operon (ΔaraBAD) for efficient expression of the fusion peptide under the pBAD promoter.

The following definitions are used herein and should be referred to for interpretation of the claims and the specification.

As used herein, the indefinite articles "a" and "an" preceding an element or component of the invention are intended to be nonrestrictive regarding the number of instances (i.e., occurrences) of the element or component. Therefore "a" or "an" should be read to include one or at least one, and the singular word form of the element or component also includes the plural unless the number is obviously meant to be singular.

As used herein, the term "comprising" means the presence of the stated features, integers, steps, or components as referred to in the claims, but that it does not preclude the presence or addition of one or more other features, integers, steps, components or groups thereof.

As used herein, the term "about" refers to modifying the quantity of an ingredient or reactant of the invention or employed refers to variation in the numerical quantity that can occur, for example, through typical measuring and liquid handling procedures used for making concentrates or use solutions in the real world; inadvertent error in these procedures; differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

As used herein, the terms "unpermeabilized prokaryotic host cell", "unpermeabilized prokaryotic cell", and "unpermeabilized cell" refer to a prokaryotic cell used in the present process that has not been subjected to a pretreatment prior to labeling the cell in vivo. As used herein, the "pretreatment" will include any agents, such as lysozyme, toluene, used to increase cell wall permeability to the biarsenical labeling reagent(s) or undesirable reducing agents such as β-mercaptoethanol. "Pretreatment" refers to any treatment that occurs prior to, or simultaneously with, contacting the cell in vivo with the biarsenical labeling reagent. Preferably, the present labeling process does not include contacting the prokaryotic cells with lysozyme and/or β-mercaptoethanol any time during the present process.

As used herein, the term "biarsenical labeling reagent" refers to the biarsenical compounds FlAsH-EDT$_2$ [LUMIO™ Green] and ReAsH-EDT$_2$ [LUMIO™ red], CHoXAsh-EDT$_2$ (a blue biarsenical dye; Adams et al., supra) and derivatives thereof that fluoresce when bound to a tetracysteine tag.

As used herein, the terms "FlAsH-EDT$_2$" and "fluorescein arsenical hairpin binding reagent" refer to the compound 4',5'-bis(1,3,2-dithioarsolan-2-yl)fluorescein-(1,2-ethanedithiol)$_2$. The labeling reagent covalently binds to thiol groups with the tetracysteine tag, generating a fluorescent complex. The excitation maxima has been reported to be 508 nm with an emission maxima at 528 nm.

As used herein, the terms "ReAsH-EDT$_2$" and "resorufin arsenical hairpin binding reagent" refer to 4,5-bis(1,3,2-dithioarsolan-2-yl)-resorufin (complexed with 1,2-ethanedithiol). The labeling reagent covalently binds to thiol groups with the tetracysteine tag, generating a fluorescent complex. The excitation maxima has been reported to be 593 nm with an emission maxima at 608 nm.

As used herein, the term "CHoXAsh-EDT$_2$" refers to the blue biarsenical dye 4,5-bis(1,3,2-dithioarsolan-2-yl)-2,8-dichloro-3,6-dihydroxy-9H-xanthen-9-one (complexed with 1,2-ethanedithiol) (Adams et al., supra).

As used herein, the terms "tetracysteine tag", "tetracysteine motif", "LUMIO™ tag", and "labeling tag" are abbreviated as "TC" and refer to a tetracysteine motif having the formula Cys-Cys-Xaa1-Xaa2-Cys-Cys (SEQ ID NO: 1) wherein Xaa1 and Xaa2 are any naturally occurring amino acid other than cysteine. Derivatives of the tetracysteine motif have been reported to bind the labeling reagents to varying degrees (Adams et al., supra). The tetracysteine tag sequence may preferably be Cys-Cys-Pro-Gly-Cys-Cys (SEQ ID NO: 2). As used herein, a peptide/protein comprising a tetracysteine tag refers to a "TC-tagged" peptide or protein.

As used herein, the term "isolated nucleic acid molecule" is a polymer of RNA or DNA that is single- or double-stranded, optionally containing synthetic, non-natural or altered nucleotide bases. An isolated nucleic acid molecule in the form of a polymer of DNA may be comprised of one or more segments of cDNA, genomic DNA or synthetic DNA.

As used herein, the term "pigment" refers to an insoluble, organic or inorganic colorant.

As used herein, the term "hair" as used herein refers to human hair, eyebrows, and eyelashes.

As used herein, the term "skin" refers to human skin, or substitutes for human skin, such as pig skin, VITRO-SKIN® and EPIDERM™. Skin, as used herein, will refer to a body surface generally comprising a layer of epithelial cells and may additionally comprise a layer of endothelial cells.

As used herein, the term "nails" as used herein refers to human fingernails and toenails.

As used herein, "PBP" is an abbreviation for polymer-binding peptide. As used herein, the term "polymer-binding peptide" refers to peptide sequences that bind with high affinity to a specific polymer (U.S. patent application Ser. No. 11/516,362). Examples include peptides that bind to poly (ethylene terephthalate) (SEQ ID NO: 126), poly(methyl methacrylate) (SEQ ID NOs: 127-138), Nylon (SEQ ID NOs: 139-144), and poly(tetrafluoroethylene) (SEQ ID NOs: 145-153).

As used herein, "HBP" is an abbreviation for hair-binding peptide. As used herein, the term "hair-binding peptide" refers to peptide sequences that bind with high affinity to hair. Examples of hair binding peptides have been reported (U.S. patent application Ser. No. 11/074,473 to Huang et al.; Int'l. App. Pub. No. WO 0179479; U.S. Pat. App. Pub. No. 2002/0098524 to Murray et al.; Janssen et al., U.S. Pat. App. Pub. No. 2003/0152976 to Janssen et al.; Int'l App. Pub. No. WO 2004048399; U.S. patent application Ser. No. 11/512,910, and U.S. Pat. App, No. 11/696,380). Hair-binding peptides may include one or more hair binding domains. As used herein, hair-binding peptides comprising of a plurality of hair-binding domains are referred to herein as "multi-block" or "multi-copy" hair-binding peptides. Examples of hair-binding peptides are provided as SEQ ID NOs: 8, 10, and 26-49.

As used herein, "SBP" is an abbreviation for skin-binding peptide. As used herein, the term "skin-binding peptide" refers to peptide sequences that bind with high affinity to skin. Examples of skin-binding peptides have also been reported (U.S. patent application Ser. No. 11/069,858 to Buseman-Williams; Int'l App. Pub. No. WO 2004/000257 to Rothe et al.; and U.S. patent application Ser. No. 11/696,380). Skin is a body surface comprises a layer of epithelial cells and may additionally comprise a layer of endothelial cells. Examples of skin-binding peptides are provided as SEQ ID NOs: 50-62.

As used herein, "NBP" is an abbreviation for nail-binding peptide. As used herein, the term "nail-binding peptide" refers to peptide sequences that bind with high affinity to nail. Nail-binding peptides have been reported (U.S. patent application Ser. No. 11/696,380). Examples of nail-binding peptides are provided as SEQ ID NOs: 63-64.

As used herein, an "antimicrobial peptide" is a peptide having the ability to kill microbial cell populations (U.S. patent application Ser. No. 11/516,362). Examples of antimicrobial peptides are provided as SEQ ID NOs: 65-93.

As used herein, "cellulose-binding peptide" refers to a peptide that binds with high affinity to cellulose. Examples of cellulose-binding peptides are provided as SEQ ID NOs: 120-125.

As used herein, "clay-binding peptide" refers to a peptide that binds with high affinity to clay (U.S. patent application Ser. No. 11/696,380). Examples of clay-binding peptides are provided as SEQ ID NOs: 154-169.

As used herein, "multi-block peptides" refers to a peptide comprising at least two binding moieties. Each binding moiety has an affinity for a target substrate (e.g. hair, skin, a pigment, etc). The binding moieties may have an affinity for the same or different substrates (for example, a hair-binding moiety fused to a pigment binding moiety for targeted delivery of a pigment to hair or a peptide having a plurality of hair-binding moieties). The construction of multi-block hair-binding peptides has been reported (see co-pending and commonly owned U.S. patent application Ser. Nos. 11/389,948 and 11/074,473).

As used herein, the term "inclusion body tag" is abbreviated "IBT" and refers to a polypeptide that facilitates formation of inclusion bodies when fused to a peptide of interest. The peptide of interest is typically soluble within the host cell and/or host cell lysate when not fused to an inclusion body tag. Fusion of the peptide of interest to the inclusion body tag produces a fusion protein that agglomerates into intracellular bodies (inclusion bodies) within the host cell.

As used herein, "cleavable linker elements", "peptide linkers", "cleavable peptide linkers", and "cleavage site" will be used interchangeably and refer to cleavable peptide segments located between the inclusion body tag and the peptide of interest or between the tetracysteine tag and the peptide of interest. In a preferred embodiment, the portion of the fusion protein comprising the inclusion body tag further comprises at least one tetracysteine tag. After the inclusion bodies are separated, partially-purified or purified from the cell lysate (typically reserved for bulk processing), the linker elements can be cleaved chemically and/or enzymatically to separate the inclusion body tag from the peptide of interest. The fusion peptide may also include a plurality of regions encoding one or more peptides of interest separated by one or more cleavable peptide linkers. The peptide of interest can then be isolated from the inclusion body tag, if necessary. It should be noted that isolation of POI is typically reserved for bulk processing of fermented cells and not the sample aliquots used for the present labeling and detection process. The inclusion body tag(s) and the peptide of interest may have different solubilities in a defined medium, such as aqueous solution. The solubility difference enables separation of the inclusion body tag from the polypeptide of interest. The inclusion body tag may preferably be insoluble in an aqueous solution while the protein/polypeptide of interest is appreciably soluble in an aqueous solution. The pH, temperature, and/or ionic strength of the aqueous solution can be adjusted to facilitate recovery of the peptide of interest. The difference in solubility between the inclusion body tag and the peptide of interest may preferably occur in an aqueous solution having a pH of 5 to 10 and a temperature range of about 15° C. to about 50° C.

The cleavable peptide linker may be from 1 to about 50 amino acids, preferably from 1 to about 20 amino acids in length, and most preferably about 2 to about 10 amino acids in length. An example of an enzymatically cleavable peptide linker is provided by SEQ ID NO: 170 (Caspase-3 cleavage recognition sequence). Preferably, the cleavage site is an acid cleavable aspartic acid-proline dipeptide (D-P) moiety. The cleavable peptide linkers may be incorporated into the fusion proteins using any number of techniques well known in the art. The inclusion body tag may also comprise an effective number of cross-linkable cysteine residues whereby oxidative cross-linking can be used to selectively precipitate the IBT once cleaved from the POI (see co-pending and commonly owned U.S. patent application Ser. No. 12/172,395).

As used herein, the term "operably-linked" refers to the association of nucleic acid sequences on a single nucleic acid fragment so that the function of one is affected by the other. For example, a promoter is operably-linked with a coding sequence when it is capable of affecting the expression of that coding sequence, that is, that the coding sequence is under the transcriptional control of the promoter. The definition of "operably linked" may also be extended to describe the products of chimeric genes, such as fusion peptides. As such, "operably-linked" refers to the linking of an inclusion body tag to a peptide of interest to be produced and recovered.

As used herein, the terms "fusion peptide", "fusion protein", "chimeric protein", and "chimeric peptide" are used interchangeably and refer to a polymer of amino acids—peptide, oligopeptide, polypeptide, or protein—comprising at least two portions, each portion comprising a distinct function. At least one first portion of the fusion peptide comprises at least one inclusion body tag. At least one second portion of the fusion peptide comprises at least one peptide of interest. The fusion peptide comprises at least one tetracysteine tag. The tetracysteine tag may be separated from the peptide of interest using a cleavable peptide linker. The inclusion body tag may comprise the tetracysteine tag wherein the peptide of interest targeted for use in commercial product formulations does not include the tetracysteine tag. The tetracysteine tag may be located on the amino and/or carboxy terminus of the inclusion body tag and is separated from the peptide of interest by at least one cleavable peptide linker.

As used herein, the terms "polypeptide" and "peptide" are used interchangeably to refer to a polymer of two or more amino acids joined together by a peptide bond, wherein the peptide is of unspecified length, thus, peptides, oligopeptides, polypeptides, and proteins are included within the present definition. This term also includes post expression modifications of the polypeptide, for example, glycosylations, acetylations, phosphorylations and the like. Included within the definition are, for example, peptides containing one or more analogues of an amino acid or labeled amino acids and peptidomimetics. Preferably, the IBTs are comprised of L-amino acids.

As used herein, the terms "protein of interest", "polypeptide of interest", "peptide of interest", "targeted protein", "targeted polypeptide", "targeted peptide", "expressible protein of interest", and "expressible polypeptide of interest" are used interchangeably to refer to a protein, polypeptide, or peptide that is bioactive and may be expressed by the genetic machinery of a host cell. The peptide of interest may be abbreviated as "POI". The peptide of interest may be an affinity peptide, i.e., a peptide having a specific affinity for a defined substrate, of no more than 300 amino acids in length, preferably no more than 200 amino acids in length, more preferably no more than 100 amino acids in length, and most preferably no more than 50 amino acids in length. The affinity peptide of interest may be an affinity peptide selected from a combinatorially-generated library wherein the affinity peptide was selected using a display technique selected from the group consisting of phage display, yeast display, ribosome display, and mRNA display.

As used herein, the term "bioactive" or "peptide of interest activity" refers to the activity or characteristic associated with the peptide and/or protein of interest. The bioactive peptides may be used in a variety of applications including, but not limited to curative agents for diseases (e.g., insulin, interferon, interleukins, anti-angiogenic peptides (U.S. Pat. No. 6,815,426), and polypeptides that bind to defined cellular targets with the proviso that the peptide of interest is not an antibody or the Fab fragment of an antibody, such as receptors, channels, lipids, cytosolic proteins, and membrane proteins, peptides having antimicrobial activity, peptides having an affinity for a particular material, such as hair-binding polypeptides, skin-binding polypeptides, nail-binding polypeptides, tooth binding peptides, cellulose binding polypeptides, polymer-binding polypeptides, clay-binding polypeptides, and peptides that have an affinity for particular animal or plant tissues, for targeted delivery of benefit agents. In a preferred embodiment, the peptide of interest binds to a body surface such as skin, hair, nail, or teeth.

As used herein, the "benefit agent" refers to a molecule that imparts a desired functionality to the complex for a defined application. The benefit agent may be peptide of interest itself or may be one or more molecules bound to covalently or non-covalently, or associated with, the peptide of interest wherein the binding affinity of the targeted polypeptide is used to selectively target the benefit agent to the targeted material. The targeted polypeptide may comprise at least one region having an affinity for at least one target material, such as biological molecules, polymers, hair, skin, nail, clays, and other peptides and at least one region having an affinity for the benefit agent, such as pharmaceutical agents, pigments, conditioners, dyes, fragrances, and the like. The peptide of interest may comprise a plurality of regions having an affinity for the target material and a plurality of regions having an affinity for the benefit agent. The peptide of interest may comprise at least one region having an affinity for a targeted material and a plurality of regions having an affinity for a variety of benefit agents wherein the benefit agents may be the same of different. Examples of benefits agents may include, but are not limited to conditioners for personal care products, pigments, dyes, fragrances, pharmaceutical agents (e.g., targeted delivery of cancer treatment agents), diagnostic/labeling agents, ultraviolet light blocking agents (i.e., active agents in sunscreen protectants), and antimicrobial agents (e.g., antimicrobial peptides), to name a few. The benefit agent may be covalently attached to the affinity peptide using any number of chemical cross-linking techniques well-known in the art.

As used herein, the term "inclusion body" refers to an intracellular amorphous deposit comprising aggregated protein found in the cytoplasm of a cell. Peptides of interest that are typically soluble with the host cell and/or cell lysate can be fused to one or more of the present inclusion body tags to facilitate formation of an insoluble fusion protein. Alternatively, the peptide of interest may be partially insoluble in the host cell, but produced at relatively lows levels where significant inclusion body formation does not occur. As such, the formation of inclusion bodies will increase peptide production. Fusion of the peptide of interest to one or more inclusion body tags (IBTs) may be used to increase the amount of protein produced in the host cell. Formation of the inclusion body facilitates simple and efficient purification of the fusion peptide from the cell lysate using techniques well known in the art, such as centrifugation and filtration. The inclusion body tag may also comprise an effective number of cross-linkable cysteine residues useful for separating the IBT from the peptide of interest post cleavage into a mixture of peptide fragments with the proviso that the peptide of interest is devoid of cross-linkable cysteine residues. The fusion protein may include one or more cleavable peptide linkers used to separate the protein/polypeptide of interest from the inclusion body tag(s). The cleavable peptide linker can be cleaved chemically, e.g., acid hydrolysis, and/or enzymatically. A protease/peptidase may be used that preferentially recognizes an amino acid cleavage site and/or sequence within the cleavable peptide linker.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. When synthesizing a gene for improved expression in a host cell it is generally desirable to design the gene such that its frequency of codon usage approaches the frequency of preferred codon usage of the host cell.

As used herein, the term "solubility" refers to the amount of a substance that can be dissolved in a unit volume of a liquid under specified conditions. The term "solubility" may also be used to describe the ability of a peptide—inclusion body tag, peptide of interest, or fusion peptides—to be dissolved in a volume of solvent, such as a biological buffer, under specified conditions. The peptides targeted for production may be substantially soluble in the cell and/or cell lysate under normal physiological conditions. Fusion of one or more inclusion body tags (IBTs) to the target peptide results in the formation of a fusion peptide that is insoluble under normal physiological conditions. The peptide of interest may be soluble in an aqueous matrix having a pH range of 5-12, preferably a pH of 6-10; and a temperature range of 5° C. to 50° C., preferably 10° C. to 40° C.

The term "amino acid" refers to the basic chemical structural unit of a protein or polypeptide. The following abbreviations are used herein to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid (or as defined herein) | Xaa | X |

As used herein, the term "gene" refers to a nucleic acid fragment that expresses a specific protein, including regulatory sequences preceding (5' non-coding sequences) and following (3' non-coding sequences) the coding sequence. The term "native gene" refers to a gene as found in nature with its own regulatory sequences The term "chimeric gene" refers to any gene that is not a native gene, comprising regulatory and/or coding sequences including coding sequences of fusion peptides that are not found together in nature. Accordingly, a chimeric gene may comprise regulatory sequences and coding sequences that are derived from different sources, or regulatory sequences and coding sequences derived from the same source, but arranged in a manner different than that found in nature. A "foreign" gene refers to a gene not normally found in the host organism, but that is introduced into the host organism by gene transfer.

As used herein, the term "genetic construct" refers to a series of contiguous nucleic acids useful for modulating the genotype or phenotype of an organism. Non-limiting examples of genetic constructs include but are not limited to a nucleic acid molecule, and open reading frame, a gene, a plasmid and the like.

As used herein, the term "mutagenic procedure" refers to any procedure or process capable of introducing a genetic alteration or mutation within the host cell and may include any process that results in an addition, deletion, or substitution to the genetic material within the host cell. Examples of mutagenic procedures may include, but are not limited to error-prone PCR, DNA shuffling, site-directed mutagenesis, transposon mutagenesis, recombinant DNA expression, random mutagenesis such as chemical mutagenesis, ultraviolet radiation, ionizing radiation, spontaneous mutations, and the like, promoter replacement, alterations in gene copy number, antisense expression, and down-regulation/disruption of endogenous gene expression, to name a few. The effect of the mutagenic procedure may be measured by the relative level of fluorescence detected. The recombinant prokaryotic cells exhibiting increased fluorescence after being subjected to a mutagenic procedure may be selected as the preferred subpopulation using FACS.

As used herein, the term "host cell" refers to cell that has been transformed or transfected or is capable of being transformed or transfected with an exogenous polynucleotide sequence. The present process is directed to the use of a recombinant prokaryotic host cell to produce a fusion peptide comprising a tetracysteine tag. The recombinant prokaryotic host cell may preferably be a bacteria, preferably an enteric bacteria, and most preferably *Escherichia coli*.

As used herein, the term "subpopulation" refers to a portion of the total cells analyzed and selected by the present process. Typically, a "subpopulation" of the cells is selected from the total population of cells analyzed by FACS based on a specified selection criteria measured by the instrument. The subpopulation may be selected based on the measured fluorescence, preferably those cells exhibiting relatively higher fluorescence within the total population of cells. The selected population of cells typically undergoes repeated rounds of growth, expression, labeling/detection, and selection in order to obtain cells with the highest fluorescence. The repeated process further may include at a least one additional step capable of introducing at least one genetic alteration to the host cell using a mutagenic procedure. Additional parameters such as cell size, cell shape, or inclusion body content may also be included (in addition to fluorescence) in the selection criteria.

As used herein, the terms "plasmid", "vector" and "cassette" refer to an extrachromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "binding affinity" refers to the strength of the interaction of a binding peptide with its respective substrate. The binding affinity can be defined or measured in terms a dissociation constant ($K_D$), and $MB_{50}$ value. In one embodiment, the binding affinity is determined in terms of the $MB_{50}$ value using an ELISA-based binding assay.

The term "$MB_{50}$" refers to the concentration of the binding peptide that gives a signal that is 50% of the maximum signal obtained in an ELISA-based binding assay. The $MB_{50}$ provides an indication of the strength of the binding interaction or affinity of the components of the complex. The lower the value of $MB_{50}$, the stronger the interaction of the peptide with its corresponding substrate.

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5$^{th}$ Ed. Current Protocols and John Wiley and Sons, Inc., N.Y., 2002.

Inclusion Body Tags

Fusion proteins comprising a carrier protein tag ("inclusion body fusion partner") that facilitates the expression of insoluble proteins are well-known in the art. The art typically uses inclusion body fusion partners, also referred to herein as "inclusion body tags", "IBTs" or "solubility tags", that are quite large, increasing the likelihood that the fusion protein will be insoluble. Example of large peptide tags typically used include, but are not limited to chloramphenicol acetyltransferase (Dykes et al., *Eur. J. Biochem.*, 174:411 (1988), β-galactosidase (Schellenberger et al., *Int. J. Peptide Protein Res.*, 41:326 (1993); Shen et al., *Proc. Nat. Acad. Sci. USA* 281:4627 (1984); and Kempe et al., *Gene*, 39:239 (1985)), glutathione-S-transferase (Ray et al., *Bio/Technology*, 11:64 (1993) and Hancock et al. (Int'l App. Pub. No. WO94/04688)), the N-terminus of L-ribulokinase (U.S. Pat. No. 5,206,154 and Lai et al., *Antimicrob. Agents & Chemo.*, 37:1614 (1993), bacteriophage T4 gp55 protein (Gramm et al., *Bio/Technology*, 12:1017 (1994), bacterial ketosteroid isomerase (KSI) protein (Kuliopulos et al., *J. Am. Chem. Soc.* 116:4599 (1994) and U.S. Pat. No. 5,648,244), ubiquitin (Pilon et al., *Biotechnol. Prog.*, 13:374-79 (1997), bovine prochymosin (Haught et al., *Biotechnol. Bioengineer.* 57:55-61 (1998), and bactericidal/permeability-increasing protein ("BPI"; Better, M. D. and Gavit, P D., U.S. Pat. No. 6,242, 219). The art is replete with specific examples of this technology, see for example U.S. Pat. No. 6,613,548, describing fusion protein of proteinaceous tag and a soluble protein and subsequent purification from cell lysate; U.S. Pat. No. 6,037, 145, teaching a tag that protects the expressed chimeric protein from a specific protease; U.S. Pat. No. 5,648,244, teaching the synthesis of a fusion protein having a tag and a cleavable linker for facile purification of the desired protein; and U.S. Pat. No. 5,215,896; U.S. Pat. No. 5,302,526; U.S. Pat. No. 5,330,902; and U.S. Pat. App. Pub. No. 2005/0221444, describing fusion tags containing amino acid compositions specifically designed to increase insolubility of the chimeric protein or peptide.

Shorter inclusion tags have recently been developed from the *Zea mays* zein protein (co-pending and commonly owned U.S. Pat. App. No. 11/641,936), the *Daucus carota* cystatin protein (co-pending and commonly owned U.S. patent application Ser. No. 11/641,273), and an amyloid-like hypothetical protein from *Caenorhabditis elegans* (co-pending and commonly owned U.S. patent application Ser. No. 11/516, 362; SEQ ID NOs: 171-218). The use of short inclusion body tags increases the total amount of the target peptide produced.

A family of small inclusion body tags was recently developed from amyloid-like proteins having amyloid fibrillar morphologies and often exhibit β-sheet tape architecture. An 11 amino acid synthetic peptide (i.e. peptide "PII-2"; also known as peptide "DN1") capable of self-assembly into β-sheet tapes, ribbons, fibrils, and fibers in water has been described (Aggeli et al., *J. Amer. Chem. Soc.*, 125:9619-9628 (2003); Aggeli et al., *PNAS*, 98(21):11857-11862 (2001); Aggeli et al., *Nature*, 386:259-262 (1997); and Aggeli et al., *J. Mater Chem*, 7(7):1135-1145 (1997). The P11-2 peptide served as the core sequence for the preparation of a family of structurally-related inclusion body tags; including IBT139 and IBT139.CCPGCC (SEQ ID NO:2) (See co-pending and commonly owned U.S. patent application Ser. No. 11/782, 836). This family of structurally-related inclusion body tags comprising at least two copies of the core sequence Gln-Gln-Xaa1-Phe-Xaa2-Trp-Xaa3-Phe-Xaa4-Xaa5-Gln (SEQ ID NO: 17), wherein Xaa1=Arg, His, or Lys; Xaa2=Gln, His, or Lys; Xaa3=Gln, His, or Lys; Xaa4=Glu or Gln; and Xaa5=Gln or Lys. IBT139 (SEQ ID NOs: 11 and 12) was used in the present examples to prepare a tetracysteine tagged inclusion body tag (IBT139.CCPGCC; SEQ ID NOs: 13 and 14).

Figure 1A:
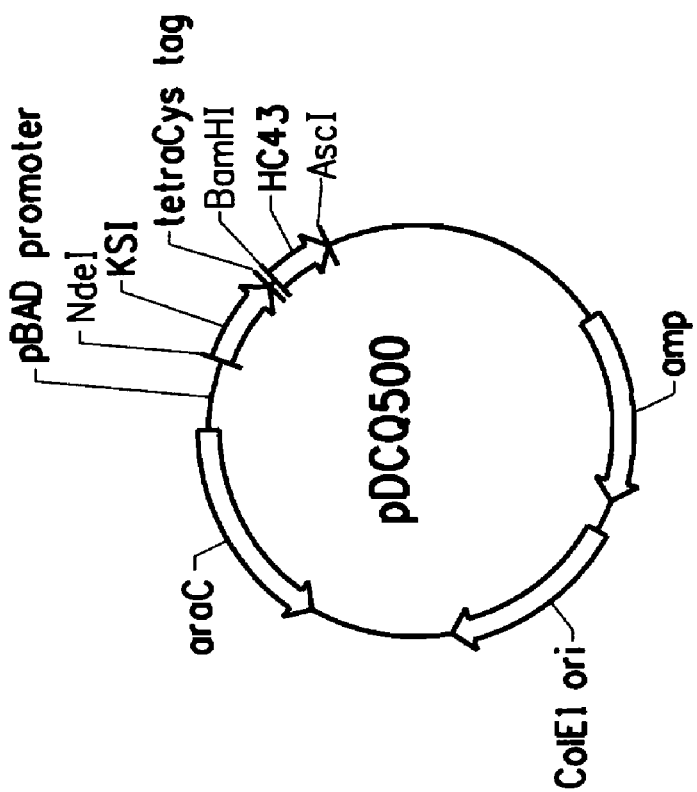

An additional inclusion body tag derived from ketosteroid isomerase ("KSI"; Kuliopulos et al., *J. Am. Chem. Soc.* 116: 4599 (1994) and U.S. Pat. No. 5,648,244) is also used in the present examples. The modified KSI derivative, referred to herein as "KSI(C4)" (SEQ ID NOs: 15 and 16), has been previously reported in co-pending and commonly owned U.S. patent application Ser. Nos. 11/512,910; 11/514,804; and 11/389,948; and U.S. Pat. App. Nos. 60/869,363; 60/855,251; and 60/857,105). The KSI(C4) tag comprises an effective number of cross-linkable cysteine residues that enable separation of the solubility tag from the peptide of interest by oxidative cross-linking (see co-pending and commonly owned U.S. patent application Ser. No. 12/172,395). As illustrated in the present examples, the KSI(C4) inclusion body was modified to include a tetracysteine tag (SEQ ID NO: 2) on the C-terminal end of the tag (FIG. 1A, pDCQ500 (SEQ ID NO: 23)).

An acid-resistance version of the KSI(C4) tag ["KSI(C4) E"] has recently been reported in co-pending and commonly owned U.S. patent application Ser. No. 12/172,385 and is provided as SEQ ID NO: 219.

Expressible Peptides/Proteins of Interest—Large Peptides/Proteins

The process described herein may be used to in vivo label and identify any tetracysteine-tagged peptide, polypeptide or protein recombinantly produced in an unpermeabilized prokaryotic host cell. Construction and expression of suitable genetic constructs is well-known in the art. The genetic construct may be designed so that at least one tetracysteine tag is operably linked to the N- or C-terminus of the peptide/protein and may also be incorporated internally into the peptide/ protein of interest. The chimeric genetic construct may be designed so that the tetracysteine tag is operably linked to the N- or C-terminus of the peptide/protein to be expressed and labeled.

Expressible Peptides of Interest—Short Peptides of Interest Produced in the Form of Fusion Peptides As described herein, the peptide of interest ("expressible peptide") targeted for production using the present process is one that is substantially soluble in the host cell and/or host cell liquid lysate under normal physiological conditions. The peptide of interest may generally be small, often less than 500 amino acids in length, and difficult to produce in sufficient amounts due to endogenous proteolytic degradation. Fusion of the peptide of interest to at least one solubility tag creates a fusion peptide that is insoluble in the host cell and/or host cell lysate under normal physiological conditions. Production of the peptide of interest is typically increased when expressed and accumulated in the form of an insoluble inclusion body as the peptide is generally more protected from proteolytic degradation. Furthermore, the insoluble fusion protein can be easily separated from the host cell lysate using any number of simple separation techniques, such as centrifugation and/or filtration. The peptide of interest may be produced in the form of a fusion peptide. The fusion peptide may be an insoluble fusion peptide that accumulates in the host cell in the form of inclusion bodies.

The length of the peptide of interest may vary as long as (1) the peptide is appreciably soluble in the host cell and/or cell lysate, and/or (2) the amount of the targeted peptide produced is significantly increased when expressed in the form of an insoluble fusion peptide/inclusion body (i.e. expression in the form of a fusion protein protect the peptide of interest from proteolytic degradation). The peptide of interest can be no more than 500 amino acids in length, preferably no more than 300 amino acids in length, more preferably less than 200 amino acids in length, even more preferably less than 100 amino acids in length, even more preferably less than 75 amino acids in length, yet even more preferably less than 50 amino acids in length, and most preferably less than 30 amino acids in length.

The function of the peptide of interest is not limited by the process described herein and may include, but is not limited to bioactive molecules such as curative agents for diseases (e.g., insulin, interferon, interleukins, peptide hormones, anti-angiogenic peptides, and peptides with the proviso that the peptide is not an antibody or an Fab portion of an antibody that bind to and affect defined cellular targets such as receptors, channels, lipids, cytosolic proteins, and membrane proteins (see U.S. Pat. No. 6,696,089), peptides having an affinity for a particular material, e.g., biological tissues/body surfaces such as hair-binding peptides (U.S. patent application Ser. No. 11/074,473; Int'l Pat. App. No. WO 0179479; U.S. Pat. App. Pub. No. 2002/0098524; U.S. Pat. App. Pub. No. 2003/0152976; Int'l App. Pub. No. WO 04048399; U.S. patent application Ser. No. 11/512,910; U.S. patent application Ser. No. 11/516,362; and U.S. patent application Ser. No. 11/696,380), skin-binding peptides (U.S. patent application Ser. No. 11/069,858; Int'l App. Pub. No. WO 2004/000257; U.S. patent application Ser. No. 11/516,362; and U.S. patent application Ser. No. 11/696,380), nail-binding peptides (U.S. patent application Ser. No. 11/074,473; U.S. patent application Ser. No. 11/696,380)) and peptides having specific affinity for other materials such as cellulose-binding peptides, polymer-binding peptides (U.S. patent application Ser. Nos. 11/607,723, 11/607,792, 11/607,734, 11/607,672, and 11/607,673), and clay-binding peptides (U.S. patent application Ser. No. 11/696,380), for targeted delivery of at least one benefit agent (see U.S. Pat. No. 7,220,405; U.S. patent application Ser. No. 11/074,473; and U.S. patent application Ser. No. 11/696,380).

The peptide of interest may be a single-stranded affinity peptide derived from a combinatorially-generated library. Preferably, the affinity peptide may be no more than 300 amino acids in length. The affinity peptide may have a binding affinity for a target substrate, as measured by $MB_{50}$ values, of less than or equal to about $10^{-5}$ M, less than or equal to about $10^{-6}$ M, less than or equal to about $10^{-7}$ M, less than or equal to about $10^{-8}$ M, preferably less than or equal to about $10^{-9}$ M, and more preferably less than or equal to about $10^{-10}$ M.

The affinity peptide may be selected from the group consisting of hair-binding peptides, nail-binding peptides, skin-binding peptides, tooth-binding peptides, pigment binding peptides, cellulose-binding peptides, polymer-binding peptides, and clay-binding peptides.

The peptide of interest may preferably comprise a body surface-binding peptide comprising at least one body surface-binding moiety. The hair-binding peptide may be selected from the group consisting of SEQ ID NOs: 8, 10, and 26-49. The skin-binding peptide may be selected from the group consisting of SEQ ID NOs: 50-62. The nail-binding peptide may be selected from the group consisting of SEQ ID NOs: 63 and 64. The polymer-binding peptide may be selected from the group consisting of SEQ ID NOs: 126-153. The pigment-binding peptide may be selected from the group consisting of SEQ ID NOs: 94-119. The cellulose-binding peptide may be selected from the group consisting of SEQ ID NOs: 120-125. The clay-binding peptide may be selected from the group consisting of SEQ ID NOs: 154-169. The peptide of interest may be a multi-block hair-binding peptide (see U.S. patent application Ser. Nos. 11/074,473 and 11/389,948).

The peptide of interest may have antimicrobial activity. The antimicrobial peptide may be selected from the group consisting of SEQ ID NOs: 65-93.

Multi-block hair binding peptides HC77643 (referred to herein as "HC43") and HC776124 (also referred to herein as "HC124") have been described previously. Both peptides are used herein as examples of suitable peptides of interest, although the present process may be used to measure any recombinant prokaryotic cells comprising a TC-tagged peptide. The peptide of interest may be an affinity peptide having a specific affinity for a body surface (e.g. skin, eye, oral, hair, teeth, etc.). The peptide of interest may be an affinity peptide identified by biopanning against a combinatorially-generated library. Preferably the affinity peptide is identified using a biopanning technique selected from the group consisting of phage display, yeast display, ribosome display, and mRNA display.

The two multi-block hair-binding peptides were designed with the following amino acid sequences. Construction of multi-block hair binding peptides have been reported (see co-pending and commonly owned U.S. patent application Ser. Nos. 11/389,948 and 11/074,473). Each of the multi-block hair binding peptides comprises one or more hair binding domains. The functional binding domains are provided in Table 1. Hair-binding domains (bold) include A09 (IPW-WNIRAPLNA; SEQ ID NO: 5) and KF11 (NTSQLST; SEQ ID NO: 6). The affinity domains with the multi-block peptides are typically separated by short peptide spacers. The DP acid cleavable moieties are italicized.

TABLE 1

Multi-block affinity peptides used in the present examples.

| Peptide Name | Formula (Functional Binding Domains in Bold) | Amino acid Sequence | Nucleic acid SEQ ID NO: | Amino Acid SEQ ID NO: |
|---|---|---|---|---|
| HC77643 or "HC43" | GSDPG-A09-GAG-A09-GGSGPGSGG-KF11-GGG-KF11-GGPKK | GS*DP*GIPWWNIRAPLNAGAGIPWWNIRAPLNAGGSGPGSGGNTSQLSTGGGNTSQLSTGGPKK | 7 | 8 |
| HC776124 or "HC124" | GSD(PG-A09-GAG-A09-GGSGPGSGG-KF11-GGG-KF11-GGPKKPGD)$_2$ | GS*DP*GIPWWNIRAPLNAGAGIPWWNIRAPLNAGGSGPGSGGNTSQLSTGGGNTSQLSTGGPKKPGD*PG*IPWWNIRAPLNAGAGIPWWNIRAPLNAGGSGPGSGGNTSQLSTGGGNTSQLSTGGPKKPGD | 9 | 10 |

Affinity peptides are particularly useful to target benefit agents imparting a desired functionality to a target material (such as hair, skin, nail, or teeth) for a defined application (see U.S. Pat. No. 7,220,405; U.S. patent application Ser. No. 11/074,473; U.S. patent application Ser. No. 11/512,910; and U.S. patent application Ser. No. 11/696,380 for a list of typical benefit agents such as conditioners, pigments/colorants, fragrances, etc.). The benefit agent may be a peptide of interest itself or may be one or more molecules bound to (covalently or non-covalently), or associated with, the peptide of interest wherein the binding affinity of the peptide of interest is used to selectively target the benefit agent to the targeted material. The peptide of interest may comprise at least one region having an affinity for at least one target material, such as, biological molecules, polymers, hair, skin, nail, other peptides, etc., and at least one region having an affinity for the benefit agent, such as, pharmaceutical agents, antimicrobial agents, colorants, dyes, pigments, polymer coated pigments, conditioners, dyes, fragrances, etc. The peptide of interest may comprise a plurality of regions having an affinity for the target material and a plurality of regions having an affinity for one or more benefit agents. The peptide of interest may comprise at least one region having an affinity for a targeted material and a plurality of regions having an affinity for a variety of benefit agents wherein the benefit agents may be the same of different.

Cleavable Peptide Linkers

The use of cleavable peptide linkers, i.e. cleavage sites or cleavage sequences, is well-known in the art. Cleavage peptide linkers are typically incorporated into the peptide/protein construct to facilitate downstream processing. A cleavable peptide linker may be used to separate the tetracysteine tag from the peptide/protein targeted for labeling.

The peptide of interest may also be a fusion peptide. Fusion peptides comprising the inclusion body tags will typically include at least one cleavable peptide sequence separating the inclusion body tag from the polypeptide of interest. The cleavable sequence facilitates separation of the inclusion body tag(s) from the peptide(s) of interest. Cleavage of the peptide linker is typically reserved for bulk processing of the fusion peptides obtained from the fermented cell biomass and should not be used for labeling and detection of the small aliquots of cells from shake flasks or from smaller scale fermentors, such as those described herein. However, the cleavable linker is typically incorporated into the constructs used in the present process. Preferred cells, such as those producing higher amounts of the desired peptide of interest as measured by the level of fluorescence, are identified and selected by the present process may undergo further modifications and/or labeling/selection cycles or may be directed towards a large scale fermentation process. As such, it is desirable to include a cleavable peptide linker in the fusion peptide construct even though a cleavage step, such as acid cleavage, will not typically be included when labeling and detecting cells using the present process.

The cleavable sequence may be provided by a portion of the inclusion body tag and/or the peptide of interest (e.g., inclusion of an acid cleavable aspartic acid-proline moiety). The cleavable sequence is provided by including (in the fusion peptide) at least one cleavable peptide linker between the inclusion body tag and the peptide of interest.

Means to cleave the peptide linkers are well-known in the art and may include chemical hydrolysis, enzymatic cleavage agents, and combinations thereof. One or more chemically cleavable peptide linkers may be included in the fusion construct to facilitate recovery of the peptide of interest from the inclusion body fusion protein. Examples of chemical cleavage reagents include cyanogen bromide (cleaves methionine residues), N-chloro succinimide, iodobenzoic acid or BNPS-skatole [2-(2-nitrophenylsulfenyl)-3-methylindole] (cleaves tryptophan residues), dilute acids (cleaves at aspartyl-prolyl bonds), and hydroxylamine (cleaves at asparagine-glycine bonds at pH 9.0); see Gavit, P. and Better, M., *J. Biotechnol.*, 79:127-136 (2000); Szoka et al., DNA, 5(1):11-20 (1986); and Walker, J. M., *The Proteomics Protocols Handbook*, 2005, Humana Press, Totowa, N.J.)). One or more aspartic acid-proline acid cleavable recognition sites, i.e., a cleavable peptide linker comprising one or more D-P dipeptide moieties, may be included in the fusion protein construct to facilitate separation of the inclusion body tag(s) form the peptide of interest. The fusion peptide may include multiple regions encoding peptides of interest separated by one or more cleavable peptide linkers.

One or more enzymatic cleavage sequences may be included in the fusion protein construct to facilitate recovery of the peptide of interest. Proteolytic enzymes and their respective cleavage site specificities are well known in the art. The proteolytic enzyme may be selected to specifically cleave only the peptide linker separating the inclusion body tag and the peptide of interest. Examples of enzymes useful for cleaving the peptide linker include, but are not limited to Arg-C proteinase, Asp-N endopeptidase, chymotrypsin, clostripain, enterokinase, Factor Xa, glutamyl endopeptidase, Granzyme B, *Achromobacter* proteinase I, pepsin, proline endopeptidase, proteinase K, Staphylococcal peptidase I, thermolysin, thrombin, trypsin, and members of the Caspase family of proteolytic enzymes (e.g. Caspases 1-10) (Walker, J. M., supra). An example of a cleavage site sequence is provided by SEQ ID NO: 170 (Caspase-3 cleavage site; Thornberry et al. *J. Biol. Chem.*, 272:17907-17911 (1997) and Tyas et al., *EMBO Reports*, 1(3):266-270 (2000)).

The cleavage step, which is typically reserved for bulk processing and not used for processing the small aliquot of the cells targeted for the present labeling and detection process, occurs after the insoluble inclusion bodies and/or insoluble fusion peptides have been isolated from the cell lysate. Inclusion body processing steps are described in co-owned U.S. patent application Ser. Nos. 12/172,385 and 12/172,395; each herein incorporated by reference. The cells can be lysed using any number of means well known in the art, e.g. mechanical and/or chemical lysis. Methods to isolate the insoluble inclusion bodies/fusion peptides from the cell lysate are well known in the art, e.g., centrifugation, filtration, and combinations thereof. Once recovered from the cell lysate, the insoluble inclusion bodies and/or fusion peptides can be treated with a cleavage agent (chemical and/or enzymatic) to cleave the inclusion body tag from the peptide of interest. The fusion protein and/or inclusion body may be diluted and/or dissolved in a suitable solvent prior to treatment with the cleavage agent. The cleavage step may also be omitted if the inclusion body tag does not interfere with the activity of the peptide of interest.

After the cleavage step, the peptide of interest can be separated and/or isolated from the fusion protein and the inclusion body tags based on a differential solubility of the components. Parameters such as pH, salt concentration, and temperature may be adjusted to facilitate separation of the inclusion body tag from the peptide of interest. In one embodiment, the peptide of interest is soluble while the inclusion body tag and/or fusion protein is insoluble in the defined process matrix (typically an aqueous matrix). In one embodiment, the peptide of interest is insoluble while the inclusion body tag is soluble in the defined process matrix.

Optionally, the peptide of interest may be further purified using any number of well known purification techniques in the art such as ion exchange, gel purification techniques, and column chromatography (see U.S. Pat. No. 5,648,244), to name a few.

Fusion Peptides

The methods described herein can be used to in vivo label and optionally detect prokaryotic cells comprising any peptides/proteins having at least one tetracysteine tag capable of binding at least one biarsenical labeling reagent. The tetracysteine-tagged peptide is preferably a fusion peptide. The fusion peptides will include at least one inclusion body tag (IBT) operably linked to at least one peptide of interest (POI). Typically, the fusion peptides will also include at least one cleavable peptide linker (CL) having a cleavage site between the inclusion body tag and the peptide of interest. The inclusion body tag may include a cleavage site whereby inclusion of a separate cleavable peptide linker may not be necessary. The cleavage method may be chosen to ensure that the peptide of interest is not adversely affected by the cleavage agent(s) employed.

Any portion of the fusion peptide may contain at least one tetracysteine tag. The tetracysteine tag may be separated from the portion of the fusion protein comprising the peptide of interest by at least one at least one cleavable peptide linker. The tetracysteine tag may be operably-linked to the portion of the fusion peptide encoding the inclusion body tag. The portion of the fusion peptide comprising the IBT-TC tag may be separated from the POI by at least one cleavage peptide linker.

One of skill in the art will recognize that the fusion protein can be structured in a variety of ways. Typically, the fusion protein will include at least one IBT, at least one peptide of interest (POI), and at least one cleavable peptide linker (CL) comprising a cleavage site located between the IBT and the POI. The inclusion body tag may be organized as a leader sequence or a terminator sequence relative to the position of the peptide of interest within the fusion peptide. A plurality of IBTs, POIs, and CLs may be used when engineering the fusion peptide. The fusion peptide may include a plurality of IBTs, POIs, and cleavable peptide linkers that are the same or different.

The fusion peptide may comprise the following formula:

IBT-TC-CL-POI or POI-CL-TC-POI wherein

IBT is at least one inclusion body tag;

TC is at least one tetracysteine tag;

CL is at least one cleavable peptide linker; and

POI is at least one peptide of interest.

The cleavable peptide linker may comprise an acid cleavable aspartic acid-proline moiety (DP).

The fusion peptide is typically insoluble in an aqueous matrix at a temperature of 10° C. to 50° C., preferably 10° C. to 40° C. The aqueous matrix typically comprises a pH range of 5 to 12, preferably 6 to 10, and most preferably 6 to 8. The temperature, pH, and/or ionic strength of the aqueous matrix may be adjusted to obtain the desired solubility characteristics of the fusion peptide/inclusion body.

In Vivo Tetracysteine Tag Labeling Using a Biarsenical Labeling Reagent

Tetracysteine tags comprising the sequence (CCXXCC; SEQ ID NO: 1) are capable of covalently binding biarsenical labeling reagents wherein the sequence CCPGCC (SEQ ID NO: 2) is preferred. Examples of suitable biarsenical labeling reagents are known in the art and include, but are not limited to FlAsh-EDT$_2$, ReAsh-EDT$_2$, and CHoXAsh-EDT$_2$; available as the LUMIO™ detection system from Invitrogen Corp.; Carlsbad, Calif.; Adams et al., supra). Use of the LUMIO™ protein detection system has been reported in the art (U.S. Pat. No. 5,932,474; U.S. Pat. No. 6,054,271; U.S. Pat. No. 6,831,160; U.S. Pat. No. 6,008,378; U.S. Pat. No. 6,451,564; U.S. Pat. No. 6,686,458; U.S. Pat. No. 7,138,503; EP1032837B1, EP1684073A2, U.S. Pat. App. Pub. No. 20050176065 A1; Griffin et al., 1998, supra; Griffin et al., 2000, supra; Ho and Starnbach, supra; Adams et al., supra; Stroffekova and Proenza, supra; Rice et al., supra; and Int'l App. Pub. No. WO2007/023184A1).

However, in vivo labeling of prokaryotic host cells (Ignatova and Gierasch, et al., *PNAS* 101(2):523-528 (2004)) typically requires extensive dye incubation times (for example, at least 4 hours) and high concentrations (e.g., 150 µM to 1 mM) of the biarsenical labeling reagent in combination with a pretreatment step (lysozyme) to increase cell wall permeability to the labeling reagent or the presence of β-mercaptoethanol (Griffin et al., 2000, supra).

The process described herein does not require a lengthy labeling period, pretreatment with a permeabilizing agent (e.g. lysozyme, toluene), or the presence of an undesirable compound, such as β-mercaptoethanol. The present process may detect and select the labeled prokaryotic cells using a fluorescence activated cell sorter (FACS). In one embodiment, subpopulations of in vivo-labeled fluorescent cells (from the larger population of cells analyzed by FACS) are selected based on increased/higher levels of fluorescence.

Suitable labeling conditions typically include labeling approximately $10^6$ to about $10^7$ of properly induced bacterial cells in the fresh growth medium or PBS (phosphate buffered saline) with a suitable amount of biarsenical labeling reagent at a temperature typically ranging from about 10° C. to about 40° C., preferably about 22° C. (typical room temperature) for a period of time ranging from about 1 to less than 4 hours, and preferably about 1.5 hours to about 2 hours. The labeling period is typically conducted under low light conditions, preferably in the dark. The amount of biarsenical labeling reagent used is less than 150 µM, preferably about 5 µM to less than 150 µM, more preferably about 5 µM to about 100 µM, even more preferably 10 µM to about 50 µM, and most preferably about 10 µM to about 20 µM.

Typically, the TC-tagged peptide is under the control of an inducible expression system, such as an arabinose-inducible expression system. An effective amount of the inducer (for example, 0.2% L-arabinose for a pBAD-based expression system) is added to the media to produce the TC-tagged peptide of interest. The period of time between induction and labeling with the biarsenical labeling reagent may vary, but is typically about 5 minutes to less than 6 hours, wherein about 2.5 hours to about 4.5 hours is preferred. The biarsenical labeling reagent may be included with the inducer wherein labeling of the TC-tagged peptide occurs as the peptide is produced.

The optical density of the cells ($OD_{600}$) at time of induction may vary, but typically ranges from 0.01 to about 5 prior to induction, wherein a value of 0.1 to 2 is preferred. In a preferred embodiment, the optical density ($OD_{600}$) value at induction is about 0.5. The number of cells is typically normalized prior to labeling to account for difference in optimal density ($OD_{600}$) between different samples. The normalized cell numbers typically range from $10^4$ to about $10^8$ cells, wherein about approximately $10^5$ to about $10^7$ of induced bacterial cells is preferred.

The labeling conditions specifically excludes, by proviso, the use of permeabilizing agents, such as lysozyme pretreatment or toluene treatment or the use of undesirable compounds, such as β-mercaptoethanol and/or other reducing agents. Pretreatments and the use of undesirable compounds increase cost and complexity to the process and may induce undesirable stress-related changes to the recombinant prokaryotic cell and/or adversely affect the labeling efficiency. The appropriate antibiotics and inducer in the labeling reaction can be maintained during the labeling process.

Detection and Isolation of In Vivo Labeled Cells Using FACS

A process is provided that combines in vivo labeling with detection and isolation of the preferred subpopulation of cells using a fluorescence activated cell sorter (FACS; Becton Dickinson). Specifically, a Becton Dickinson FACSVantage™ flow cytometry system can be used to identify, sort, and/or isolate recombinant E. coli cells comprising the fluorescently-labeled fusion peptides.

Int'l App. Pub. No. WO2007/023184A1 to Dupraz et al. describes the use of a FACS to select and identify eukaryotic cells (mammalian cell lines) expressing a chimeric selection marker comprising a tetracysteine tag (TC). However, Dupraz et al. do not describe a process to in vivo label nor identify prokaryotic cells expressing a fusion peptide comprising a tetracysteine tag (TC). No methods have been reported that describe the use of FACS to isolate prokaryotic cells expressing peptides comprising a tetracysteine tag labeled by a biarsenical labeling reagent.

Suitable FACS system parameters used to detect and sort the fluorescent cells can be determined by one of skill in the art. The excitation and emission maxima for the biarsenical dyes used in the present process are known and are described above.

FACS may be used to select a subpopulation of cells exhibiting higher fluorescence from the population of cells analyzed. The higher fluorescence is proportional to increased fusion peptide production. The process enables the identification and isolation of recombinant prokaryotic cells exhibiting increased fusion peptide production. The selected subpopulation of cells can undergo multiple rounds of selection to isolation those cells exhibiting the highest levels of fusion peptide production.

The selection parameters/criteria used to isolate a desired subpopulation using FACS may vary. Typically, the subpopulation comprises cells exhibiting the highest fluorescence with the total population assayed. In one embodiment, the top 50% of the total population of cells exhibiting fluorescence are selected (i.e. the "subpopulation"), preferably the top 25%, more preferably the top 10%, more preferably the top 5%, even more preferably the top 1%, yet even more preferably the top 0.5%, and most preferably the top 0.1%. Typically, at least 20,000-50,000 events (cells) are analyzed to set up the gates for sorting. The sorted events may vary depending upon the population of the cells available.

Evolution and Selection of Improved Production Hosts

Described herein is a process for labeling, detecting, and isolating subpopulations of live cells exhibiting improved fusion peptide production. The methods are repeatable and may be used to identify recombinant prokaryotic cells having higher and/or improved levels of recombinant fusion peptide production. The present process may include subjecting one or more of the viable recombinant prokaryotic host cells from a selected subpopulation to a procedure capable of inducing a genetic alteration (i.e., a mutagenic procedure). The mutants having beneficial mutations, such as those increasing fusion peptide production, may be isolated by repeating the present process. The process may include, for example, (1) growing the pool of mutated recombinant prokaryotic cells, (2) inducing expression of the chimeric construct whereby a fusion peptide comprising the tetracysteine tag is produced, (3) labeling the fusion peptide in vivo with a biarsenical labeling reagent, (4) detecting/isolating a subpopulation of the labeled recombinant prokaryotic host cells exhibiting increased fluorescence, and (5) amplifying the isolated cells by growing in liquid medium or on plates, optionally repeating steps (1) through (5).

Means to introduce a genetic modification to a host cell are well known in the art and may include any process that results in at least one insertion, deletion, or substitution and combinations of these to the chromosomal and/or extrachromosomal DNA within the host cell and may include mutations to one or more genes and/or portions of one or more genes (e.g. coding sequences, promoters, regulatory elements, etc.). The genetic modifications can be introduced using random or targeted mutagenesis. The genetic modification may be a disruption to an endogenous gene with the proviso that the disrupted gene is not an essential gene. For example, the genetic modification may be an insertion of a foreign gene or fragment thereof; it may be a replacement of an endogenous promoter with a heterologous promoter characterized by increased or decreased expression levels relative to the activity of the endogenous promoter; or it may be any mutation that changes relative level of transcription, translation, and/or function of a host cell gene.

Techniques for gene disruption/down-regulation are common and well known in the art of molecular biology. When the sequence of the gene to be disrupted is known, one of the most effective methods for gene down regulation is targeted gene disruption where foreign DNA is inserted into a structural gene so as to disrupt transcription. This can be accomplished by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell (Hamilton et al. (1989) *J. Bacteriol.* 171:4617-4622, Balbas et al. (1993) *Gene* 136:211-213, Gueldener et al. (1996) *Nucleic Acids Res.* 24:2519-2524, and Smith et al. (1996) *Methods Mol. Cell. Biol.* 5:270-277).

Whole genome sequences are available for many commercially important prokaryotic production hosts, especially bacterial strains like *Escherichia coli* (Baba et al., *Molecular Systems Biology*, article number 2006.0008, page 1-11 (2006); Blattner et al., *Science,* 277:1453-1462 (1997)). One of skill in the art may use targeted insertion of a nucleic acid molecule to alter the host cell. Intergenic regions between known gene clusters may be useful site when inserting an entire gene or gene cluster. Furthermore, one of skill in the art may use targeted promoter replacement to exchange promoters of varying strength to optimize the desired expression levels of certain genes (see, for example, U.S. patent application Ser. No. 10/734,936).

The λ-Red recombinase system may be used to selectively insert, disrupt and/or down-regulate expression of the desired gene. The λ-Red system works particularly well in *E. coli* and is very effective for targeted genetic modifications. Typically, a linear nucleic acid molecule encoding a selectable marker, such as kanamycin, is flanked by site specific recombination sequences. The linear nucleic acid molecule is designed to include sequences flanking the site specific recombination sites that have significant homology to the chromosomal gene targeted for disruption. Transformation of the construct (typically linear double stranded DNA) in the presence of the λ-Red recombinase system often results in the disruption of the targeted gene. Transformants harboring the disrupted gene are selected based on the selectable marker. A site-specific recombinase may then used (typically expressed from a curable plasmid such as pCP20; U.S. patent application Ser. No. 10/734,936) to remove the marker. Removal of the marker can be for regulatory compliance and/or to enable targeted disruption of additional genes using the same marker.

Antisense technology is another method of down-regulating genes where the sequence of the target gene is known. To accomplish this, a nucleic acid segment from the desired gene is cloned and operably-linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. A person skilled in the art will appreciate that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence based. For example, cells may be exposed to UV radiation and then screened for the desired phenotype. Mutagenesis with chemical agents is also effective for generating mutants and commonly used substances include chemicals that affect non-replicating DNA such as $HNO_2$ and $NH_2OH$, as well as agents that affect replicating DNA such as acridine dyes, notable for causing frame-shift mutations. Specific methods for creating mutants using radiation or chemical agents are well documented in the art.

Another non-specific method of random gene insertion or random disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element). Transposon-mediated random insertion in the chromosome can be used for isolating mutants for any number of applications including enhanced production of any number of desired products including enzymes or other proteins, amino acids, or small organic molecules, such as alcohols.

Process to Detect a Prokaryotic Host Cell Having Improved Biarsenical Labeling

Depending on the cell wall/membrane structure and the intracellular environment, it may be more difficult to perform live cell labeling of certain bacteria. FACS sorting can also be used to isolate prokaryotic host cells having improved biarsenical labeling. For example, certain host mutations may increase cell permeability to facilitate the biarsenical dye to enter the cell or to improve the binding of the biarsenical dye to the target sequence. Using a library of host cells containing various mutations, it is possible to isolate the prokaryotic host mutants, which showed improved labeling efficiency. Those prokaryotic host cells may be used for future experiments that involve biarsenical labeling. The isolated mutants with increased permeability may be useful for labeling with other dyes or for other applications.

Transformation and Expression

Construction of expression cassettes and vectors suitable for use in a prokaryotic expression host is common and well known in the art. Typically, the vector or cassette contains sequences directing transcription and translation of the relevant chimeric gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Transcription initiation control regions or promoters, which are useful to drive expression of the genetic constructs encoding the fusion peptides in the desired host cell, are numerous and familiar to those skilled in the art. Virtually any promoter capable of driving these constructs is suitable including, but not limited to lac, ara (pBAD), tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary; however, it is most preferred if included.

Preferred host cells for expression of the present fusion peptides are prokaryotic expression hosts found within the archaea and bacterial domains and which grow over a wide range of temperature, pH values, and solvent tolerances. For example, it is contemplated that any bacteria may be suitable hosts for expression of the present nucleic acid molecules encoding the fusion peptides. Transcription, translation, and the protein biosynthetic apparatus are universal cell process and genes are expressed regardless of the carbon feedstock used to generate the cellular biomass. Large-scale microbial growth and functional gene expression may utilize a wide range of simple or complex carbohydrates, organic acids and alcohols (i.e. methanol), saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include, but are not limited to bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus*. Preferred bacterial host strains include *Escherichia, Pseudomonas,* and *Bacillus*. The bacterial host strain may be *Escherichia coli*. The bacterial host strain may be derived from *Escherichia coli* MG 1655 (ATCC 47076 ™).

Fermentation Media

The fermentation media should contain a suitable carbon substrate. Suitable substrates include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally, the carbon substrate may also be one-carbon substrates such as carbon dioxide, or methanol for which metabolic conversion into key biochemical intermediates has been demonstrated. The source of carbon may include a wide variety of carbon containing substrates and is limited only by the choice of organism.

Although contemplated that all of the above mentioned carbon substrates and mixtures of these are suitable, preferred carbon substrates are glucose, fructose, and/or sucrose.

In addition to an appropriate carbon source, fermentation media must contain suitable minerals, salts, cofactors, buffers and other components, known to those skilled in the art, suitable for the growth of the cultures and promotion of the expression of the present fusion peptides.

Culture Conditions

Suitable culture conditions can be selected dependent upon the chosen production host. Typically, cells are grown at a temperature in the range of about 25° C. to about 40° C. in an appropriate medium. Suitable growth media may include common, commercially-prepared media such as Luria Bertani (LB) broth. Other defined or synthetic growth media may also be used and the appropriate medium for growth of the particular microorganism will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are typically between pH 5.0 to pH 9.0, where pH 6.0 to pH 8.0 is preferred.

Fermentations may be performed under aerobic or anaerobic conditions where aerobic conditions are generally preferred.

Industrial Batch and Continuous Fermentations

A classical batch fermentation is a closed system where the composition of the medium is set at the beginning of the fermentation and not subject to artificial alterations during the fermentation. Thus, at the beginning of the fermentation the medium is inoculated with the desired organism or organisms, and fermentation is permitted to occur without adding anything to the system. Typically, a "batch" fermentation is in respect to the addition of carbon source and attempts are often made at controlling factors such as pH and oxygen concentration. In batch systems the metabolite and biomass compositions of the system change constantly up to the time the fermentation is stopped. Within batch cultures, cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass. (hereinafter "Brock"), or Deshpande, Mukund V., *Appl. Biochem. Biotechnol.*, 36:227-234 (1992).

Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to the medium being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra. It is contemplated that the present process may be practiced using batch, fed-batch or continuous processes and that any known mode of fermentation would be suitable.

When an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples.

The meaning of abbreviations used is as follows: "min" means minute(s), "h" means hour(s), "μL" means microliter(s), "mL" means milliliter(s), "L" means liter(s), "nm" means nanometer(s), "mm" means millimeter(s), "μm" means micrometer(s), "μM" means micromolar, "mM" means millimolar, "M" means molar, "mmol" means millimole(s), "μmol" means micromole(s), "pmol" means picomole(s), "g" means gram(s), "μg" means microgram(s), "mg" means milligram(s), "g" means the gravitation constant, "rpm" means revolutions per minute, and "cat#" means catalog number.

General Methods

Standard recombinant DNA and molecular cloning techniques used herein are well known in the art and are described by Sambrook, J. and Russell, D., *Molecular Cloning: A Laboratory Manual*, Third Edition, Cold Spring Harbor Laboratory Press, Cold Spring Harbor, N.Y. (2001); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et. al., *Short Protocols in Molecular Biology*, 5th Ed. Current Protocols and John Wiley and Sons, Inc., N.Y., 2002.

Materials and methods suitable for the maintenance and growth of bacterial cultures are also well known in the art. Techniques suitable for use in the following Examples may be found in *Manual of Methods for General Bacteriology*, Phillipp Gerhardt, R. G. E. Murray, Ralph N. Costilow, Eugene W. Nester, Willis A. Wood, Noel R. Krieg and G. Briggs Phillips, eds., American Society for Microbiology, Washington, D.C., 1994, or in Brock (supra). All reagents, restriction enzymes and materials used for the growth and maintenance of bacterial cells were obtained from BD Diagnostic Systems (Sparks, Md.), Invitrogen (Carlsbad, Calif.), Life Technologies (Rockville, Md.), QIAGEN (Valencia, Calif.) or Sigma-Aldrich Chemical Company (St. Louis, Mo.), unless otherwise specified.

DEK Medium

The composition of DEK medium is provided in Table 2.

TABLE 2

Composition of DEK medium

| | Final concentration |
|---|---|
| DEK medium Components | |
| $KH_2PO_4$ | 9 g/L |
| $(NH_4)_2HPO_4$ | 4 g/L |
| Citric acid $*H_2O$ | 1.86 g/L |
| Yeast extract | 5 g/L |
| Post sterilization | |
| $MgSO_4*7H_2O$ | 1.2 g/L |
| Thiamine HCl | 4.5 mg/L |
| Uracil | 50 mg/L |
| Trace Elements Stock | 10 mL/L |
| Trace Elements Stock Composition | |
| EDTA | 840 mg/L |
| $CoCl_2*6H_2O$ | 250 mg/L |
| $MnCl_2*4H_2O$ | 1500 mg/L |
| $CuCl_2*2H_2O$ | 150 mg/L |
| $H_3BO_3$ | 300 mg/L |
| $Na_2MoO_4*2H_2O$ | 250 mg/L |
| $Zn(CH_3COO)_2*2H_2O$ | 1300 mg/L |
| Fe(III) citrate | 10000 mg/L |

Design of the Expression Plasmids

Several expression systems were used to produce the fusion proteins in an *E. coli* host cell. One expression system was based on *E. coli* strain BL21-AI (Invitrogen) in combination with a T7-based expression vector wherein expression of the T7 RNA polymerase is controlled by the araBAD promoter. Another expression system was based on *E. coli* MG1655 (ATCC 47076™) derived strain in combination with a pBAD-based expression vector wherein the endogenous chromosomal copy of the araBAD operon was deleted (the modified *E. coli* MG1655 strain comprising a disruption in the endogenous araBAD operon is referred to herein as *E. coli* strain KK2000).

The nucleic acid molecules encoding the various fusion peptides were designed to include at least one region encoding an inclusion body tag (IBT) linked to a peptide of interest (POI). Appropriate restriction sites were included to facilitate simple swapping of the portion encoding the inclusion body tag and/or peptide of interest. The inclusion body tag (IBT) and the peptide of interest (POI) were separated by a cleavable peptide linker (CS; for example, an acid cleavable DP moiety). Furthermore, the fusion peptide was also designed to include at least one tetracysteine tag (LUMIO™ tag; SEQ ID NO: 2) located on the C-terminus of the inclusion body tag wherein the tetracysteine tag was separated from the portion encoding the peptide of interest by the cleavable peptide linker.

Expression Plasmid pTG28 (also referred to herein as pTG028; SEQ ID NO: 19)) is a ColE1 plasmid that has a pBAD promoter expressing the fusion peptide containing the inclusion body tag KSI(C4) and HC77643. It also has the araC gene encoding the regulator and the bla gene conferring ampicillin resistance.

Expression Plasmid pTG34 (also referred to herein as pTG034; SEQ ID NO: 20) is a ColE1 plasmid that has a T7 promoter expressing the fusion peptide containing the inclusion body tag IBT139 and HC77643. It also has the bla gene conferring ampicillin resistance.

Expression Plasmid pLR173 (SEQ ID NO: 21) is a ColE1 plasmid that has a pBAD promoter expressing the fusion peptide containing the inclusion body tag IBT139 and HC77643. It also has araC encoding the regulator, bla conferring ampicillin resistance and the aadA-1 gene conferring spectinomycin resistance.

Plasmid pLR186 (SEQ ID NO: 18) contains a ColE1 type origin of replication, the bla gene to confer ampicillin resistance and the aadA-1 gene to confer spectinomycin (Spec) resistance. The fusion peptide containing inclusion body tag IBT139 fused with peptide HC124 (see U.S. patent application Ser. No. 11/782,836) was expressed by the pBAD promoter. The plasmid also encodes the gene for the araC regulator.

Figure 1D:
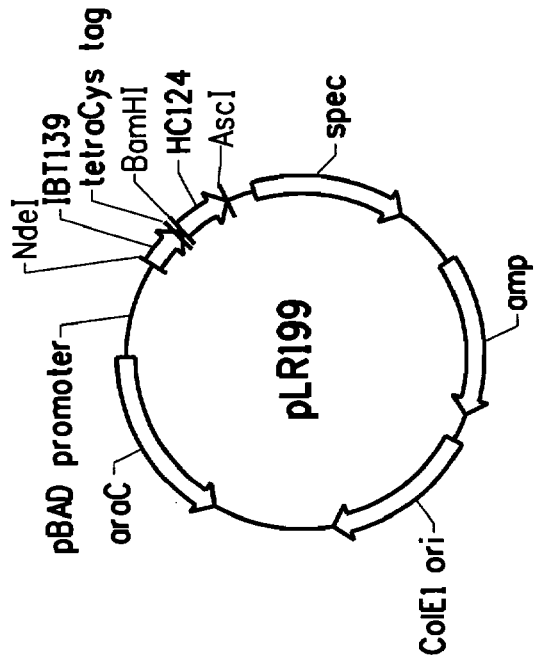

Plasmid pLR199 (FIG. 1D; SEQ ID NO: 22) was created from pLR186 by inserting an annealed oligonucleotide fragment encoding a tetracysteine tag CCPGCC (SEQ ID NO: 2) into the BamHI site between the inclusion body tag IBT139 (SEQ ID NO: 12) and HC776124 (SEQ ID NO: 10). The resulting fusion peptide was IBT139.CCPGCC-HC776124. Inclusion body tag IBT139.CCPGCC is provided as SEQ ID NOs: 13-14.

FACS System Operating Conditions:

A Fluorescence Activated Cell Sorter (FACSVantage™ SE-DiVa; Becton-Dickinson (BD Biosciences, Franklin Lakes, N.J.)) was configured with a single 488 nm argon ion laser (200 mW). The laser is used to induce light scattering by either the excitation of cellular fluorescent tags or the granularity within the cell. The SSC (Side Scatter Collector) light detection from the cell is collected through a microscope objective, transmitted via fiber light guide to an array of photo-multiplier tubes (PMT's). The FSC (Forward Scatter Collector) was constructed of a photo-diode. The SSC octagon configuration was composed of 5 PMT's in an octagon configuration. The LUMIO™ collection at 530 nm used a fluorescein isothiocyanate (FITC) filter (530 nm center, +/−15 nm bands) with a SSC filter of 488 nm bandpass (488 nm center, +/−10 nm bands). The system fluid used on the FACSVantage™ SE-DiVa was FACSFlow™ Sheath (Becton Dickinson) at an operating pressure of 28 psi (~193 kPa) using a 70 μm diameter orifice tip.

The standard daily alignment of the instrument was performed using ALIGNFLOW™ (Molecular Probes, Inc., Eugene, Oreg.) 2.5 μm diameter fluorescent beads at an excitation/emission of 488 nm. The ALIGNFLOW™ beads were used as the daily alignment standard and the following instrument adjustments were made on the FACS to obtain the maximum PMT signal and minimum CV (coefficient of variation) for all channels on the instrument. The ALIGNFLOW™ beads were used to enable the daily adjustment of the FACS nozzle (X, Y, Z, α, and θ); in addition to the focus lens, channel height and channel height focus in all detector channels. The alignment of the FACS system can vary, but with the use of the ALIGNFLOW™ beads, good alignment reproducibility was obtained. The ALIGNFLOW™ beads were either incorporated as a separate sample or directly into the sample to monitor the alignment and any potential instrument drift. The daily FACS alignment procedure, created in the DiVa Software (Becton Dickinson, v1.4), was performed and verified to within normal operating conditions.

The LUMIO™ stained cell samples were previously prepared in PBS (Phosphate Buffered Saline) which is similar to the sheath fluid; therefore, no additional manipulation was needed for FACS analysis. Approximately 200 μL of a sample containing LUMIO™ stained cells was placed into a Falcon 12×75 mm, sterile polystyrene culture tube (Becton Dickinson) and into the instrument. The sample differential pressure was adjusted to obtain a stable 1000 events/second; at which, between 20,000 and 50,000 sample events were recorded. The variation, in sample recorded events, was due to the variation in cell concentration and limited sample volume. If the observed events/s were observed to be low, then the recorded events were then decreased. The samples scanned on the FACS for LUMIO™ analysis included, but were not limited to, an ALIGNFLOW™ bead sample, unstained LUMIO™ (negative control) and a series of LUMIO™ stained samples (experimental). The data obtained for the FACS samples included several different plot windows; which included dot plots for FSC-A vs. SSC-A, FSC-A vs. FITC-A, SSC-A vs. FITC-A and histograms for SSC-A, FSC-A, and FITC-A (width×height) for the particular channel ("A" is the computed area; "FS" is forward scatter; and "SS" is side scatter). During the recording of each sample, a gate was set on the FITC-A histogram between the $10^3$ and $10^4$ (log scale) to monitor and observe the sample LUMIO™ labeling efficiency. The recorded events within the gate on the FITC-A log scale provided a good indication of the sample LUMIO™ labeling efficiency. The recorded LUMIO™ sample data was saved and then within the DiVA software they were exported as FCS3 data files for further analysis.

Example 1

Specific Labeling of Tetracysteine Tagged Fusion Peptides

This example describes cloning of the tetracysteine tag (CCPGCC; SEQ ID NO: 2) into three peptide expression plasmids in *E. coli*, which allowed specific labeling of the fusion peptides.

Specific labeling of proteins or peptides could be achieved by biarsenical ligands binding to tetracysteine tag ($CCX_1X_2CC$, SEQ ID NO: 1; wherein $X_1$ and $X_2$ are any amino acid other than cysteine, preferably $X_1X_2$ is PG; respectively (SEQ ID NO: 2)), which is genetically engineered into the target protein or peptide. The fluorescein derivative with two As(III) substituents, FlAsH-EDT$_2$ (LUMIO™ Green), only fluoresces after the arsenics bind to the cysteine thiols in the target protein or peptide. In order to reach high production yield and reduce separation costs, peptides of interest were produced as inclusion bodies in our *E. coli* production hosts. Inclusion body promoting sequences were usually fused to the N-terminus of the peptide of interest to drive peptide production into inclusion bodies. An acid cleavage site (DP) was introduced after the inclusion body promoting sequence to separate the inclusion body promoting sequence away from the peptide of interest after production. At least one tetracysteine tag (LUMIO™ tag; SEQ ID NO: 2) was cloned onto the C-terminus of the inclusion body tag wherein the tetracysteine tag was separated from the portion encoding the peptide of interest by the cleavable peptide linker. The LUMIO™ reagents used for fluorescent labeling were obtained from Invitrogen (Carlsbad, Calif.).

Figure 1C:
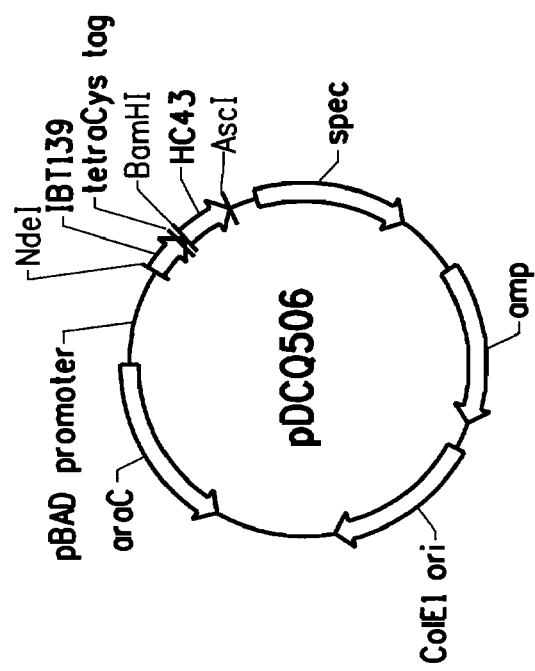
Figure 1E:
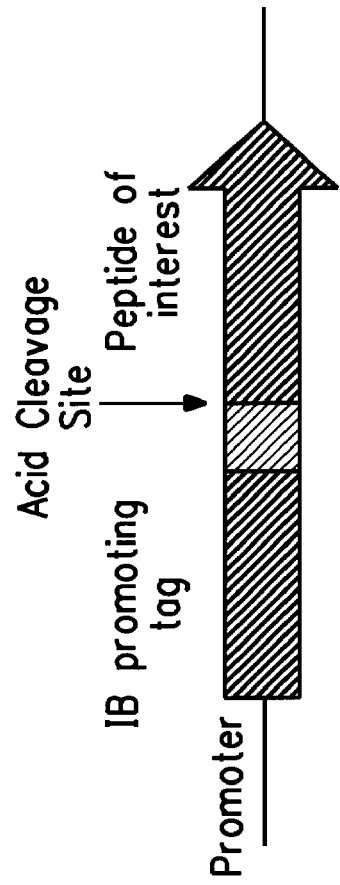
FIG. 1E illustrates the chimeric genetic construct encoding the peptide of interest targeted for expression as inclusion bodies. The tetracysteine tag (CCPGCC; SEQ ID NO: 2) was cloned between the inclusion body promoting tag (IBT) and the peptide of interest (POI) and upstream of the acid cleavage site, an acid labile aspartic acid-proline (DP) dipeptide.

The oligonucleotides encoding the tetracysteine tag CCPGCC (SEQ ID NO: 2) were synthesized by Sigma Genosys (The Woodlands, Tex.). The top strand oligo 5'-GA TCT TGC TGT CCG GGC TGT TGC G-3' (SEQ ID NO: 3) and the bottom strand oligo 5'-GA TCC GCA ACA GCC CGG ACA GCA A-3' (SEQ ID NO: 4) were annealed with a Bglll overhang at the 5' end and a BamHI overhang at the 3' end. The annealed double stranded fragment was cloned into the BamHI site of a peptide expression plasmid pTG28, which contained a nucleic acid molecule encoding peptide of interest HC77643 (SEQ ID NO: 8) fused to the inclusion body promoting sequence KSI(C4) (SEQ ID NO: 16) expressed by the $P_{BAD}$ promoter. The resulting clone pDCQ500 (FIG. 1A; SEQ ID NO: 23) contained the tetracysteine tag inserted after the inclusion body promoting sequence and before the acid cleavage site (FIG. 1E). The tetracysteine tag was also cloned similarly into two other peptide expression plasmids pTG34 (SEQ ID NO: 20) and pLR173 (SEQ ID NO: 21). Plasmid pLR173 contains a chimeric gene encoding the peptide of interest (HC77643; SEQ ID NO: 8) fused to a different inclusion body promoting sequence IBT139 (SEQ ID NO: 12) expressed by the $P_{BAD}$ promoter. Plasmid pTG34 contains a chimeric gene encoding the peptide of interest HC77643 fused to the IBT139 expressed by the T7 promoter. The tetracysteine tag was inserted between the IBT139 and HC77643 by cloning into the BamHI site of the parental plasmids pTG34 and pLR173, resulting in plasmids pDCQ502 (FIG. 1B; SEQ ID NO: 24) and plasmid pDCQ506 (FIG. 1C; SEQ ID NO: 25), respectively. Plasmids pDCQ500 and pDCQ506 were transformed into an E. coli K-derived production host KK2000 (MG1555 ΔaraBAD). Plasmid pDCQ502 was transformed into an E. coli B-derived production host BL21-AI (Invitrogen).

The cultures were grown from fresh overnight cultures to $OD_{600}$ 0.3-0.5, and were then induced with 0.2% L-arabinose (Sigma) for 3 to 4 hours at 37° C. Cells from 100 μL cultures were pelleted and resuspended in 50 μL B-Per lysis buffer (Pierce) or the lysis buffer containing 50 mM K phosphate buffer pH 7.8, 400 mM NaCl, 100 mM KCl, 10% glycerol, 0.5% Triton X-100, 10 mM imidazole, 1 mg/mL lysozyme (Sigma) and 13.6 units of DNase I (Qiagen, Valencia, Calif.). The lysates were spun at 14,000×g for 5 min to separate the supernatant and the inclusion body fraction. The inclusion body pellets were washed and resuspended in 8 M urea. The whole lysate or the separated supernatant and inclusion body fractions were stained with LUMIO™ Green detection reagent using the LUMIO™ Green detection kit (Invitrogen) following manufacturers' instructions. The samples were run on a NuPAGE® 4-12% Bis-Tris gel with the BenchMark™ fluorescent protein standard (Invitrogen). The gel was visualized under UV light. After taking a picture, the gel was rinsed, stained with SimplyBlue™ (Invitrogen) and destained with deionized water. The fusion peptides were specifically labeled in the lysates from strains containing the tetracysteine tag, whether the peptides were fused with the KSI(C4) or IBT139 inclusion body promoting sequences, and expressed by $P_{BAD}$ promoter in KK2000 strain or T7 promoter in BL21-AI strain. No protein was stained in the lysates from strains without the tetracysteine tag. Incorporation of one copy of the tetracysteine tag into these peptides neither affected the peptide expression nor the peptide partition in the production hosts.

Example 2

In Vivo Fluorescent Labeling of E. coli Cells Producing the Tagged Peptides Visualized by Fluorescence Microscope To explore if the live E. coli cells producing the tetracysteine-tagged peptides could be labeled in vivo without cell lysis or membrane permeabilization, we performed the labeling of the live E. coli cells using the LUMIO™ in-cell labeling kit (catalog no. 12589-057) or the TC-FlAsH™ TC-ReAsH™ II in-cell tetracysteine tag detection kit (catalog no. T34561) from Invitrogen, which are designed for labeling mammalian cells in vivo. The E. coli cells were grown and induced as described above. Normalized amounts of 100-200 μL of $OD_{600}$ 0.01 cells were pelleted and used in labeling reactions containing 1×PBS, 0.2% L-arabinose, appropriate antibiotics, 1 μM TCEP (Tris[2-carboxyethyl] phosphine) and 10-20 μM LUMIO™ reagent. In the only report of LUMIO In-Cell labeling in E. coli, Ignatova and Gierasch (PNAS 101 (2):523-528, 2004) used much higher concentrations of the labeling reagent (up to 1 mM). The reactions were incubated at room temperature in the dark for 90-120 min. The cells were washed twice with PBS containing 20 μM Disperse Blue 3 (1-((2-Hydroxyethyl)amino)-4-(methylamino) anthraquinone; CAS# 2475-46-9) or 250 μM BAL wash buffer provided in the kits, and visualized under a fluorescent light microscope with the appropriate filter for fluorescein isothiocyanate (FITC). Fluorescent staining was observed specific for the inclusion bodies usually found at the distal ends of the cells. Minimal background was observed for uninduced cells not producing any tagged fusion peptide.

Viability of cells was also checked with the LIVE/DEAD® BacLight® bacterial viability kit (by Molecular Probes, available from Invitrogen), which utilizes the fluorescent nucleic acid stains SYTO® 9 (Molecular Probes) and propidium iodide. A fraction of induced cells was stained in suspension according to the manufacturer's instructions and examined by fluorescent light microscope using the broad band filter. Vast majority of cells fluoresced green, which indicated that the induced peptide-producing cells were still viable. The LUMIO™ in cell labeling was able to stain the inclusion bodies in the live E. coli cells without membrane permeabilization.

Example 3

FACS Analysis of LUMIO™-Labeled E. coli B Cells

E. coli BL21-AI cells containing the pDCQ502 and the parent pTG34 plasmids were grown to $OD_{600}$ about 0.5 and either continue to grow as un-induced or induced with 0.2% L-arabinose for 2.5 hours. Cells were then normalized to $OD_{600}$ of 0.01 and were labeled by LUMIO™ in vivo as described in Example 2. Approximately $10^5$-$10^6$ labeled cells were analyzed with a FACS Vantage™ SE with Digital Vantage manufactured by Becton Dickinson (BD Biosciences, Franklin Lakes, N.J.). The FACS instrument was configured and aligned as described in the General Methods. Twenty-thousand events were recorded for each sample. Data summarized in Table 3 showed that E. coli BL21-AI cells containing the pTG34 plasmid (i.e. the plasmid does not contain the nucleic acid sequence encoding the tetracysteine tag) were not labeled by LUMIO™ Green. Induced BL21-AI cells containing the pDCQ502 plasmid encoding a fusion peptide comprising the tetracysteine tag (CCPGCC; SEQ ID NO: 2) were labeled by LUMIO™ Green. Uninduced cells not making the peptide were not labeled. This suggested that LUMIO Green specifically labeled the tagged peptide in vivo and the fluorescent intensity generated by LUMIO™ labeling is sensitive for FACS analysis.

TABLE 3

Percentage of labeled cells by FACS analysis

| Strain | % labeled cells (FITC $10^2$-$10^4$) |
|---|---|
| BL21-AI (pTG34) uninduced | 6.8 |
| BL21-AI (pTG34) induced | 10.5 |
| BL21-AI (pDCQ502) uninduced | 4.5 |
| BL21-AI (pDCQ502) induced | 91.2 |

Example 4

FACS Analysis of LUMIO™ Labeled E. coli K Cells

It was reported (Stroffekova, K., et al, *Pflugers Arch-Eur J Physiol*, 442:859-866 (2001)) that the LUMIO™ labeling reagent binds not only to CCXXCC (SEQ ID NO: 1) motifs, but also non-specifically to endogenous cysteine-rich proteins. *E. coli* MG1655 SlyD is a cysteine-rich protein that might contribute to the background of LUMIO™ labeling (Keppetipola, S., et al, *Focus* 25.3:7-11 (2003) and U.S. Pat. App. Pub. US20050136449). A SlyD deletion strain was constructed in KK2000 by P1 transduction using general protocols as outlined in *Experiments in Molecular Genetics*, Miller, J. H., 1972, Cold Spring Harbor Laboratory Press, Cold Spring Harbor, N.Y. The SlyD deletion strain JW3311 in the Keio collection (Baba, T., et al, 2006, *Molecular Systems Biology*, 1-11; article #2006.0008) was used as the donor. The kanamycin resistant P1 phage was isolated and was used to transduce the KK2000 recipient. The kanamycin resistant marker flanked by FLP sites was then removed by transient expression of the Flp recombinase on a temperature-sensitive plasmid pCP20 (ATCC PTA-4455; U.S. patent application Ser. No. 10/734,936; and Cherepanov and Wackernagel (*Gene*, 158:9-14 (1995)). Loss of kanamycin resistance marker and deletion of slyD in KK2000 was confirmed by PCR. The resulting strain was designated as QC1100.

Plasmid pLR199 or pLR186 was transformed into QC1100. Plasmid pLR199 (FIG. 1D; SEQ ID NO: 22) comprises a chimeric gene encoding the fusion peptide of IBT139.CCPGCC-HC776124 expressed by pBAD promoter. HC776124 (SEQ ID NO: 10) is a dimer of HC77643 linked together by Pro-Gly linker. Plasmid pLR186 was the parent of pLR199 without the tetracysteine tag. *E. coli* QC1100 (pLR199) or QC1100(pLR186) cells were grown to $OD_{600}$ about 0.5 and induced with 0.2%, 0.02%, 0.002%, 0.0002% or 0% L-arabinose for 2.5 hours. Cells were then normalized to $OD_{600}$ of 0.01. Approximately $10^5$-$10^6$ cells were labeled by LUMIO™ and analyzed by FACS as described in Example 2. FACS analysis showed that uninduced cells or the vast majority of cells induced with low concentrations of arabinose (0.0002% or 0.002%) were not labeled. Cells induced with high concentrations of arabinose (0.02% or 0.2%) were labeled. Cells with and without the tetracysteine tag were both labeled, which cells with the tag showed higher fluorescent intensity. Table 3 summarized percentage of fluorescent labeled cells within the $10^3$-$10^4$ gate and within the $10^2$-$10^3$ gate. The fluorescent labeling of the peptide without the tetracysteine tag might be due to nonspecific labeling of the inclusion body structure of the fusion peptide.

TABLE 4

Percentage of labeled cells by FACS analysis

| % L-arabinose | % QC1100(pLR199) cells | | % QC1100(pLR186) cells | |
|---|---|---|---|---|
| | FITC $10^2$-$10^3$ | FITC $10^3$-$10^4$ | FITC $10^2$-$10^3$ | FITC $10^3$-$10^4$ |
| 0 | 1.8 | 0.04 | 1.2 | 0.1 |
| 0.0002 | 4.4 | 0.2 | 0.8 | 0.06 |
| 0.002 | 37.2 | 1.4 | 7.0 | 0.1 |
| 0.02 | 37.8 | 51.1 | 7.4 | 1.9 |
| 0.2 | 21.3 | 65.6 | 76.7 | 6.3 |

The high fluorescent 1% and low fluorescent 1% cells were collected from QC1100(pLR199) induced with 0.2% L-arabinose. They were plated onto LB plates containing 100 µg/mL ampicillin. Similar numbers of colonies were recovered from the high fluorescent and low fluorescent fractions. The ability of obtaining viable cells after LUMIO™ labeling and sorting indicates that the labeling process was suitable for FACS sorting.

Example 5

FACS Sorting of High Fluorescent Cells Based on LUMIO™ Labeling

This example demonstrates that using FACS based on fluorescence generated from LUMIO™ labeling, it was possible to sort out high fluorescent cells from low fluorescent cells. This could be exploited to isolate cells producing higher titers of peptides.

*E. coli* QC1100(pLR199) cells and QC1100(pLR186) cells were grown to $OD_{600}$ about 0.5 and induced with 0.2% L-arabinose for 2.5 hours. The induced cells from the two strains were mixed in 1:1 ratio. Approximately $10^5$-$10^6$ of mixed cells as well as cells of the two individual strains were labeled by LUMIO™ and analyzed by FACS as described in Example 4. Cells of QC1100(pLR199) showed a peak of higher fluorescence with mean of fluorescent intensity as 1387. Cells of QC1100(pLR186) showed a peak of lower fluorescence with mean of fluorescent intensity as 778. Cells from the mixture showed two overlapping peaks indicating of the mixed population.

The 1% high fluorescent cells from the mixed population were collected on LB plates with ampicillin (100 µg/mL) and grown at 37° C. overnight. Approximately 1270 colonies were produced on the plates. Twenty-two colonies were randomly picked for in-gel labeling as described in Example 1 to identify the isolated strains. The LUMIO™ tagged fusion protein in the extract of QC1100(pLR199) cells could be fluorescently labeled in the gel. The peptide without the LUMIO™ tag in the extract of QC1100(pLR186) cells could not be fluorescently labeled in the gel. Results showed that among the 22 colonies randomly picked, all were QC1100 (pLR199). This demonstrated that the highly fluorescent QC1100(pLR199) cells can be sorted out from the mixture by a single round of FACS sorting based on LUMIO™ in-cell labeling.

Example 6

Increased LUMIO™ In-Cell Labeling Reflected Increased Peptide Production

Figure 2A:
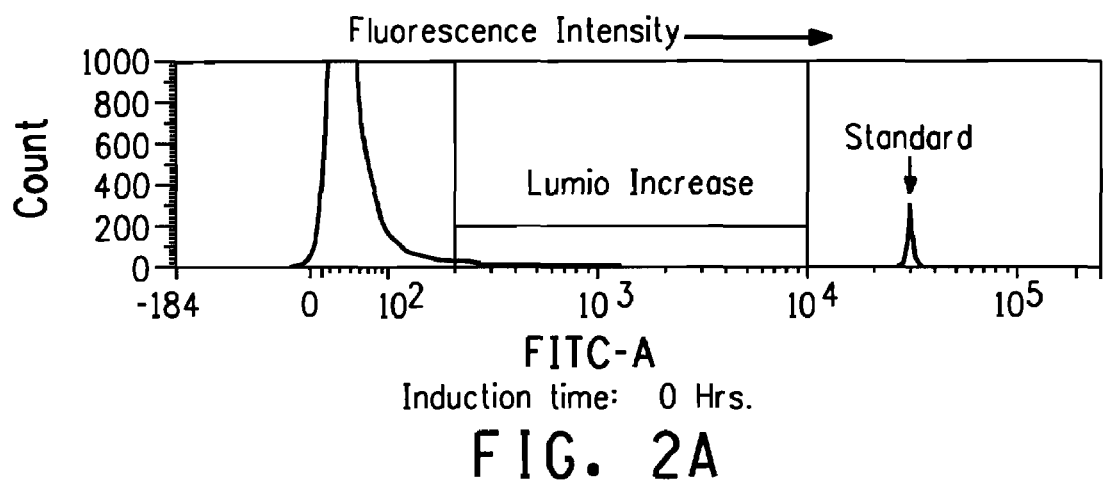
FIGS. 2A-2F are fluorescence activated cell sorter (FACS) fluorescence intensity plots illustrating increased LUMIO™ in-cell labeling at various induction times. The increase in fluorescence intensity reflects increased peptide production. QC1100 cells expressing the fusion peptide IBT139-CCPGCC-HC776124 with a tetracysteine tag were grown from fresh overnight cultures to $OD_{600}$ 0.5 and induced with 0.2% L-arabinose for different lengths of time. Aliquots of the induced cultures were used for in-cell labeling for FACS analysis (FIGS. 2A-2F) and in-gel LUMIO™ Green labeling (FIG. 2G). The same gel stained with SimplyBlue™ is shown in FIG. 2H. The column labels refer to a molecular weight marker lane (M) and the various induction times (in hours) prior to labeling.
Figure 2B:
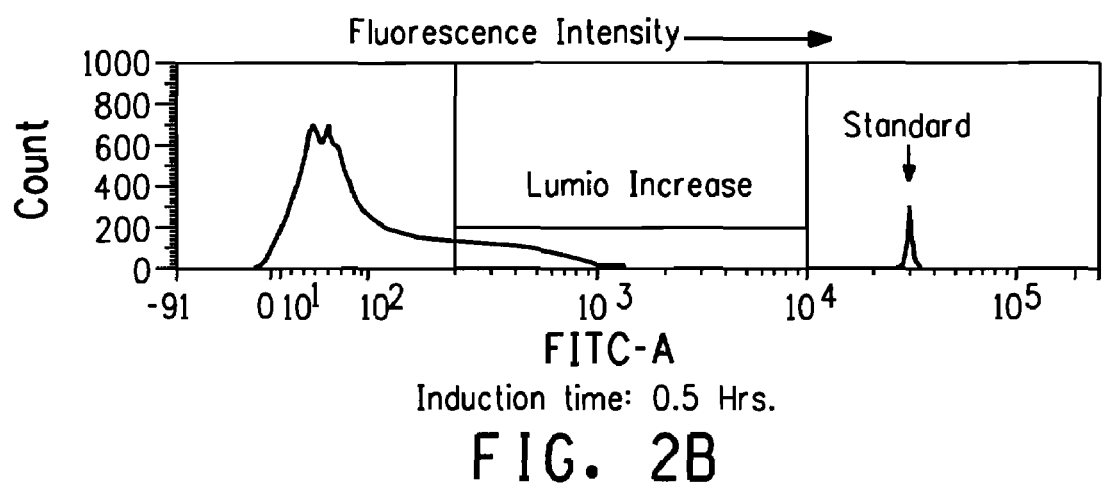
Figure 2C:
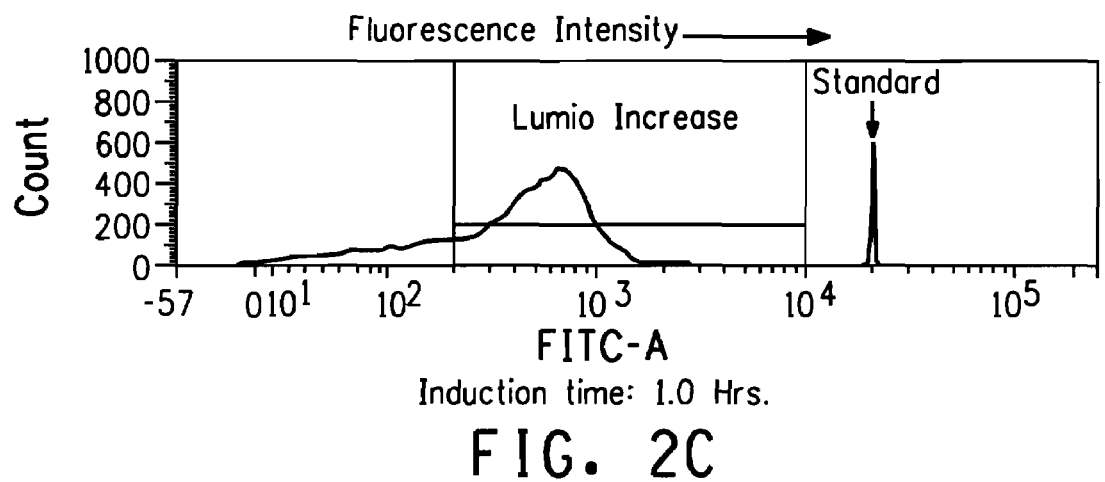
Figure 2D:
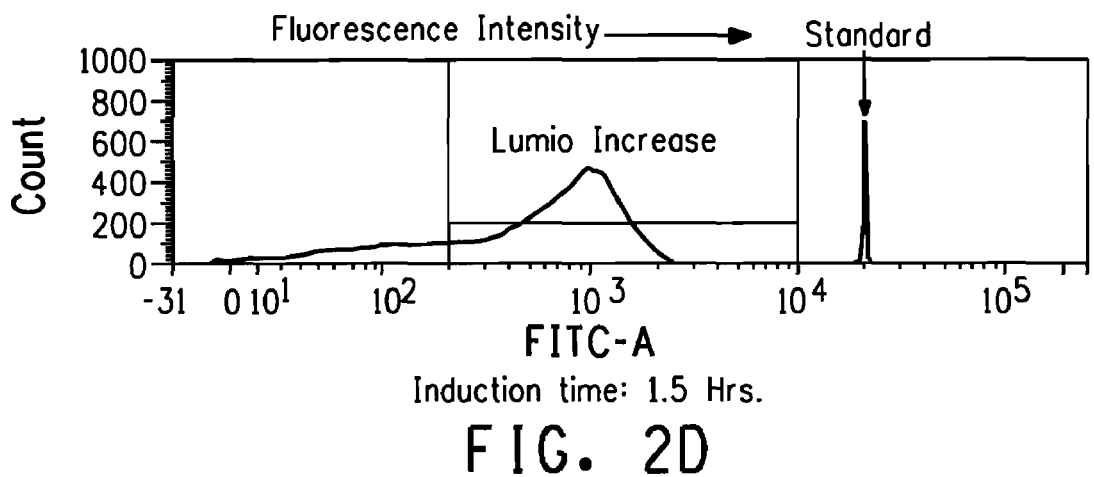
Figure 2E:
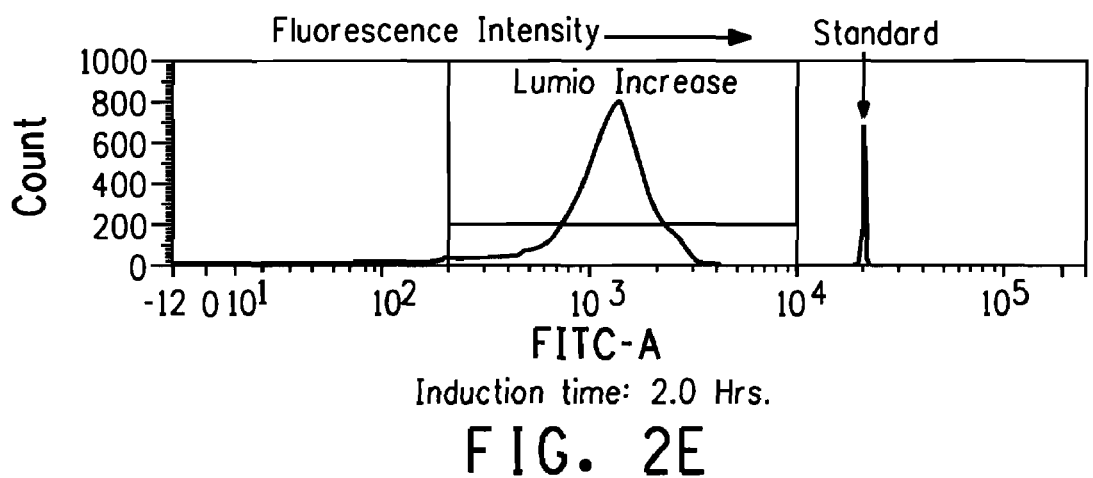
Figure 2F:
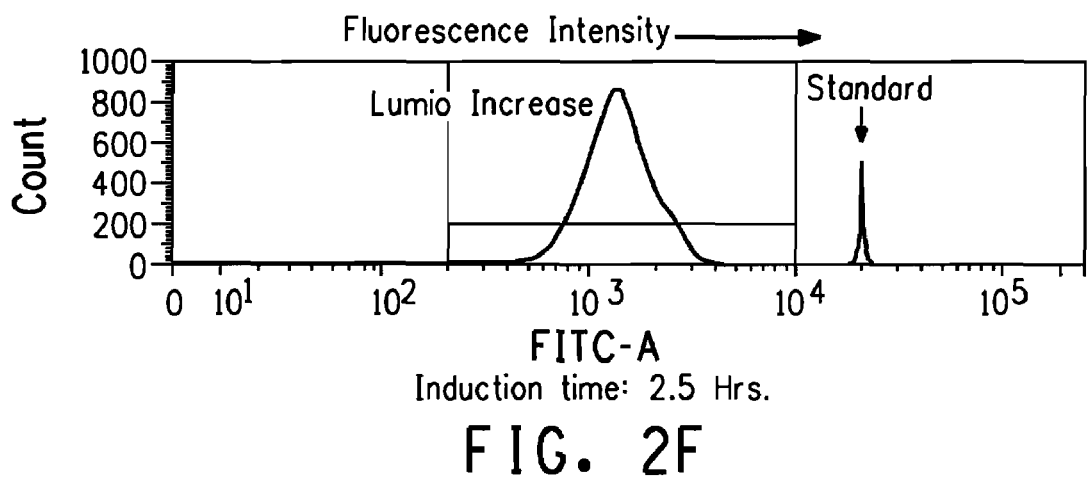
Figure 2G:
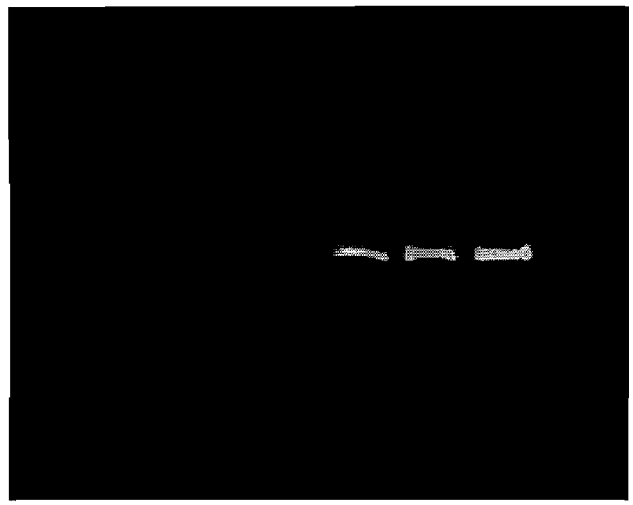
Figure 2H:
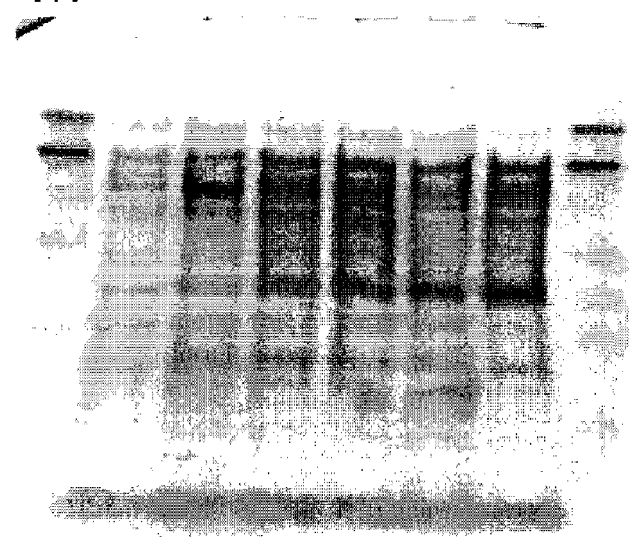

QC1100 cells expressing the fusion peptide IBT139-CCPGCC-HC776124 with the tetracysteine tag were grown from fresh overnight cultures for 1.5 hours to $OD_{600}$ ~0.5 and induced with 0.2% L-arabinose for different lengths of time (0, 0.5, 1, 1.5, 2, and 2.5 hours). Aliquots of the induced cultures were diluted and approximately $3 \times 10^6$ cells were used for in-cell labeling as described above. The labeled cells were washed and subjected for FACS analysis. Additional aliquots of the induced cultures of $OD_{600}$ ~1 were normalized and pelleted for in-gel labeling as described in Example 1. The labeled peptides were separated on a NUPAGE® 4-12% Bis-Tris gel and visualized under UV light. FIGS. 2A-2F show the FACS analysis results at different induction times. FIGS. 2G and 2H show the corresponding peptide gel analysis results. As the induction time increases, cells produced more peptide as shown by the increased fluorescence intensity of the peptide product on the gel. FACS analysis also showed the increased fluorescent intensity at a single cell level, which reflected increased peptide production. The non-linear increase of fluorescent intensity by FACS was most likely due to the all-or-non nature of arabinose induction at

Example 7

FACS Analysis of LUMIO™ Labeled *E. coli* Cells Grown in DEK Medium

This example describes LUMIO™ in-cell labeling of *E. coli* cells expressing the fusion peptide containing the tetracysteine tag grown in a minimal based DEK medium (Table 2).

Figure 3A:
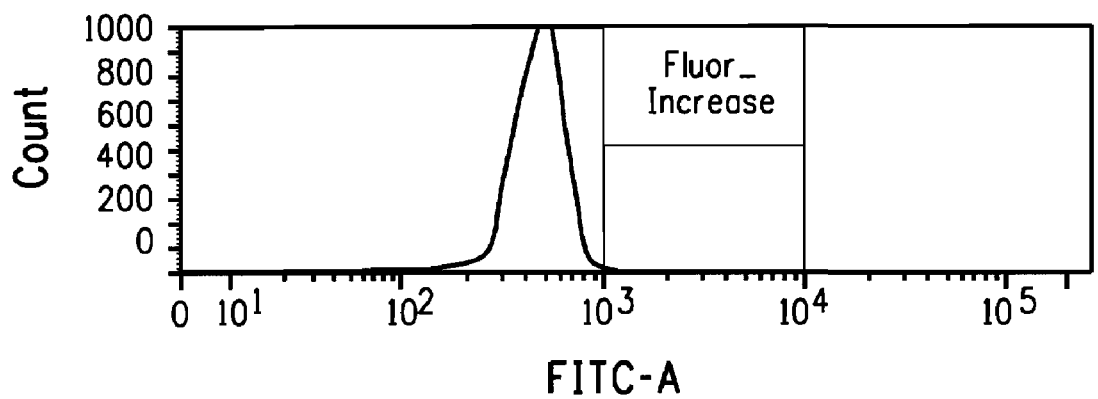
FIGS. 3A and 3B are fluorescence activated cell sorter (FACS) fluorescence intensity plots of the LUMIO™ in-cell labeling of QC1100 cells expressing the fusion peptide IBT139-CCPGCC-HC776124 with the tetracysteine tag.
Figure 3B:
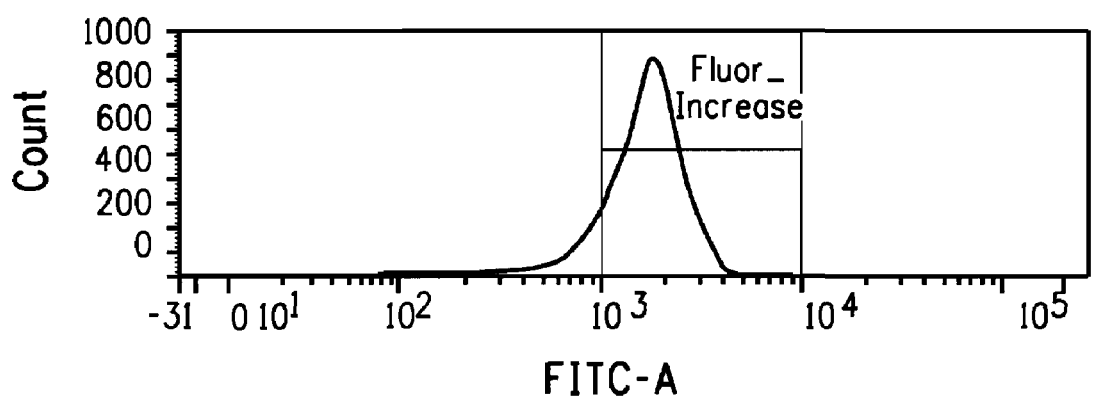

QC1100 cells expressing the fusion peptide IBT139-CCPGCC-HC776124 with the tetracysteine tag were grown in LB with appropriate antibiotics overnight. The cells were subcultured 1:100 from fresh overnight cultures into DEK medium (see General Methods for composition). Growth in DEK medium was monitored and aliquots of cells were taken out for induction with 0.2% L-arabinose at different $OD_{600}$. After postinduction growth for 3 hours, aliquots of the induced cultures were diluted and approximately $3 \times 10^6$ cells were used for in-cell labeling in labeling reactions containing 1×DEK medium, 0.2% L-arabinose, appropriate antibiotics, 1 µM TCEP (Tris[2-carboxyethyl]phosphine) and 20 µM LUMIO™ reagent. The labeled cells were washed and subjected to FACS analysis. Results showed that cells were not highly labeled if they were induced at low $OD_{600}$ values (<1.0). Cells were better labeled if they were induced at $OD_{600}$>1.0. Even with the optimal labeling as shown in FIG. 3A, DEK grown cells showed lower fluorescence intensity (mean ~500) than the LB grown cells (mean of fluorescent intensity ~1500; FIG. 3B). Normalized amount of cells from the induced cultures were also used for in-gel labeling. It appeared that DEK grown cells produced less peptide than the LB grown cells. This was consistent with the FACS data showing lower fluorescent intensity of the labeled DEK grown cells.

LUMIO™ in-cell labeling of *E. coli* cells expressing the fusion peptide containing the tetracysteine tag was also achieved in other rich media such as 2xYT or other minimal media such as M9.

---

What is claimed is:

1. A process for in vivo labeling and detecting a polypeptide or protein in a prokaryotic cell comprising:
   a) providing an unpermeabilized prokaryotic host cell comprising a chimeric genetic construct encoding a polypeptide or protein comprising at least one tetracysteine tag;
   b) growing the unpermeabilized prokaryotic host cell of (a) under suitable conditions to express the chimeric genetic construct and to produce the polypeptide or protein comprising said at least one tetracysteine tag;
   c) contacting in vivo the prokaryotic host cell of (b) with an effective amount of at least one biarsenical labeling reagent that binds to the at least one tetracysteine tag forming at least one fluorescent complex, wherein said contacting is performed in the absence of a reducing agent; and
   d) detecting the prokaryotic cell comprising the at least one fluorescent complex by utilizing a fluorescence activated cell sorter (FACS) to select a subpopulation of cells which display the highest fluorescence.

2. The process of claim 1, whereby the chimeric genetic construct encodes a fusion peptide comprising:
   i) at least one first portion comprising an inclusion body tag (IBT);
   ii) at least one second portion comprising a peptide of interest (POI); and
   iii) at least one tetracysteine tag (TC).

3. The process of claim 1, wherein the prokaryotic host cell is an enteric bacteria.

4. The process of claim 1, wherein the effective amount of the at least one biarsenical labeling reagent ranges from about 5 µM to less than 150 µM.

5. The process of claim 1, wherein the tetracysteine tag comprises the amino acid sequence of SEQ ID NO: 2.

6. The process of claim 1, wherein the at least one biarsenical labeling reagent is selected from the group consisting of fluorescein arsenical hairpin binding reagent and resorufin arsenical hairpin binding reagent.

7. The process of claim 2, wherein the genetic construct further comprises a nucleic acid molecule encoding a cleavable peptide linker located between the tetracysteine tag and the peptide of interest.

8. The process of claim 7, wherein the at least one first portion comprising the inclusion body tag comprises the at least one tetracysteine tag.

9. The process of claim 1, wherein steps (a) through (d) are optionally repeated.

10. The process of claim 1, further comprising the step of:
   (e) subjecting the selected subpopulation to at least one mutagenic procedure capable of introducing at least one genetic alteration to the selected cell which increases the production of said tetracysteine tagged polypeptide or protein.

11. The process of claim 10, wherein steps (a) through (e) are optionally repeated.

12. The process of claim 2 wherein said fusion peptide comprises the structure:

IBT-TC-CL-POI or POI-CL-TC-IBT wherein
   a) CL is a cleavable peptide linker;
   b) the tetracysteine tag comprises amino acid sequence SEQ ID NO: 2;
   c) the biarsenical labeling reagent is selected from the group consisting of fluorescein arsenical hairpin binding reagent and resorufin arsenical hairpin binding reagent; and
   d) the prokaryotic cell is *Escherichia coli*.

13. A process for making an improved fusion protein comprising:
   a) providing an unpermeabilized prokaryotic host cell comprising a chimeric genetic construct encoding a polypeptide or protein comprising at least one tetracysteine tag;
   b) subjecting the unpermeabilized prokaryotic cell of (a) to a mutagenic procedure to produce a pool of mutagenized prokaryotic cells which display increased tetracysteine tagged polypeptide or protein production;
   c) inducing expression of the chimeric genetic construct to produce a fusion peptide comprising the tetracysteine tag;
   d) labeling the fusion peptide in vivo with a biarsenical labeling reagent in the absence of a reducing agent;
   e) isolating a subpopulation of the labeled, unpermeabilized prokaryotic cells exhibiting increased fluorescence; and
   f) amplifying the isolated prokaryotic cells by growing in liquid medium or on plates; and
   g) optionally repeating steps (b)-(f).

* * * * *